United States Patent
Südhof et al.

(10) Patent No.: US 7,081,337 B2
(45) Date of Patent: Jul. 25, 2006

(54) METHODS FOR MODULATING TRANSCRIPTIONAL ACTIVATION USING MINT PROTEINS

(75) Inventors: Thomas C. Südhof, Dallas, TX (US); Thomas Biederer, Dallas, TX (US); Angela Ho, Dallas, TX (US); Xinran Liu, Irving, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/227,490

(22) Filed: Aug. 23, 2002

(65) Prior Publication Data

US 2003/0036169 A1 Feb. 20, 2003

Related U.S. Application Data

(63) Continuation-in-part of application No. 09/821,861, filed on Mar. 30, 2001, now Pat. No. 6,649,346.

(51) Int. Cl.
*C12Q 1/68* (2006.01)
*C12P 19/34* (2006.01)
*C12N 1/12* (2006.01)
*C12N 1/20* (2006.01)
*C12N 5/08* (2006.01)

(52) U.S. Cl. .................. 435/6; 435/91.1; 435/320.1; 435/366; 435/252.1; 435/252.3

(58) Field of Classification Search ............. 435/320.1, 435/6, 41, 69.1, 69.7, 69.8, 69.9, 455, 471; 424/192.1
See application file for complete search history.

(56) References Cited

U.S. PATENT DOCUMENTS

2001/0034884 A1 10/2001 Peraus ........................... 800/3

OTHER PUBLICATIONS

Mori A, Okuyama K, Horie M, Taniguchi Y, Wadatsu T, Nishino N, Shimada Y, Miyazawa N, Takeda S, Niimi M, Kyushiki H, Kondo M, Mitsumoto Y. Alteration of methamphetamine-induced striatal dopamine release in mint-1 knockout mice. Neurosci Res Jul. 2002;43(3):251-257.

Biederer T, Sudhof TC. CASK and protein 4.1 support F-actin nucleation on neurexins. J Biol Chem Dec. 21, 2001;276(51):47869-47876.

Cao X, Sudhof TC. A transcriptionally [correction of transcriptively] active complex of APP with Fe65 and histone acetyltransferase Tip60. Science Jul. 6, 2001;293(5527):115-120.

Cupers P, Orlans I, Craessaerts K, Annaert W, De Strooper B. The Amyloid precursor protein (APP)-cytoplasmic fragment generated by gamma-secretase is rapidly degraded but distributes partially in a nuclear fraction of neurones in culture. J Neurochem Sep. 2001;78(5):1168-1178.

Gao Y, Pimplikar SW. The gamma -secretase-cleaved C-terminal fragment of amyloid precursor protein mediates signaling to the nucleus. Proc Natl Acad Sci U S A Dec. 18, 2001;98(26):14979-14984.

Kimberly WT, Zheng JB, Guenette Sy, Selkoe DJ. The intracellular domain of the beta-amyloid precursor protein is stabilized by Fe65 and translocates to the nucleus in a notch-like manner. J Biol Chem Oct. 26, 2001;276(43):40288-40292.

Sastre M, Steiner H, Fuchs K, Capell A, Multhaup G, Condron MM, Teplow DB, Haass C. Presenilin-dependent gamma-secretase processing of beta-amyloid precursor protein at a site corresponding to the S3 cleavage of Notch. EMBO Rep Sep. 2001;2(9):835-841.

Wolfe MS, Haass C. The Role of presenilins in gamma-secretase activity. J Biol Chem Feb. 23, 2001;276(8):5413-5416.

Yu C, Kim SH, Ikeuchi T, Xu H, Gasparini L, Wang R, Sisodia SS. Characterization of a presenilin-mediated amyloid precursor protein carboxyl-terminal fragment gamma. Evidence for distinct mechanisms involved in gamma -secretase processing of the APP and Notch1 transmembrane domains. J Biol Chem Nov. 23, 2001;276(47):43756-43760.

Biederer T, Sudhof TC. Mints as adaptors. Direct binding to neurexins and recruitment of munc18. J Biol Chem Dec. 22, 2000;275(51):39803-39806.

Brown MS, Ye J, Rawson RB, Goldstein JL. Regulated intramembrane proteolysis: a control mechanism conserved from bacteria to humans. Cell Feb. 18, 2000;100(4):391-398.

(Continued)

*Primary Examiner*—Olga N. Chernyshev
(74) *Attorney, Agent, or Firm*—Baker Botts L.L.P.

(57) ABSTRACT

The present invention is directed to isolated nucleic acids encoding Mint protein variants having enhanced abilities to modulate the transcriptional activation mediated by the cytoplasmic tail of the amyloid precursor protein (APP) relative to wild-type Mint proteins. The present invention is further directed toward purified Mint protein variants having enhanced abilities to modulate the transcriptional activation mediated by the cytoplasmic tail of APP relative to wild-type Mint proteins. The present invention also encompasses methods of modulating transcriptional activation and methods of identifying compounds that modulate transcriptional activation, and vectors, as well as transfected cells and kits useful for modulating transcriptional activation or for the identification of compounds that can modulate transcriptional activation. The present invention further encompasses transgenic knockout mice with little or no expression of Mint 1, Mint 2 or Mint 3 proteins. Such reagents may be useful as candidate therapeutics for Alzheimer's disease (AD), or as models for the rational design of drugs useful for the treatment of AD.

7 Claims, 48 Drawing Sheets

OTHER PUBLICATIONS

Esler WP, Kimberly WT, Ostaszewski BL, Diehl TS, Moore CL, Tsai JY, Rahmati T, Xia W, Selkoe DJ, Wolfe MS. Transition-state analogue inhibitors of gamma-secretase bind directly to presenilin-1. Nat Cell Biol Jul. 2000;2(7):428-434.

Lau KF, McLoughlin DM, Standen C, Miller CC. XII alpha and x11 beta interact with presenilin-1 via their PDZ domains. Mol Cell Neurosci Nov. 2000;16(5):557-565.

Mueller HT, Borg JP, Margolis B, Turner RS. Modulation of amyloid precursor protein metabolism by XIIalpha /Mint-1. A deletion analysis of protein-protein interaction domains. J Biol Chem Dec. 15, 2000;275(50):39302-39306.

Okamoto M, Matsuyama T, Sugita M. Ultrastructural localization of mint1 at synapses in mouse hippocampus. Eur J Neurosci Aug. 2000;12(8):3067-3072.

Setou M, Nakagawa T, Seog DH, Hirokawa N. Kinesin superfamily motor protein KIF17 and mLin-10 in NMDA receptor-containing vesicle transport. Science Jun. 9, 2000;288(5472):1796-1802.

Struhl G, Adachi A. Requirements for presenilin-dependent cleavage of notch and other transmembrane proteins. Mol Cell Sep. 2000;6(3):625-636.

Verhage M, Maia AS, Plomp JJ, Brussaard AB, Heeroma JH, Vermeer H, Toonen RF, Hammer RE, van den Berg TK, Missler M, Geuze HJ, Sudhof TC. Synaptic assembly of the brain in the absence of neurotransmitter secretion. Science Feb. 4, 2000;287(5454):864-869.

Bayer TA, Cappai R, Masters CL, Beyreuther K, Multhaup G. It all sticks together—the APP-related family of proteins and Alzheimer's disease. Mol Psychiatry Nov. 1999;4(6):524-528.

Borg JP, Lopez-Figueroa MO, de Taddeo-Borg M, Kroon DE, Turner RS, Watson SJ, Margolis B. Molecular analysis of the XII-mLin-2/CASK complex in brain. J Neurosci Feb. 15, 1999;19(4):1307-1316.

De Strooper B, Annaert W, Cupers P, Saftig P, Craessaerts K, Mumm JS; Schroeter EH, Schrijvers V, Wolfe MS, Ray WJ, Goate A, Kopan R. A presenilin-1-dependent gamma-secretase-like protease mediates release of Notch intracellular domain. Nature Apr. 8, 1999;398(6727):518-522.

Haass C, De Strooper B. The presenilins in Alzheimer's disease—proteolysis holds the key. Science Oct. 29, 1999;286(5441):916-919.

McLoughlin DM, Irving NG, Brownlees J, Brion JP, Leroy K, Miller CC. Mint2/XII-like colocalizes with the Alzheimer's disease amyloid precursor protein and is associated with neuritic plaques in Alzheimer's disease. Eur J Neurosci Jun. 1999;11(6):1988-1994.

Steiner H, Duff K, Capell A, Romig H, Grim MG, Lincoln S, Hardy J, Yu X, Picciano M, Fechteler K, Citron M, Kopan R, Pesold B, Keck S, Baader M, Tomita T, Iwatsubo T, Baumeister R, Haass C. A loss of function mutation of presenilin-2 interferes with amyloid beta-peptide production and notch signaling. J Biol Chem Oct. 1, 1999; 274(40):28669-28673.

Struhl G, Greenwald I. Preseniln is required for activity and nuclear access of Notch in Drosophila. Nature Apr. 8, 1999;398(6727):522-525.

Whitfield CW, Benard C, Barnes T, Hekimi S, Kim SK. Basolateral localization of the Caenorhabditis elegans epidermal growth factor receptor in epithelial cells by the PDZ protein LIN-10. Mol Biol Cell Jun. 1999;10(6):2087-2100.

Ye Y, Lukinova N, Fortini ME.Neurogenic phenotypes and altered Notch processing in Drosophila Presenilin mutants. Nature Apr. 8, 1999;398(6727):525-529.

Borg JP, Straight SW, Kaech SM, de Taddeo-Borg M, Kroon DE, Karnak D, Turner RS, Kim SK, Margolis B. Identification of an evolutionarily conserved heterotrimeric protein complex involved in protein targeting. J Biol Chem Nov. 27, 1998;273(48):31633-31636.

Borg JP, Yan Y, De Taddeo-Borg M, Margolis B, Turner RS. The XIIalpha protein slows cellular amyloid precursor protein processing and reduces Abeta40 and Abeta42 secretion. J Biol Chem Jun. 12, 1998;273(24):14761-14766.

Butz S, Okamoto M, Sudhof TC. A tripartite protein complex with the potential to couple synaptic vesicle exocytosis to cell adhesion in brain. Cell Sep. 18, 1998;94(6):773-782.

Kaech SM, Whitfield CW, Kim SK. The LIN-2/LIN-7/LIN-10 complex mediates basolateral membrane localization of the C. elegans EGF receptor LET-23 in vulval epithelial cells. Cell Sep. 18, 1998;94(6):761-771.

Okamoto M, Südhof TC. Mint 3: a ubiquitous mint isoform that does not bind to munc18-1 or -2. Eur J Cell Biol Nov. 1998;77(3):161-165.

Rongo C, Whitfield CW, Rodal A, Kim SK, Kaplan JM. LIN-10 is a shared component of the polarized protein localization pathways in neurons and epithelia. Cell Sep. 18, 1998;94(6):751-759.

Sastre M, Turner RS, Levy E. XII interaction with beta-amyloid precursor protein modulates its cellular stabilization and reduces amyloid beta-protein secretion. J Biol Chem Aug. 28, 1998:273(35):22351-22357.

Selkoe DJ. The cell biology of beta-amyloid precursor protein and presenilin in Alzheimer's disease. Trends Cell Biol Nov. 1998;8(11):447-453.

Okamoto M, Sudhof TC. Mints, Munc18-interacting proteins in synaptic vesicle exocytosis. J Biol Chem Dec. 12, 1997;272(50):31459-64.

Zhang Z, Lee CH, Mandiyan V, Borg JP, Margolis B, Schlessinger J, Kuriyan J. Sequence-specific recognition of the internalization motif of the Alzheimer's amyloid precursor protein by the XII PTB domain. EMBO J Oct. 15, 1997;16(20):6141-6150.

Borg JP, Ooi J, Levy E, Margolis B. The phosphotyrosine interaction domains of XII and FE65 bind to distinct sites on the YENPTY motif of amyloid precursor protein. Mol Cell Biol Nov. 1996;16(11):6229-6241.

Guenette SY, Chen J, Jondro PD, Tanzi RE. Association of a novel human FE65-like protein with the cytoplasmic domain of the beta-amyloid precursor protein. Proc Natl Acad Sci U S A Oct. 1, 1996;93(20):10832-10837.

Hata Y, Butz S, Sudhof TC. CASK: a novel dlg/PSD95 homolog with an N-terminal calmodulin-dependent protein kinase domain identified by interaction with neurexins. J Neurosci Apr. 15, 1996;16(8):2488-2494.

McLoughlin DM, Miller CC. The interacellular cytoplasmic domain of the Alzheimer's disease amyloid precursor protein interacts with phosphotyrosine-binding domain proteins in the yeast two-hybrid system. FEBS Lett Nov. 18, 1996:397(2-3):197-200.

Duclos F, Koenig M. Comparison of primary structure of a neuron-specific protein, XII, between human and mouse. Mamm Genome Jan. 1995;6(1):57-58.

Fiore F, Zambrano N, Minopoli G, Donini V, Duilio A, Russo T. The regions of the Fe65 protein homologous to the phosphotyrosine interaction/phosphotyrosine binding domain of Shc bind the intracellular domain of the Alzheimer's amyloid precursor protein. J Biol Chem Dec. 29, 1995;270(52):30853-30856.

Hollenberg SM, Sternglanz R, Cheng PF, Weintraub H. Identification of a new family of tissue-specific basic helix-loop-helix proteins with a two-hybrid system. Mol Cell Biol Jul. 1995;15(7):3813-3822.

Mu FT, Callaghan JM, Steele-Mortimer O, Stenmark H, Parton RG, Campbell PL, McCluskey J, Yeo JP, Tock EP, Toh BH. EEA1, an early endosome-associated protein. EEA1 is a conserved alpha-helical peripheral membrane protein flanked by cysteine "fingers" and contains a calmodulin-binding IQ motif. J Biol Chem Jun. 2, 1995;270(22):13503-13511.

Kistner U, Wenzel BM, Veh RW, Cases-Langhoff C, Garner AM, Appeltauer U, Voss B, Gundelfinger ED, Garner CC. SAP90, a rat presynaptic protein related to the product of the Drosophila tumor suppressor gene dlg-A. J Biol Chem Mar. 5, 1993;268(7):4580-4583.

Cho KO, Hunt CA, Kennedy MB. The rat brain postsynaptic density fraction contains a homolog of the Drosophila discs-large tumor suppressor protein. Neuron Nov. 1992;9(5):929-942.

Wada I, Rindress D, Cameron PH, Ou WJ, Doherty JJ 2nd, Louvard D, Bell AW, Dignard D, Thomas DY, Bergeron JJ. SSR alpha and associated calnexin are major calcium binding proteins of the endoplasmic reticulum membrane, J Biol Chem Oct. 15, 1991;266(29):19599-19610.

Stringer KF, Ingles CJ, Greenblatt J. Direct and selective binding of an acidic transcriptional activation domain to the TATA-box factor TFIID, Nature Jun. 28, 1990; 345(6278):783-786.

Bloom GS, Brashear TA. A novel 58-kDa protein associates with the Golgi apparatus and microtubules. J Biol Chem Sep. 25, 1989;264(27):16083-16092.

Fields S, Song O. A novel genetic system to detect protein-protein interactions. Nature Jul. 20, 1989;340(6230):245-246.

Lillie JW, Green MR. Transcription activation by the adenovirus E1a protein. Nature Mar. 2, 1989;338(6210):39-44.

Kitaguchi N, Takahashi Y, Tokushima Y, Shiojiri S, Ito H. Novel precursor of Alzheimer's disease amyloid protein shows protease inhibitory activity. Nature Feb. 11, 1988;331(6156):530-532.

Sadowski I, Ma J, Triezenberg S, Ptashne M. GAL4-VP16 is an unusually potent transcriptional activator. Nature Oct. 6, 1988;335(6190):563-564.

Tanzi RE, McClatchey AI, Lamperti ED, Villa-Komaroff L, Gusella JF, Neve RL. Protease inhibitor domain encoded by an amyloid protein precursor mRNA associated with Alzheimer's disease. Nature Feb. 11, 1988;331(6156):528-530.

Kang J, Lemaire HG, Unterbeck A, Salbaum JM, Masters CL, Grzeschik KH, Multhaup G, Beyreuther K, Muller-Hill B. The precursor of Alzheimer's disease amyloid A4 protein resembles a cell-surface receptor. Nature Feb. 19-25, 1987;325(6106):733-736.

Hurstel S, Granger-Schnarr M, Daune M, Schnarr M. In vitro binding of LexA repressor to DNA: evidence for the involvement of the amino-terminal domain. EMBO J Apr. 1986;5(4):793-798.

Giniger E, Varnum SM, Ptashne M. Specific DNA binding of GAL4, a positive regulatory protein of yeast. Cell Apr. 1985;40(4):767-774.

Masters CL, Multhaup G, Simms G, Pottgiesser J, Martins RN, Beyreuther K. Neuronal origin of a cerebral amyloid: neurofibrillary tangles of Alzheimer's disease contain the same protein as the amyloid of plaque cores and blood vessels. EMBO J Nov. 1985;4(11):2757-2763.

Glenner GG, Wong CW. Alzheimer's disease and Down's syndrome: sharing of a unique cerebrovascular amyloid fibril protein. Biochem Biophys Res Commun Aug. 16, 1984;122(3):1131-1135.

Biederer et al. (2002) "Regulation of APP-dependent transcription complexes by Mint/XIIs: differential functions of Mint isoforms", The Journal of Neuroscience 22: 7340-7351.

Okamoto et al. (2001) "Amyloid precursor protein associates independently and collaboratively with PTB and PDZ domains of Mint on vesicles and at cell membrane", Neuroscience 104: 653-665.

Südhof et al. (1998) "Mint 3: A ubiquitous mint isoform that does not bind to munc18-1 or -2", European Journal of Cell Biology 77: 161-165.

1. Gal4
2. GV
3. APP-GV
4. APP*-GV
5. APP-GV
6. APPγ-GV
7. APPγ*-GV
8. APP_{ICF}-Gal4
9. APP_{ICF}*-Gal4

* NPTY→NATA mutation    Membrane

FIGURE 13A

```
atgaaccact tggagggctc cgcggaggtg gaggtggccg acgaggcgcc    50
aggaggggag gtgaacgagt ccgtggaggc cgacctggag caccccgagg   100
tggaggaaga gcagcagccg tcgccccgc cgcccgcagg tcacgcaccc    150
gaggaccacc gcgcgcatcc ggcgccgccg ccgccgccac caccgcagga   200
ggaggaggag gagcgcggcg agtgcctggc tcgctcggcc agcaccgaga   250
gcggcttcca caaccacacg gacaccgctg agggcgacgt gctcgccgcg   300
gcccgagacg gctacgaggc ggagcgcgcg caggacgccg acgatgagag   350
cgcctacgcc gtgcagtacc ggcccgaggc cgaggagtac acggagcagg   400
cggaggccga gcacgccgag gcggcgcagc ggcgcgcgct gcccaaccac   450
ctgcacttcc actcgctgga gcacgaggaa gccatgaacg ccgcctactc   500
gggctatgtc tacacgcacc ggctcttcca ccgcgccgag gacgagccct   550
acgccgagcc ctacgccgac tacggcggcc tccaggagca cgtgtacgag   600
gagatcgggg acgcgcctga gctggagcg cgcgacggcc tgcggctcta    650
tgagcgggag cgcgacgagg cggccgccta ccgccaggag gccctaggcg   700
cgcggctgca ccactacgac gagcgctccg acggcgagtc cgacagcccc   750
gagaaggagg cggagttcgc gccctacccg cgcatggaca gttatgagca   800
ggaagaggac atcgaccaga tcgtggccga ggtcaagcag agcatgagct   850
cgcagagcct cgacaaggcg gccgaagaca tgcccgaggc ggagcaggac   900
ctggagcgcg ccccgacccc gggaggggga caccccgaca gccctgggct   950
gccagcacct gccgggcagc agcagcgagt tgtgggaacc ccgggaggca  1000
gcgaggttgg tcagcggtac agcaaggaaa agagggatgc catctcgctg  1050
gccatcaagg acatcaagga ggccatcgaa gaagtgaaaa ccaggaccat  1100
ccgttcgcct tacaccccg acgaacccaa agagcccatc tgggtcatgc    1150
gccaggacat tagccccaca agggactgtg acgaccagag gcccgtggac  1200
ggagattctc cgtctcctgg cagttcctca cccctgggtg ctgagtcatc  1250
aatcacaccc cttcatcccg gtgacccac ggaagcctcc actaataaag   1300
agtcaagaaa aagcttggct tcattcccaa cctacgttga agttcctgga  1350
ccctgcgacc ctgaagactt gatcgatgga attattttg ctgccaatta   1400
ccttggttcc actcagctac tctcagacaa aactccctcc aaaaacgtgc  1450
gcatgatgca ggcccaggaa gcagtaagcc ggatcaagac ggcccagaaa  1500
ttagccaaaa gcaggaagaa ggctcctgaa ggcgaatctc agccaatgac  1550
tgaggtggac ctcttcatct ccaccagag gatcaaagtg ttgaatgcag   1600
atacacagga gcctatgatg gaccaccctc tgaggaccat ttcctacatc  1650
gcagacattg gaacatcgt cgtgctgatg gcccgcaggc ggatgccccg   1700
ctccaactcc caggagaatg tggaggcctc tcacccatcc caggatgcaa  1750
aacggcagta caagatgatc tgtcatgtct ttgagtctga ggacgcccag  1800
ctgatcgcac agtccatcgg gcaggcc tc agcgttgcat accaggagtt   1850
cctcagggcc aacgggatta acccagaaga cctgagccag aaggagtaca  1900
```

FIGURE 13B

```
gcgacctgct caacacccag gacatgtaca acgatgacct gatccacttc 1950
tccaagtcgg aaaactgcaa agatgtcttc atagagaagc agaaaggaga 2000
aatcctggga gttgtgattg tggagtctgg ctggggatcc attctgccaa 2050
ccgtgatcat tgccaacatg atgcacggag gccccgccga gaagtcgggg 2100
aagctgaaca tcggggacca gatcatgtcc attaacggca ccagcctggt 2150
gggcctgccc ctgtccacct gccagagcat cattaagggc ttaaagaacc 2200
agtcccgcgt gaagctgaac atcgtgaggt gcccccagt gaccacagtg 2250
ctaattagga ggccggacct tcgctaccag ctgggtttca gcgtgcagaa 2300
tggaattatc tgtagcctca tgagagggg aatagctgag agaggaggtg 2350
tccgcgtggg acatcggatc attgaaatca acggccagag tgtcgtagcc 2400
acaccacacg agaagatcgt ccacatactc tccaatgctg ttggggagat 2450
ccacatgaag acaatgccag cagccatgta cagactgctg acagcccagg 2500
agcagcccgt ttacatctga                                 2520
```

FIGURE 13C

```
atgaaccact tggagggctc cgcggaggtg gaggtggccg acgaggcgcc   50
aggaggggag gtgaacgagt ccgtggaggc cgacctggag caccccgagg  100
tggaggaaga gcagcagccg tcgcccccgc cgcccgcagg tcacgcaccc  150
gaggaccacc gcgcgcatcc ggcgccgccg ccgccgccac caccgcagga  200
ggaggaggag gagcgcggcg agtgcctggc tcgctcggcc agcaccgaga  250
gcggcttcca caaccacacg acaccgctg agggcgacgt gctcgccgcg  300
gcccgagacg gctacgaggc ggagcgcgcg caggacgccg acgatgagag  350
cgcctacgcc gtgcagtacc ggcccgaggc cgaggagtac acggagcagg  400
cggaggccga gcacgccgag gcggcgcagc ggcgcgcgct gcccaaccac  450
ctgcacttcc actcgctgga gcacgaggaa gccatgaacg ccgcctactc  500
gggctatgtc tacacgcacc ggctcttcca ccgcgccgag gacgagccct  550
acgccgagcc ctacgccgac tacggcggcc tccaggagca cgtgtacgag  600
gagatcgggg acgcgcctga gctggaggcg cgcgacggcc tgcggctcta  650
tgagcgggag cgcgacgagg cggccgccta ccgccaggag gccctaggcg  700
cgcggctgca ccactacgac gagcgctccg acggcgagtc cgacagcccc  750
gagaaggagg cggagttcgc gccctacccg cgcatggaca gttatgagca  800
ggaagaggac atcgaccaga tcgtggccga ggtcaagcag agcatgagct  850
cgcagagcct cgacaaggcg gccgaagaca tgcccgaggc ggagcaggac  900
ctggagcgcg ccccgacccc gggaggggga caccccgaca gccctgggct  950
gccagcacct gccggcagc agcagcgagt tgtgggaacc ccgggaggca 1000
gcgaggttgg tcagcggtac agcaaggaaa agagggatgc catctcgctg 1050
gccatcaagg acatcaagga ggccatcgaa gaagtgaaaa ccaggaccat 1100
ccgttcgcct tacacccccg acgaacccaa agagcccatc tgggtcatgc 1150
gccaggacat tagccccaca agggactgtg acgaccagag gcccgtggac 1200
ggagattctc cgtctcctgg cagttcctca ccctgggtg ctgagtcatc 1250
aatcacaccc cttcatcccg gtgaccccac ggaagcctcc actaataaag 1300
agtcaagaaa aagcttggct tcattcccaa cctacgttga gttcctgga  1350
ccctgcgacc ctgaagactt gatcgatgga attattttg ctgccaatta  1400
ccttggttcc actcagctac tctcagacaa aactccctcc aaaaacgtgc 1450
gcatgatgca ggcccaggaa gcagtaagcc ggatcaagac ggcccagaaa 1500
ttagccaaaa gcaggaagaa ggctcctgaa ggcgaatctc agccaatgac 1550
tgaggtggac ctcttcatct ccacccagag gatcaaagtg ttgaatgcag 1600
atacacagga gcctatgatg gaccaccctc tgaggaccat ttcctacatc 1650
gcagacattg ggaacatcgt cgtgctgatg gcccgcaggc ggatgccccg 1700
ctccaactcc caggagaatg tggaggcctc tcacccatcc aggatgcaa  1750
aacgcagta caagatgatc tgtcatgtct ttgagtctga ggacgcccag 1800
ctgatcgcac agtccatcgg gcaggccttc agcgttgcat accaggagtt 1850
cctcagggcc aacgggatta acccagaaga cctgagccag aaggagtaca 1900
```

FIGURE 13D

```
gcgacctgct caacacccag gacatgtaca acgatgacct gatccacttc 1950
tccaagtcgg aaaactgcaa agatgtcttc atagagaagc agaaaggaga 2000
aatcctggCG gCCgtgattg tggagtctgg ctggggatcc attctgccaa 2050
ccgtgatcat tgccaacatg atgcacggag gccccgccga gaagtcgggg 2100
aagctgaaca tcggggacca gatcatgtcc attaacggca ccagcctggt 2150
gggcctgccc ctgtccacct gccagagcat cattaagggc ttaaagaacc 2200
agtcccgcgt gaagctgaac atcgtgaggt gcccccagt gaccacagtg 2250
ctaattagga ggccggacct tcgctaccag ctgggtttca gcgtgcagaa 2300
tggaattatc tgtagcctca tgagagggg aatagctgag agaggaggtg 2350
tccgcgtggg acatcggatc attgaaatca acggccagag tgtcgtagcc 2400
acaccacacg agaagatcgt ccacatactc tccaatgctg ttggggagat 2450
ccacatgaag acaatgccag cagccatgta cagactgctg acagcccagg 2500
agcagcccgt ttacatctga                                  2520
```

FIGURE 13E

```
atgaaccact tggagggctc cgcggaggtg gaggtggccg acgaggcgcc  50
aggaggggag gtgaacgagt ccgtggaggc cgacctggag cacccgagg  100
tggaggaaga gcagcagccg tcgccccgc cgcccgcagg tcacgcaccc  150
gaggaccacc gcgcgcatcc ggcgccgccg ccgccgccac caccgcagga  200
ggaggaggag gagcgcggcg agtgcctggc tcgctcggcc agcaccgaga  250
gcggcttcca caaccacacg gacaccgctg agggcgacgt gctcgccgcg  300
gcccgagacg gctacgaggc ggagcgcgcg caggacgccg acgatgagag  350
cgcctacgcc gtgcagtacc ggcccgaggc cgaggagtac acggagcagg  400
cggaggccga gcacgccgag gcggcgcagc ggcgcgcgct gcccaaccac  450
ctgcacttcc actcgctgga gcacgaggaa gccatgaacg ccgcctactc  500
gggctatgtc tacacgcacc ggctcttcca ccgcgccgag gacgagccct  550
acgccgagcc ctacgccgac tacggcggcc tccaggagca cgtgtacgag  600
gagatcgggg acgcgcctga gctggaggcg cgcgacggcc tgcggctcta  650
tgagcgggag cgcgacgagg cggccgccta ccgccaggag gccctaggcg  700
cgcggctgca ccactacgac gagcgctccg acggcgagtc cgacagcccc  750
gagaaggagg cggagttcgc gccctacccg cgcatggaca gttatgagca  800
ggaagaggac atcgaccaga tcgtggccga ggtcaagcag agcatgagct  850
cgcagagcct cgacaaggcg gccgaagaca tgcccgaggc ggagcaggac  900
ctggagcgcg ccccgacccc gggaggggga caccccgaca gccctgggct  950
gccagcacct gccgggcagc agcagcgagt tgtgggaacc ccgggaggca 1000
gcgaggttgg tcagcggtac agcaaggaaa agagggatgc catctcgctg 1050
gccatcaagg acatcaagga ggccatcgaa gaagtgaaaa ccaggaccat 1100
ccgttcgcct tacacccccg acgaacccaa agagcccatc tgggtcatgc 1150
gccaggacat tagccccaca agggactgtg acgaccagag gcccgtggac 1200
ggagattctc cgtctcctgg cagttcctca ccctgggtg ctgagtcatc 1250
aatcacaccc cttcatcccg gtgaccccac ggaagcctcc actaataaag 1300
agtcaagaaa aagcttggct tcattcccaa cctacgttga agttcctgga 1350
ccctgcgacc ctgaagactt gatcgatgga attattttg ctgccaatta 1400
ccttggttcc actcagctac tctcagacaa aactccctcc aaaaacgtgc 1450
gcatgatgca ggcccaggaa gcagtaagcc ggatcaagac ggcccagaaa 1500
ttagccaaaa gcaggaagaa ggctcctgaa ggcgaatctc agccaatgac 1550
tgaggtggac ctcttcatct ccacccagag gatcaaagtg ttgaatgcag 1600
atacacagga gcctatgatg gaccaccctc tgaggaccat ttcctacatc 1650
gcagacattg gaacatcgt cgtgctgatg gcccgcaggc ggatgccccg 1700
ctccaactcc caggagaatg tggaggcctc tcacccatcc caggatgcaa 1750
aacggcagta caagatgatc tgtcatgtct ttgagtctga ggacgcccag 1800
ctgatcgcac agtccatcgg gcaggccttc agcgttgcat accaggagtt 1850
cctcagggcc aacgggatta acccagaaga cctgagccag aaggagtaca 1900
```

FIGURE 13F

```
gcgacctgct caacacccag gacatgtaca acgatgacct gatccacttc 1950
tccaagtcgg aaaactgcaa agatgtctAG                        1980
```

FIGURE 13G

```
ATGGAGCAGA AGCTGATCAG CGAGGAGGAC CTGAACGGAA TTCAGATCTG 50
GTACccctgc gaccctgaag acttgatcga tggaattatt tttgctgcca 100
attaccttgg ttccactcag ctactctcag acaaaactcc ctccaaaaac 150
gtgcgcatga tgcaggccca ggaagcagta agccggatca agacggccca 200
gaaattagcc aaaagcagga agaaggctcc tgaaggcgaa tctcagccaa 250
tgactgaggt ggacctcttc atctccaccc agaggatcaa agtgttgaat 300
gcagatacac aggagcctat gatggaccac cctctgagga ccatttccta 350
catcgcagac attgggaaca tcgtcgtgct gatggcccgc aggcggatgc 400
cccgctccaa ctcccaggag aatgtggagg cctctcaccc atcccaggat 450
gcaaaacggc agtacaagat gatctgtcat gtctttgagt ctgaggacgc 500
ccagctgatc gcacagtcca tcgggcaggc cttcagcgtt gcataccagg 550
agttcctcag ggccaacggg attaacccag aagacctgag ccagaaggag 600
tacagcgacc tgctcaacac ccaggacatg tacaacgatg acctgatcca 650
cttctccaag tcggaaaact gcaaagatgt cttcatagag aagcagaaag 700
gagaaatcct gggagttgtg attgtggagt ctggctgggg atccattctg 750
ccaaccgtga tcattgccaa catgatgcac ggaggccccg ccgagaagtc 800
ggggaagctg aacatcgggg accagatcat gtccattaac ggcaccagcc 850
tggtgggcct gccctgtcc acctgccaga gcatcattaa gggcttaaag 900
aaccagtccc gcgtgaagct gaacatcgtg aggtgccccc cagtgaccac 950
agtgctaatt aggaggccgg accttcgcta ccagctgggt ttcagcgtgc 1000
agaatggaat tatctgtagc ctcatgagag ggggaatagc tgagagagga 1050
ggtgtccgcg tgggacatcg gatcattgaa atcaacggcc agagtgtcgt 1100
agccacacca cacgagaaga tcgtccacat actctccaat gctgttgggg 1150
agatccacat gaagacaatg ccagcagcca tgtacagact gctgacagcc 1200
caggagcagc ccgtttacat ctga          1224
```

FIGURE 13H

```
atggcccacc gcaagcgcca gagcactgca agcagcatgt tggaccacag  50
ggcccggcca ggtcctatcc cccatgacca ggagcctgag aatgaggata 100
cagaactgcc tctggagagc tatgtaccca caggcctgga gctaggcact 150
ctgagaccag acagccccac gcctgaggaa caggagtgcc acaaccatag 200
ccctgatggg gactccagct ctgactatgt gaacaacacg tctgaggagg 250
aggactatga cgagggcctc cctgaggagg aggaaggtgt cacctactac 300
atccgctatt gtcctgagga tgacagctac ctggagggca tggactgtaa 350
tggggaggag tacctagccc atggtgcaca tcctgtggac actgatgagt 400
gtcaggaggc ggtagaggac tggacggact cagtgggtcc tcatactcat 450
agccacgggg ctgaaaacag ccaagagtat ccagacagcc acctgcctat 500
cccagaggat gaccctactg tcctggaggt ccatgaccag gaagaagatg 550
gccactactg tcccagcaag gagagctacc aggactatta tcccccagag 600
accaatggga acacgggtgg cgcttctccc tatcgcatga ggcgtgggga 650
tggggaccta gaggagcagg aggaagacat cgaccagata gtggctgaga 700
tcaagatgag cctgagcatg accagtatta ccagtgccag tgaggccagc 750
cctgagcaca tgcctgagct ggaccctggg gactccactg aggcctgttc 800
acccagtgac actggccgtg gacccagtag gcaagaagcg aggcccaagt 850
cgctgaacct tccccctgag gttaagcact ccggagaccc ccaaagagga 900
ctcaagacca agaccaggac cccagaggag aggccaaagt ggccccaaga 950
gcaggtttgc aatggcttgg aacagccgag gaagcagcag cgctctgatc 1000
tcaatggacc cactgacaat aacaacatcc cagagacaaa gaaggtggcc 1050
tcgtttccaa gctttgtagc tgttccaggg ccctgtgagc cagaagacct 1100
catcgatggc atcatctttg cagccaacta cctgggctcc acccagctgc 1150
tctctgagcg caaccccctcc aaaaacatcc gaatgatgca agctcaagaa 1200
gctgtcagca gggtcaagag gatgcagaag gctgctaaga tcaagaaaaa 1250
agcgaattct gagggtgatg ctcagacact gacagaagta gacctcttca 1300
tttctaccca gaggatcaaa gtcttaaacg ctgacacaca ggaaaccatg 1350
atggaccatg ccttgcgcac catctcctac attgcagaca ttgggaacat 1400
cgtggttctg atggccaggc ccgcatgcc caggtcagcc tctcaggact 1450
gcatcgagac cacgcctggg gcccaggaag ggaagaagca gtacaagatg 1500
atctgtcacg tgttcgagtc agaggatgcc cagctgatag cccagtcaat 1550
tgggcaggcc ttcagtgtgg cctaccagga gttcctgagg gccaacggca 1600
tcaaccctga ggacctgagc cagaaggaat acagtgatat cataaatacc 1650
caggagatgt ataatgatga ccttatccac ttctcaaact cggagaactg 1700
caaggagctg cagctggaga agcacaaggg tgagattttg ggtgtggtgg 1750
tcgtggagtc aggctgggc tccatcctgc ccactgtgat cctggcgaac 1800
atgatgaacg gcggcccagc agctcgctcg gggaagctga gcattggcga 1850
ccagatcatg tccatcaatg gcaccagcct ggtggggctg ccctcgcta  1900
```

FIGURE 13I

```
cctgccaggg tatcatcaag ggcctgaaga accaaacaca ggtaaagctc 1950
aacatcgtca gctgtccccc agtcaccaca gtcctcatca aacgtccaga 2000
tctcaagtac cagctgggtt tcagcgtgca aaatggaatc atttgcagcc 2050
tcatgagagg gggtattgca gagcgaggtg gtgtccgagt cggccaccgt 2100
atcatcgaga tcaacggaca gagtgtggta gccacagccc acgagaagat 2150
agtccaggct ctgtctaact cagttggaga gattcacatg aagaccatgc 2200
ctgcagccat gttcaggctc ctcacaggcc aggagacacc gctgtacatc 2250
tag                                                   2253
```

FIGURE 13J

```
atggcccacc gcaagcgcca gagcactgca agcagcatgt tggaccacag 50
ggcccggcca ggtcctatcc cccatgacca ggagcctgag aatgaggata 100
cagaactgcc tctggagagc tatgtaccca caggcctgga gctaggcact 150
ctgagaccag acagccccac gcctgaggaa caggagtgcc acaaccatag 200
ccctgatggg gactccagct ctgactatgt gaacaacacg tctgaggagg 250
aggactatga cgagggcctc cctgaggagg aggaaggtgt cacctactac 300
atccgctatt gtcctgagga tgacagctac ctggagggca tggactgtaa 350
tggggaggag tacctagccc atggtgcaca tcctgtggac actgatgagt 400
gtcaggaggc ggtagaggac tggacggact cagtgggtcc tcatactcat 450
agccacgggg ctgaaaacag ccaagagtat ccagacagcc acctgcctat 500
cccagaggat gaccctactg tcctggaggt ccatgaccag gaagaagatg 550
gccactactg tcccagcaag gagagctacc aggactatta tcccccagag 600
accaatggga acacgggtgg cgcttctccc tatcgcatga ggcgtgggga 650
tggggaccta gaggagcagg aggaagacat cgaccagata gtggctgaga 700
tcaagatgag cctgagcatg accagtatta ccagtgccag tgaggccagc 750
cctgagcaca tgcctgagct ggaccctggg gactccactg aggcctgttc 800
acccagtgac actggccgtg gacccagtag gcaagaagcg aggcccaagt 850
cgctgaacct tcccctgag gttaagcact ccggagaccc ccaaagagga 900
ctcaagacca agaccaggac cccagaggag aggccaaagt ggccccaaga 950
gcaggtttgc aatggcttgg aacagccgag gaagcagcag cgctctgatc 1000
tcaatggacc cactgacaat aacaacatcc cagagacaaa gaaggtggcc 1050
tcgtttccaa gctttgtagc tgttccaggg ccctgtgagc cagaagacct 1100
catcgatggc atcatctttg cagccaacta cctgggctcc acccagctgc 1150
tctctgagcg caacccctcc aaaaacatcc gaatgatgca agctcaagaa 1200
gctgtcagca gggtcaagag gatgcagaag gctgctaaga tcaagaaaaa 1250
agcgaattct gagggtgatg ctcagacact gacagaagta gacctcttca 1300
tttctaccca gaggatcaaa gtcttaaacg ctgacacaca ggaaaccatg 1350
atggaccatg ccttgcgcac catctcctac attgcagaca ttgggaacat 1400
cgtggttctg atggccaggc gccgcatgcc caggtcagcc tctcaggact 1450
gcatcgagac cacgcctggg gcccaggaag gaagaagca gtacaagatg 1500
atctgtcacg tgttcgagtc agaggatgcc cagctgatag cccagtcaat 1550
tgggcaggcc ttcagtgtgg cctaccagga gttcctgagg ccaacggca 1600
tcaaccctga ggacctgagc cagaaggaat acagtgatat cataaatacc 1650
caggagatgt ataatgatga ccttatccac ttctcaaact cggagaactg 1700
caaggagctg cagctggaga agcacaaggg tgagattttg GCAGCAgtgg 1750
tcgtggagtc aggctgggc tccatcctgc ccactgtgat cctggcgaac 1800
atgatgaacg gcggcccagc agctcgctcg gggaagctga gcattggcga 1850
ccagatcatg tccatcaatg gcaccagcct ggtggggctg cccctcgcta 1900
```

FIGURE 13K

```
cctgccaggg tatcatcaag ggcctgaaga accaaacaca ggtaaagctc 1950
aacatcgtca gctgtccccc agtcaccaca gtcctcatca aacgtccaga 2000
tctcaagtac cagctgggtt tcagcgtgca aaatggaatc atttgcagcc 2050
tcatgagagg gggtattgca gagcgaggtg gtgtccgagt cggccaccgt 2100
atcatcgaga tcaacggaca gagtgtggta gccacagccc acgagaagat 2150
agtccaggct ctgtctaact cagttggaga gattcacatg aagaccatgc 2200
ctgcagccat gttcaggctc ctcacaggcc aggagacacc gctgtacatc 2250
tag                                                   2253
```

FIGURE 13L

```
atggcccacc gcaagcgcca gagcactgca agcagcatgt tggaccacag 50
ggcccggcca ggtcctatcc cccatgacca ggagcctgag aatgaggata 100
cagaactgcc tctggagagc tatgtaccca caggcctgga gctaggcact 150
ctgagaccag acagccccac gcctgaggaa caggagtgcc acaaccatag 200
ccctgatggg gactccagct ctgactatgt gaacaacacg tctgaggagg 250
aggactatga cgagggcctc cctgaggagg aggaaggtgt cacctactac 300
atccgctatt gtcctgagga tgacagctac ctggagggca tggactgtaa 350
tggggaggag tacctagccc atggtgcaca tcctgtggac actgatgagt 400
gtcaggaggc ggtagaggac tggacggact cagtgggtcc tcatactcat 450
agccacgggg ctgaaaacag ccaagagtat ccagacagcc acctgcctat 500
cccagaggat gaccctactg tcctggaggt ccatgaccag gaagaagatg 550
gccactactg tcccagcaag gagagctacc aggactatta tcccccagag 600
accaatggga acacgggtgg cgcttctccc tatcgcatga ggcgtgggga 650
tggggaccta gaggagcagg aggaagacat cgaccagata gtggctgaga 700
tcaagatgag cctgagcatg accagtatta ccagtgccag tgaggccagc 750
cctgagcaca tgcctgagct ggaccctggg gactccactg aggcctgttc 800
acccagtgac actggccgtg gacccagtag gcaagaagcg aggcccaagt 850
cgctgaacct tcccctgag gttaagcact ccggagaccc ccaaagagga 900
ctcaagacca agaccaggac cccagaggag aggccaaagt ggccccaaga 950
gcaggtttgc aatggcttgg aacagccgag gaagcagcag cgctctgatc 1000
tcaatggacc cactgacaat aacaacatcc cagagacaaa gaaggtggcc 1050
tcgtttccaa gctttgtagc tgttccaggg ccctgtgagc cagaagacct 1100
catcgatggc atcatctttg cagccaacta cctgggctcc acccagctgc 1150
tctctgagcg caacccctcc aaaaacatcc gaatgatgca agctcaagaa 1200
gctgtcagca gggtcaagag gatgcagaag gctgctaaga tcaagaaaaa 1250
agcgaattct gagggtgatg ctcagacact gacagaagta gacctcttca 1300
tttctaccca gaggatcaaa gtcttaaacg ctgacacaca ggaaaccatg 1350
atggaccatg ccttgcgcac catctcctac attgcagaca ttgggaacat 1400
cgtggttctg atggccaggc ccgcatgcc caggtcagcc tctcaggact 1450
gcatcgagac cacgcctggg gcccaggaag ggaagaagca gtacaagatg 1500
atctgtcacg tgttcgagtc agaggatgcc cagctgatag cccagtcaat 1550
tgggcaggcc ttcagtgtgg cctaccagga gttcctgagg gccaacggca 1600
tcaaccctga ggacctgagc cagaaggaat acagtgatat cataaatacc 1650
caggagatgt ataatgatga ccttatccac ttctcaaact cggagaactg 1700
caaggagctC TAG                                         1713
```

FIGURE 13M

```
ATGGAGCAGA AGCTGATCAG CGAGGAGGAC CTGAACGGAA TTCAGATCTG  50
GTACccctgt gagccagaag acctcatcga tggcatcatc tttgcagcca 100
actacctggg ctccacccag ctgctctctg agcgcaaccc ctccaaaaac 150
atccgaatga tgcaagctca agaagctgtc agcagggtca agaggatgca 200
gaaggctgct aagatcaaga aaaagcgaa ttctgagggt gatgctcaga 250
cactgacaga agtagacctc ttcatttcta cccagaggat caaagtctta 300
aacgctgaca cacaggaaac catgatggac catgccttgc gcaccatctc 350
ctacattgca gacattggga acatcgtggt tctgatggcc aggcgccgca 400
tgcccaggtc agcctctcag gactgcatcg agaccacgcc tggggcccag 450
gaagggaaga agcagtacaa gatgatctgt cacgtgttcg agtcagagga 500
tgcccagctg atagcccagt caattgggca ggccttcagt gtggcctacc 550
aggagttcct gagggccaac ggcatcaacc ctgaggacct gagccagaag 600
gaatacagtg atatcataaa tacccaggag atgtataatg atgaccttat 650
ccacttctca aactcggaga actgcaagga gctgcagctg gagaagcaca 700
agggtgagat tttggggtgtg gtggtcgtgg agtcaggctg gggctccatc 750
ctgcccactg tgatcctggc gaacatgatg aacggcggcc agcagctcg 800
ctcggggaag ctgagcattg gcgaccagat catgtccatc aatggcacca 850
gcctggtggg gctgccctc gctacctgcc agggtatcat caagggcctg 900
aagaaccaaa cacaggtaaa gctcaacatc gtcagctgtc cccagtcac 950
cacagtcctc atcaaacgtc cagatctcaa gtaccagctg ggtttcagcg 1000
tgcaaaatgg aatcatttgc agcctcatga gaggggtat tgcagagcga 1050
ggtggtgtcc gagtcggcca ccgtatcatc gagatcaacg gacagagtgt 1100
ggtagccaca gcccacgaga agatagtcca ggctctgtct aactcagttg 1150
gagagattca catgaagacc atgcctgcag ccatgttcag gctcctcaca 1200
ggccaggaga caccgctgta catctag           1227
```

FIGURE 13N

| | | | | | | | | | | | | | | |
|---|---|---|---|---|---|---|---|---|---|---|---|---|---|---|
|Met|Asn|His|Leu|Glu|Gly|Ser|Ala|Glu|Val|Glu|Val|Ala|Asp|Glu|
|1| | | |5| | | |10| | | | |15| |
|Ala|Pro|Gly|Gly|Glu|Val|Asn|Glu|Ser|Val|Glu|Ala|Asp|Leu|Glu|
| | | | |20| | | |25| | | | |30| |
|His|Pro|Glu|Val|Glu|Glu|Glu|Gln|Gln|Pro|Ser|Pro|Pro|Pro|Pro|
| | | | |35| | | |40| | | | |45| |
|Ala|Gly|His|Ala|Pro|Glu|Asp|His|Arg|Ala|His|Pro|Ala|Pro|Pro|
| | | | |50| | | |55| | | | |60| |
|Pro|Pro|Pro|Pro|Pro|Gln|Glu|Glu|Glu|Glu|Arg|Gly|Glu|Cys| |
| | | | |65| | | |70| | | | |75| |
|Leu|Ala|Arg|Ser|Ala|Ser|Thr|Glu|Ser|Gly|Phe|His|Asn|His|Thr|
| | | | |80| | | |85| | | | |90| |
|Asp|Thr|Ala|Glu|Gly|Asp|Val|Leu|Ala|Ala|Ala|Arg|Asp|Gly|Tyr|
| | | | |95| | | |100| | | | |105| |
|Glu|Ala|Glu|Arg|Ala|Gln|Asp|Ala|Asp|Asp|Glu|Ser|Ala|Tyr|Ala|
| | | | |110| | | |115| | | | |120| |
|Val|Gln|Tyr|Arg|Pro|Glu|Ala|Glu|Glu|Tyr|Thr|Glu|Gln|Ala|Glu|
| | | | |125| | | |130| | | | |135| |
|Ala|Glu|His|Ala|Glu|Ala|Ala|Gln|Arg|Arg|Ala|Leu|Pro|Asn|His|
| | | | |140| | | |145| | | | |150| |
|Leu|His|Phe|His|Ser|Leu|Glu|His|Glu|Glu|Ala|Met|Asn|Ala|Ala|
| | | | |155| | | |160| | | | |165| |
|Tyr|Ser|Gly|Tyr|Val|Tyr|Thr|His|Arg|Leu|Phe|His|Arg|Ala|Glu|
| | | | |170| | | |175| | | | |180| |
|Asp|Glu|Pro|Tyr|Ala|Glu|Pro|Tyr|Ala|Asp|Tyr|Gly|Gly|Leu|Gln|
| | | | |185| | | |190| | | | |195| |
|Glu|His|Val|Tyr|Glu|Glu|Ile|Gly|Asp|Ala|Pro|Glu|Leu|Glu|Ala|
| | | | |200| | | |205| | | | |210| |
|Arg|Asp|Gly|Leu|Arg|Leu|Tyr|Glu|Arg|Glu|Arg|Asp|Glu|Ala|Ala|
| | | | |215| | | |220| | | | |225| |
|Ala|Tyr|Arg|Gln|Glu|Ala|Leu|Gly|Ala|Arg|Leu|His|His|Tyr|Asp|
| | | | |230| | | |235| | | | |240| |
|Glu|Arg|Ser|Asp|Gly|Glu|Ser|Asp|Ser|Pro|Glu|Lys|Glu|Ala|Glu|
| | | | |245| | | |250| | | | |255| |
|Phe|Ala|Pro|Tyr|Pro|Arg|Met|Asp|Ser|Tyr|Glu|Gln|Glu|Glu|Asp|
| | | | |260| | | |265| | | | |270| |
|Ile|Asp|Gln|Ile|Val|Ala|Glu|Val|Lys|Gln|Ser|Met|Ser|Ser|Gln|
| | | | |275| | | |280| | | | |285| |

FIGURE 13O

```
Ser Leu Asp Lys Ala Ala Glu Asp Met Pro Glu Ala Glu Gln Asp
            290             295             300
Leu Glu Arg Ala Pro Thr Pro Gly Gly Gly His Pro Asp Ser Pro
            305             310             315
Gly Leu Pro Ala Pro Ala Gly Gln Gln Gln Arg Val Val Gly Thr
            320             325             330
Pro Gly Gly Ser Glu Val Gly Gln Arg Tyr Ser Lys Glu Lys Arg
            335             340             345
Asp Ala Ile Ser Leu Ala Ile Lys Asp Ile Lys Glu Ala Ile Glu
            350             355             360
Glu Val Lys Thr Arg Thr Ile Arg Ser Pro Tyr Thr Pro Asp Glu
            365             370             375
Pro Lys Glu Pro Ile Trp Val Met Arg Gln Asp Ile Ser Pro Thr
            380             385             390
Arg Asp Cys Asp Asp Gln Arg Pro Val Asp Gly Asp Ser Pro Ser
            395             400             405
Pro Gly Ser Ser Ser Pro Leu Gly Ala Glu Ser Ser Ile Thr Pro
            410             415             420
Leu His Pro Gly Asp Pro Thr Glu Ala Ser Thr Asn Lys Glu Ser
            425             430             435
Arg Lys Ser Leu Ala Ser Phe Pro Thr Tyr Val Glu Val Pro Gly
            440             445             450
Pro Cys Asp Pro Glu Asp Leu Ile Asp Gly Ile Ile Phe Ala Ala
            455             460             465
Asn Tyr Leu Gly Ser Thr Gln Leu Leu Ser Asp Lys Thr Pro Ser
            470             475             480
Lys Asn Val Arg Met Met Gln Ala Gln Glu Ala Val Ser Arg Ile
            485             490             495
Lys Thr Ala Gln Lys Leu Ala Lys Ser Arg Lys Lys Ala Pro Glu
            500             505             510
Gly Glu Ser Gln Pro Met Thr Glu Val Asp Leu Phe Ile Ser Thr
            515             520             525
Gln Arg Ile Lys Val Leu Asn Ala Asp Thr Gln Glu Pro Met Met
            530             535             540
Asp His Pro Leu Arg Thr Ile Ser Tyr Ile Ala Asp Ile Gly Asn
            545             550             555
Ile Val Val Leu Met Ala Arg Arg Arg Met Pro Arg Ser Asn Ser
            560             565             570
```

FIGURE 13P

| | | | | | | | | | | | |
|---|---|---|---|---|---|---|---|---|---|---|---|
|Gln|Glu|Asn|Val|Glu 575|Ala|Ser|His|Pro Ser 580|Gln|Asp|Ala|Lys|Arg 585|

Gln Glu Asn Val Glu Ala Ser His Pro Ser Gln Asp Ala Lys Arg
                    575             580              585
Gln Tyr Lys Met Ile Cys His Val Phe Glu Ser Glu Asp Ala Gln
                590              595              600
Leu Ile Ala Gln Ser Ile Gly Gln Ala Phe Ser Val Ala Tyr Gln
                605              610              615
Glu Phe Leu Arg Ala Asn Gly Ile Asn Pro Glu Asp Leu Ser Gln
                620              625              630
Lys Glu Tyr Ser Asp Leu Leu Asn Thr Gln Asp Met Tyr Asn Asp
                635              640              645
Asp Leu Ile His Phe Ser Lys Ser Glu Asn Cys Lys Asp Val Phe
                650              655              660
Ile Glu Lys Gln Lys Gly Glu Ile Leu Gly Val Val Ile Val Glu
                665              670              675
Ser Gly Trp Gly Ser Ile Leu Pro Thr Val Ile Ile Ala Asn Met
                680              685              690
Met His Gly Gly Pro Ala Glu Lys Ser Gly Lys Leu Asn Ile Gly
                695              700              705
Asp Gln Ile Met Ser Ile Asn Gly Thr Ser Leu Val Gly Leu Pro
                710              715              720
Leu Ser Thr Cys Gln Ser Ile Ile Lys Gly Leu Lys Asn Gln Ser
                725              730              735
Arg Val Lys Leu Asn Ile Val Arg Cys Pro Pro Val Thr Thr Val
                740              745              750
Leu Ile Arg Arg Pro Asp Leu Arg Tyr Gln Leu Gly Phe Ser Val
                755              760              765
Gln Asn Gly Ile Ile Cys Ser Leu Met Arg Gly Gly Ile Ala Glu
                770              775              780
Arg Gly Gly Val Arg Val Gly His Arg Ile Ile Glu Ile Asn Gly
                785              790              795
Gln Ser Val Val Ala Thr Pro His Glu Lys Ile Val His Ile Leu
                800              805              810
Ser Asn Ala Val Gly Glu Ile His Met Lys Thr Met Pro Ala Ala
                815              820              825
Met Tyr Arg Leu Leu Thr Ala Gln Glu Gln Pro Val Tyr Ile
                830              835

FIGURE 13Q

```
Met Asn His Leu Glu Gly Ser Ala Glu Val Glu Val Ala Asp Glu
1             5               10              15
Ala Pro Gly Gly Glu Val Asn Glu Ser Val Glu Ala Asp Leu Glu
                20              25              30
His Pro Glu Val Glu Glu Gln Gln Pro Ser Pro Pro Pro Pro
                35              40              45
Ala Gly His Ala Pro Glu Asp His Arg Ala His Pro Ala Pro Pro
                50              55              60
Pro Pro Pro Pro Pro Gln Glu Glu Glu Glu Arg Gly Glu Cys
                65              70              75
Leu Ala Arg Ser Ala Ser Thr Glu Ser Gly Phe His Asn His Thr
                80              85              90
Asp Thr Ala Glu Gly Asp Val Leu Ala Ala Ala Arg Asp Gly Tyr
                95              100             105
Glu Ala Glu Arg Ala Gln Asp Ala Asp Glu Ser Ala Tyr Ala
                110             115             120
Val Gln Tyr Arg Pro Glu Ala Glu Glu Tyr Thr Glu Gln Ala Glu
                125             130             135
Ala Glu His Ala Glu Ala Ala Gln Arg Arg Ala Leu Pro Asn His
                140             145             150
Leu His Phe His Ser Leu Glu His Glu Glu Ala Met Asn Ala Ala
                155             160             165
Tyr Ser Gly Tyr Val Tyr Thr His Arg Leu Phe His Arg Ala Glu
                170             175             180
Asp Glu Pro Tyr Ala Glu Pro Tyr Ala Asp Tyr Gly Gly Leu Gln
                185             190             195
Glu His Val Tyr Glu Glu Ile Gly Asp Ala Pro Glu Leu Glu Ala
                200             205             210
Arg Asp Gly Leu Arg Leu Tyr Glu Arg Glu Arg Asp Glu Ala Ala
                215             220             225
Ala Tyr Arg Gln Glu Ala Leu Gly Ala Arg Leu His His Tyr Asp
                230             235             240
Glu Arg Ser Asp Gly Glu Ser Asp Ser Pro Glu Lys Glu Ala Glu
                245             250             255
Phe Ala Pro Tyr Pro Arg Met Asp Ser Tyr Glu Gln Glu Glu Asp
                260             265             270
Ile Asp Gln Ile Val Ala Glu Val Lys Gln Ser Met Ser Ser Gln
                275             280             285
```

FIGURE 13R

```
Ser Leu Asp Lys Ala Ala Glu Asp Met Pro Glu Ala Glu Gln Asp
            290                 295                 300
Leu Glu Arg Ala Pro Thr Pro Gly Gly His Pro Asp Ser Pro
            305                 310                 315
Gly Leu Pro Ala Pro Ala Gly Gln Gln Gln Arg Val Val Gly Thr
            320                 325                 330
Pro Gly Gly Ser Glu Val Gly Gln Arg Tyr Ser Lys Glu Lys Arg
            335                 340                 345
Asp Ala Ile Ser Leu Ala Ile Lys Asp Ile Lys Glu Ala Ile Glu
            350                 355                 360
Glu Val Lys Thr Arg Thr Ile Arg Ser Pro Tyr Thr Pro Asp Glu
            365                 370                 375
Pro Lys Glu Pro Ile Trp Val Met Arg Gln Asp Ile Ser Pro Thr
            380                 385                 390
Arg Asp Cys Asp Asp Gln Arg Pro Val Asp Gly Asp Ser Pro Ser
            395                 400                 405
Pro Gly Ser Ser Ser Pro Leu Gly Ala Glu Ser Ser Ile Thr Pro
            410                 415                 420
Leu His Pro Gly Asp Pro Thr Glu Ala Ser Thr Asn Lys Glu Ser
            425                 430                 435
Arg Lys Ser Leu Ala Ser Phe Pro Thr Tyr Val Glu Val Pro Gly
            440                 445                 450
Pro Cys Asp Pro Glu Asp Leu Ile Asp Gly Ile Ile Phe Ala Ala
            455                 460                 465
Asn Tyr Leu Gly Ser Thr Gln Leu Leu Ser Asp Lys Thr Pro Ser
            470                 475                 480
Lys Asn Val Arg Met Met Gln Ala Gln Glu Ala Val Ser Arg Ile
            485                 490                 495
Lys Thr Ala Gln Lys Leu Ala Lys Ser Arg Lys Lys Ala Pro Glu
            500                 505                 510
Gly Glu Ser Gln Pro Met Thr Glu Val Asp Leu Phe Ile Ser Thr
            515                 520                 525
Gln Arg Ile Lys Val Leu Asn Ala Asp Thr Gln Glu Pro Met Met
            530                 535                 540
Asp His Pro Leu Arg Thr Ile Ser Tyr Ile Ala Asp Ile Gly Asn
            545                 550                 555
Ile Val Val Leu Met Ala Arg Arg Arg Met Pro Arg Ser Asn Ser
            560                 565                 570
```

FIGURE 13S

```
Gln Glu Asn Val Glu Ala Ser His Pro Ser Gln Asp Ala Lys Arg
            575                 580                 585
Gln Tyr Lys Met Ile Cys His Val Phe Glu Ser Glu Asp Ala Gln
            590                 595                 600
Leu Ile Ala Gln Ser Ile Gly Gln Ala Phe Ser Val Ala Tyr Gln
            605                 610                 615
Glu Phe Leu Arg Ala Asn Gly Ile Asn Pro Glu Asp Leu Ser Gln
            620                 625                 630
Lys Glu Tyr Ser Asp Leu Leu Asn Thr Gln Asp Met Tyr Asn Asp
            635                 640                 645
Asp Leu Ile His Phe Ser Lys Ser Glu Asn Cys Lys Asp Val Phe
            650                 655                 660
Ile Glu Lys Gln Lys Gly Glu Ile Leu Ala Ala Val Ile Val Glu
            665                 670                 675
Ser Gly Trp Gly Ser Ile Leu Pro Thr Val Ile Ile Ala Asn Met
            680                 685                 690
Met His Gly Gly Pro Ala Glu Lys Ser Gly Lys Leu Asn Ile Gly
            695                 700                 705
Asp Gln Ile Met Ser Ile Asn Gly Thr Ser Leu Val Gly Leu Pro
            710                 715                 720
Leu Ser Thr Cys Gln Ser Ile Ile Lys Gly Leu Lys Asn Gln Ser
            725                 730                 735
Arg Val Lys Leu Asn Ile Val Arg Cys Pro Pro Val Thr Thr Val
            740                 745                 750
Leu Ile Arg Arg Pro Asp Leu Arg Tyr Gln Leu Gly Phe Ser Val
            755                 760                 765
Gln Asn Gly Ile Ile Cys Ser Leu Met Arg Gly Gly Ile Ala Glu
            770                 775                 780
Arg Gly Gly Val Arg Val Gly His Arg Ile Ile Glu Ile Asn Gly
            785                 790                 795
Gln Ser Val Val Ala Thr Pro His Glu Lys Ile Val His Ile Leu
            800                 805                 810
Ser Asn Ala Val Gly Glu Ile His Met Lys Thr Met Pro Ala Ala
            815                 820                 825
Met Tyr Arg Leu Leu Thr Ala Gln Glu Gln Pro Val Tyr Ile
            830                 835
```

FIGURE 13T

```
Met Asn His Leu Glu Gly Ser Ala Glu Val Glu Val Ala Asp Glu
1               5                   10                  15
Ala Pro Gly Gly Glu Val Asn Glu Ser Val Glu Ala Asp Leu Glu
                20                  25                  30
His Pro Glu Val Glu Glu Gln Gln Pro Ser Pro Pro Pro Pro
                35                  40                  45
Ala Gly His Ala Pro Glu Asp His Arg Ala His Pro Ala Pro Pro
                50                  55                  60
Pro Pro Pro Pro Pro Gln Glu Glu Glu Glu Arg Gly Glu Cys
                65                  70                  75
Leu Ala Arg Ser Ala Ser Thr Glu Ser Gly Phe His Asn His Thr
                80                  85                  90
Asp Thr Ala Glu Gly Asp Val Leu Ala Ala Ala Arg Asp Gly Tyr
                95                  100                 105
Glu Ala Glu Arg Ala Gln Asp Ala Asp Asp Glu Ser Ala Tyr Ala
                110                 115                 120
Val Gln Tyr Arg Pro Glu Ala Glu Glu Tyr Thr Glu Gln Ala Glu
                125                 130                 135
Ala Glu His Ala Glu Ala Ala Gln Arg Arg Ala Leu Pro Asn His
                140                 145                 150
Leu His Phe His Ser Leu Glu His Glu Glu Ala Met Asn Ala Ala
                155                 160                 165
Tyr Ser Gly Tyr Val Tyr Thr His Arg Leu Phe His Arg Ala Glu
                170                 175                 180
Asp Glu Pro Tyr Ala Glu Pro Tyr Ala Asp Tyr Gly Gly Leu Gln
                185                 190                 195
Glu His Val Tyr Glu Glu Ile Gly Asp Ala Pro Glu Leu Glu Ala
                200                 205                 210
Arg Asp Gly Leu Arg Leu Tyr Glu Arg Glu Arg Asp Glu Ala Ala
                215                 220                 225
Ala Tyr Arg Gln Glu Ala Leu Gly Ala Arg Leu His His Tyr Asp
                230                 235                 240
Glu Arg Ser Asp Gly Glu Ser Asp Ser Pro Glu Lys Glu Ala Glu
                245                 250                 255
Phe Ala Pro Tyr Pro Arg Met Asp Ser Tyr Glu Gln Glu Glu Asp
                260                 265                 270
Ile Asp Gln Ile Val Ala Glu Val Lys Gln Ser Met Ser Ser Gln
                275                 280                 285
```

FIGURE 13U

```
Ser Leu Asp Lys Ala Ala Glu Asp Met Pro Glu Ala Glu Gln Asp
            290                 295                 300
Leu Glu Arg Ala Pro Thr Pro Gly Gly Gly His Pro Asp Ser Pro
            305                 310                 315
Gly Leu Pro Ala Pro Ala Gly Gln Gln Gln Arg Val Val Gly Thr
            320                 325                 330
Pro Gly Gly Ser Glu Val Gly Gln Arg Tyr Ser Lys Glu Lys Arg
            335                 340                 345
Asp Ala Ile Ser Leu Ala Ile Lys Asp Ile Lys Glu Ala Ile Glu
            350                 355                 360
Glu Val Lys Thr Arg Thr Ile Arg Ser Pro Tyr Thr Pro Asp Glu
            365                 370                 375
Pro Lys Glu Pro Ile Trp Val Met Arg Gln Asp Ile Ser Pro Thr
            380                 385                 390
Arg Asp Cys Asp Asp Gln Arg Pro Val Asp Gly Asp Ser Pro Ser
            395                 400                 405
Pro Gly Ser Ser Ser Pro Leu Gly Ala Glu Ser Ser Ile Thr Pro
            410                 415                 420
Leu His Pro Gly Asp Pro Thr Glu Ala Ser Thr Asn Lys Glu Ser
            425                 430                 435
Arg Lys Ser Leu Ala Ser Phe Pro Thr Tyr Val Glu Val Pro Gly
            440                 445                 450
Pro Cys Asp Pro Glu Asp Leu Ile Asp Gly Ile Ile Phe Ala Ala
            455                 460                 465
Asn Tyr Leu Gly Ser Thr Gln Leu Leu Ser Asp Lys Thr Pro Ser
            470                 475                 480
Lys Asn Val Arg Met Met Gln Ala Gln Glu Ala Val Ser Arg Ile
            485                 490                 495
Lys Thr Ala Gln Lys Leu Ala Lys Ser Arg Lys Lys Ala Pro Glu
            500                 505                 510
Gly Glu Ser Gln Pro Met Thr Glu Val Asp Leu Phe Ile Ser Thr
            515                 520                 525
Gln Arg Ile Lys Val Leu Asn Ala Asp Thr Gln Glu Pro Met Met
            530                 535                 540
Asp His Pro Leu Arg Thr Ile Ser Tyr Ile Ala Asp Ile Gly Asn
            545                 550                 555
Ile Val Val Leu Met Ala Arg Arg Arg Met Pro Arg Ser Asn Ser
            560                 565                 570
```

FIGURE 13V

```
Gln Glu Asn Val Glu Ala Ser His Pro Ser Gln Asp Ala Lys Arg
                575                 580                 585
Gln Tyr Lys Met Ile Cys His Val Phe Glu Ser Glu Asp Ala Gln
                590                 595                 600
Leu Ile Ala Gln Ser Ile Gly Gln Ala Phe Ser Val Ala Tyr Gln
                605                 610                 615
Glu Phe Leu Arg Ala Asn Gly Ile Asn Pro Glu Asp Leu Ser Gln
                620                 625                 630
Lys Glu Tyr Ser Asp Leu Leu Asn Thr Gln Asp Met Tyr Asn Asp
                635                 640                 645
Asp Leu Ile His Phe Ser Lys Ser Glu Asn Cys Lys Asp Val
                650                 655
```

FIGURE 13W

| | | | | | | | | | | | | | |
|---|---|---|---|---|---|---|---|---|---|---|---|---|---|
| <u>Met</u> | <u>Glu</u> | <u>Gln</u> | <u>Lys</u> | <u>Leu</u> | <u>Ile</u> | <u>Ser</u> | <u>Glu</u> | <u>Glu</u> | <u>Asp</u> | <u>Leu</u> | <u>Asn</u> | <u>Gly</u> | <u>Ile</u> | <u>Gln</u> |
| 1 | | | | 5 | | | | | 10 | | | | | 15 |
| Ile | Trp | Tyr | Pro | Cys | Asp | Pro | Glu | Asp | Leu | Ile | Asp | Gly | Ile | Ile |
| | | | | 20 | | | | | 25 | | | | | 30 |
| Phe | Ala | Ala | Asn | Tyr | Leu | Gly | Ser | Thr | Gln | Leu | Leu | Ser | Asp | Lys |
| | | | | 35 | | | | | 40 | | | | | 45 |
| Thr | Pro | Ser | Lys | Asn | Val | Arg | Met | Met | Gln | Ala | Gln | Glu | Ala | Val |
| | | | | 50 | | | | | 55 | | | | | 60 |
| Ser | Arg | Ile | Lys | Thr | Ala | Gln | Lys | Leu | Ala | Lys | Ser | Arg | Lys | Lys |
| | | | | 65 | | | | | 70 | | | | | 75 |
| Ala | Pro | Glu | Gly | Glu | Ser | Gln | Pro | Met | Thr | Glu | Val | Asp | Leu | Phe |
| | | | | 80 | | | | | 85 | | | | | 90 |
| Ile | Ser | Thr | Gln | Arg | Ile | Lys | Val | Leu | Asn | Ala | Asp | Thr | Gln | Glu |
| | | | | 95 | | | | | 100 | | | | | 105 |
| Pro | Met | Met | Asp | His | Pro | Leu | Arg | Thr | Ile | Ser | Tyr | Ile | Ala | Asp |
| | | | | 110 | | | | | 115 | | | | | 120 |
| Ile | Gly | Asn | Ile | Val | Val | Leu | Met | Ala | Arg | Arg | Arg | Met | Pro | Arg |
| | | | | 125 | | | | | 130 | | | | | 135 |
| Ser | Asn | Ser | Gln | Glu | Asn | Val | Glu | Ala | Ser | His | Pro | Ser | Gln | Asp |
| | | | | 140 | | | | | 145 | | | | | 150 |
| Ala | Lys | Arg | Gln | Tyr | Lys | Met | Ile | Cys | His | Val | Phe | Glu | Ser | Glu |
| | | | | 155 | | | | | 160 | | | | | 165 |
| Asp | Ala | Gln | Leu | Ile | Ala | Gln | Ser | Ile | Gly | Gln | Ala | Phe | Ser | Val |
| | | | | 170 | | | | | 175 | | | | | 180 |
| Ala | Tyr | Gln | Glu | Phe | Leu | Arg | Ala | Asn | Gly | Ile | Asn | Pro | Glu | Asp |
| | | | | 185 | | | | | 190 | | | | | 195 |
| Leu | Ser | Gln | Lys | Glu | Tyr | Ser | Asp | Leu | Leu | Asn | Thr | Gln | Asp | Met |
| | | | | 200 | | | | | 205 | | | | | 210 |
| Tyr | Asn | Asp | Asp | Leu | Ile | His | Phe | Ser | Lys | Ser | Glu | Asn | Cys | Lys |
| | | | | 215 | | | | | 220 | | | | | 225 |
| Asp | Val | Phe | Ile | Glu | Lys | Gln | Lys | Gly | Glu | Ile | Leu | Gly | Val | Val |
| | | | | 230 | | | | | 235 | | | | | 240 |
| Ile | Val | Glu | Ser | Gly | Trp | Gly | Ser | Ile | Leu | Pro | Thr | Val | Ile | Ile |
| | | | | 245 | | | | | 250 | | | | | 255 |
| Ala | Asn | Met | Met | His | Gly | Gly | Pro | Ala | Glu | Lys | Ser | Gly | Lys | Leu |
| | | | | 260 | | | | | 265 | | | | | 270 |
| Asn | Ile | Gly | Asp | Gln | Ile | Met | Ser | Ile | Asn | Gly | Thr | Ser | Leu | Val |
| | | | | 275 | | | | | 280 | | | | | 285 |

FIGURE 13X

```
Gly Leu Pro Leu Ser Thr Cys Gln Ser Ile Ile Lys Gly Leu Lys
                290                 295                 300
Asn Gln Ser Arg Val Lys Leu Asn Ile Val Arg Cys Pro Pro Val
                305                 310                 315
Thr Thr Val Leu Ile Arg Arg Pro Asp Leu Arg Tyr Gln Leu Gly
                320                 325                 330
Phe Ser Val Gln Asn Gly Ile Ile Cys Ser Leu Met Arg Gly Gly
                335                 340                 345
Ile Ala Glu Arg Gly Gly Val Arg Val Gly His Arg Ile Ile Glu
                350                 355                 360
Ile Asn Gly Gln Ser Val Val Ala Thr Pro His Glu Lys Ile Val
                365                 370                 375
His Ile Leu Ser Asn Ala Val Gly Glu Ile His Met Lys Thr Met
                380                 385                 390
Pro Ala Ala Met Tyr Arg Leu Leu Thr Ala Gln Glu Gln Pro Val
                395                 400                 405
Tyr Ile
```

FIGURE 13Y

| | | | | | | | | | | | | |
|---|---|---|---|---|---|---|---|---|---|---|---|---|
| Met | Ala | His | Arg | Lys | Arg | Gln | Ser | Thr | Ala | Ser | Ser | Met Leu Asp |
| 1 | | | | 5 | | | | | 10 | | | 15 |
| His | Arg | Ala | Arg | Pro | Gly | Pro | Ile | Pro | His | Asp | Gln | Glu Pro Glu |
| | | | | 20 | | | | | 25 | | | 30 |
| Asn | Glu | Asp | Thr | Glu | Leu | Pro | Leu | Glu | Ser | Tyr | Val | Pro Thr Gly |
| | | | | 35 | | | | | 40 | | | 45 |
| Leu | Glu | Leu | Gly | Thr | Leu | Arg | Pro | Asp | Ser | Pro | Thr | Pro Glu Glu |
| | | | | 50 | | | | | 55 | | | 60 |
| Gln | Glu | Cys | His | Asn | His | Ser | Pro | Asp | Gly | Asp | Ser | Ser Ser Asp |
| | | | | 65 | | | | | 70 | | | 75 |
| Tyr | Val | Asn | Asn | Thr | Ser | Glu | Glu | Glu | Asp | Tyr | Asp | Glu Gly Leu |
| | | | | 80 | | | | | 85 | | | 90 |
| Pro | Glu | Glu | Glu | Glu | Gly | Val | Thr | Tyr | Tyr | Ile | Arg | Tyr Cys Pro |
| | | | | 95 | | | | | 100 | | | 105 |
| Glu | Asp | Asp | Ser | Tyr | Leu | Glu | Gly | Met | Asp | Cys | Asn | Gly Glu Glu |
| | | | | 110 | | | | | 115 | | | 120 |
| Tyr | Leu | Ala | His | Gly | Ala | His | Pro | Val | Asp | Thr | Asp | Glu Cys Gln |
| | | | | 125 | | | | | 130 | | | 135 |
| Glu | Ala | Val | Glu | Asp | Trp | Thr | Asp | Ser | Val | Gly | Pro | His Thr His |
| | | | | 140 | | | | | 145 | | | 150 |
| Ser | His | Gly | Ala | Glu | Asn | Ser | Gln | Glu | Tyr | Pro | Asp | Ser His Leu |
| | | | | 155 | | | | | 160 | | | 165 |
| Pro | Ile | Pro | Glu | Asp | Asp | Pro | Thr | Val | Leu | Glu | Val | His Asp Gln |
| | | | | 170 | | | | | 175 | | | 180 |
| Glu | Glu | Asp | Gly | His | Tyr | Cys | Pro | Ser | Lys | Glu | Ser | Tyr Gln Asp |
| | | | | 185 | | | | | 190 | | | 195 |
| Tyr | Tyr | Pro | Pro | Glu | Thr | Asn | Gly | Asn | Thr | Gly | Gly | Ala Ser Pro |
| | | | | 200 | | | | | 205 | | | 210 |
| Tyr | Arg | Met | Arg | Arg | Gly | Asp | Gly | Asp | Leu | Glu | Glu | Gln Glu Glu |
| | | | | 215 | | | | | 220 | | | 225 |
| Asp | Ile | Asp | Gln | Ile | Val | Ala | Glu | Ile | Lys | Met | Ser | Leu Ser Met |
| | | | | 230 | | | | | 235 | | | 240 |
| Thr | Ser | Ile | Thr | Ser | Ala | Ser | Glu | Ala | Ser | Pro | Glu | His Met Pro |
| | | | | 245 | | | | | 250 | | | 255 |
| Glu | Leu | Asp | Pro | Gly | Asp | Ser | Thr | Glu | Ala | Cys | Ser | Pro Ser Asp |
| | | | | 260 | | | | | 265 | | | 270 |
| Thr | Gly | Arg | Gly | Pro | Ser | Arg | Gln | Glu | Ala | Arg | Pro | Lys Ser Leu |
| | | | | 275 | | | | | 280 | | | 285 |

FIGURE 13Z

```
Asn Leu Pro Pro Glu Val Lys His Ser Gly Asp Pro Gln Arg Gly
            290                 295                 300
Leu Lys Thr Lys Thr Arg Thr Pro Glu Glu Arg Pro Lys Trp Pro
            305                 310                 315
Gln Glu Gln Val Cys Asn Gly Leu Glu Gln Pro Arg Lys Gln Gln
            320                 325                 330
Arg Ser Asp Leu Asn Gly Pro Thr Asp Asn Asn Ile Pro Glu
            335                 340                 345
Thr Lys Lys Val Ala Ser Phe Pro Ser Phe Val Ala Val Pro Gly
            350                 355                 360
Pro Cys Glu Pro Glu Asp Leu Ile Asp Gly Ile Ile Phe Ala Ala
            365                 370                 375
Asn Tyr Leu Gly Ser Thr Gln Leu Leu Ser Glu Arg Asn Pro Ser
            380                 385                 390
Lys Asn Ile Arg Met Met Gln Ala Gln Glu Ala Val Ser Arg Val
            395                 400                 405
Lys Arg Met Gln Lys Ala Ala Lys Ile Lys Lys Lys Ala Asn Ser
            410                 415                 420
Glu Gly Asp Ala Gln Thr Leu Thr Glu Val Asp Leu Phe Ile Ser
            425                 430                 435
Thr Gln Arg Ile Lys Val Leu Asn Ala Asp Thr Gln Glu Thr Met
            440                 445                 450
Met Asp His Ala Leu Arg Thr Ile Ser Tyr Ile Ala Asp Ile Gly
            455                 460                 465
Asn Ile Val Val Leu Met Ala Arg Arg Arg Met Pro Arg Ser Ala
            470                 475                 480
Ser Gln Asp Cys Ile Glu Thr Thr Pro Gly Ala Gln Glu Gly Lys
            485                 490                 495
Lys Gln Tyr Lys Met Ile Cys His Val Phe Glu Ser Glu Asp Ala
            500                 505                 510
Gln Leu Ile Ala Gln Ser Ile Gly Gln Ala Phe Ser Val Ala Tyr
            515                 520                 525
Gln Glu Phe Leu Arg Ala Asn Gly Ile Asn Pro Glu Asp Leu Ser
            530                 535                 540
Gln Lys Glu Tyr Ser Asp Ile Ile Asn Thr Gln Glu Met Tyr Asn
            545                 550                 555
Asp Asp Leu Ile His Phe Ser Asn Ser Glu Asn Cys Lys Glu Leu
            560                 565                 570
```

FIGURE 13AA

```
Gln Leu Glu Lys His Lys Gly Glu Ile Leu Gly Val Val Val
            575                 580                 585
Glu Ser Gly Trp Gly Ser Ile Leu Pro Thr Val Ile Leu Ala Asn
            590                 595                 600
Met Met Asn Gly Gly Pro Ala Ala Arg Ser Gly Lys Leu Ser Ile
            605                 610                 615
Gly Asp Gln Ile Met Ser Ile Asn Gly Thr Ser Leu Val Gly Leu
            620                 625                 630
Pro Leu Ala Thr Cys Gln Gly Ile Ile Lys Gly Leu Lys Asn Gln
            635                 640                 645
Thr Gln Val Lys Leu Asn Ile Val Ser Cys Pro Pro Val Thr Thr
            650                 655                 660
Val Leu Ile Lys Arg Pro Asp Leu Lys Tyr Gln Leu Gly Phe Ser
            665                 670                 675
Val Gln Asn Gly Ile Ile Cys Ser Leu Met Arg Gly Gly Ile Ala
            680                 685                 690
Glu Arg Gly Gly Val Arg Val Gly His Arg Ile Ile Glu Ile Asn
            695                 700                 705
Gly Gln Ser Val Val Ala Thr Ala His Glu Lys Ile Val Gln Ala
            710                 715                 720
Leu Ser Asn Ser Val Gly Glu Ile His Met Lys Thr Met Pro Ala
            725                 730                 735
Ala Met Phe Arg Leu Leu Thr Gly Gln Glu Thr Pro Leu Tyr Ile
            740                 745                 750
```

FIGURE 13BB

```
Met Ala His Arg Lys Arg Gln Ser Thr Ala Ser Ser Met Leu Asp
 1               5                  10                  15
His Arg Ala Arg Pro Gly Pro Ile Pro His Asp Gln Glu Pro Glu
                20                  25                  30
Asn Glu Asp Thr Glu Leu Pro Leu Glu Ser Tyr Val Pro Thr Gly
                35                  40                  45
Leu Glu Leu Gly Thr Leu Arg Pro Asp Ser Pro Thr Pro Glu Glu
                50                  55                  60
Gln Glu Cys His Asn His Ser Pro Asp Gly Asp Ser Ser Ser Asp
                65                  70                  75
Tyr Val Asn Asn Thr Ser Glu Glu Glu Asp Tyr Asp Glu Gly Leu
                80                  85                  90
Pro Glu Glu Glu Glu Gly Val Thr Tyr Tyr Ile Arg Tyr Cys Pro
                95                 100                 105
Glu Asp Asp Ser Tyr Leu Glu Gly Met Asp Cys Asn Gly Glu Glu
               110                 115                 120
Tyr Leu Ala His Gly Ala His Pro Val Asp Thr Asp Glu Cys Gln
               125                 130                 135
Glu Ala Val Glu Asp Trp Thr Asp Ser Val Gly Pro His Thr His
               140                 145                 150
Ser His Gly Ala Glu Asn Ser Gln Glu Tyr Pro Asp Ser His Leu
               155                 160                 165
Pro Ile Pro Glu Asp Asp Pro Thr Val Leu Glu Val His Asp Gln
               170                 175                 180
Glu Glu Asp Gly His Tyr Cys Pro Ser Lys Glu Ser Tyr Gln Asp
               185                 190                 195
Tyr Tyr Pro Pro Glu Thr Asn Gly Asn Thr Gly Gly Ala Ser Pro
               200                 205                 210
Tyr Arg Met Arg Arg Gly Asp Gly Asp Leu Glu Glu Gln Glu Glu
               215                 220                 225
Asp Ile Asp Gln Ile Val Ala Glu Ile Lys Met Ser Leu Ser Met
               230                 235                 240
Thr Ser Ile Thr Ser Ala Ser Glu Ala Ser Pro Glu His Met Pro
               245                 250                 255
Glu Leu Asp Pro Gly Asp Ser Thr Glu Ala Cys Ser Pro Ser Asp
               260                 265                 270
Thr Gly Arg Gly Pro Ser Arg Gln Glu Ala Arg Pro Lys Ser Leu
               275                 280                 285
```

FIGURE 13CC

```
Asn Leu Pro Pro Glu Val Lys His Ser Gly Asp Pro Gln Arg Gly
                290                 295                 300
Leu Lys Thr Lys Thr Arg Thr Pro Glu Glu Arg Pro Lys Trp Pro
                305                 310                 315
Gln Glu Gln Val Cys Asn Gly Leu Glu Gln Pro Arg Lys Gln Gln
                320                 325                 330
Arg Ser Asp Leu Asn Gly Pro Thr Asp Asn Asn Ile Pro Glu
                335                 340                 345
Thr Lys Lys Val Ala Ser Phe Pro Ser Phe Val Ala Val Pro Gly
                350                 355                 360
Pro Cys Glu Pro Glu Asp Leu Ile Asp Gly Ile Ile Phe Ala Ala
                365                 370                 375
Asn Tyr Leu Gly Ser Thr Gln Leu Leu Ser Glu Arg Asn Pro Ser
                380                 385                 390
Lys Asn Ile Arg Met Met Gln Ala Gln Glu Ala Val Ser Arg Val
                395                 400                 405
Lys Arg Met Gln Lys Ala Ala Lys Ile Lys Lys Ala Asn Ser
                410                 415                 420
Glu Gly Asp Ala Gln Thr Leu Thr Glu Val Asp Leu Phe Ile Ser
                425                 430                 435
Thr Gln Arg Ile Lys Val Leu Asn Ala Asp Thr Gln Glu Thr Met
                440                 445                 450
Met Asp His Ala Leu Arg Thr Ile Ser Tyr Ile Ala Asp Ile Gly
                455                 460                 465
Asn Ile Val Val Leu Met Ala Arg Arg Arg Met Pro Arg Ser Ala
                470                 475                 480
Ser Gln Asp Cys Ile Glu Thr Thr Pro Gly Ala Gln Glu Gly Lys
                485                 490                 495
Lys Gln Tyr Lys Met Ile Cys His Val Phe Glu Ser Glu Asp Ala
                500                 505                 510
Gln Leu Ile Ala Gln Ser Ile Gly Gln Ala Phe Ser Val Ala Tyr
                515                 520                 525
Gln Glu Phe Leu Arg Ala Asn Gly Ile Asn Pro Glu Asp Leu Ser
                530                 535                 540
Gln Lys Glu Tyr Ser Asp Ile Ile Asn Thr Gln Glu Met Tyr Asn
                545                 550                 555
Asp Asp Leu Ile His Phe Ser Asn Ser Glu Asn Cys Lys Glu Leu
                560                 565                 570
```

FIGURE 13DD

```
Gln Leu Glu Lys His Lys Gly Glu Ile Leu Ala Ala Val Val Val
                575                 580                     585
Glu Ser Gly Trp Gly Ser Ile Leu Pro Thr Val Ile Leu Ala Asn
                590                 595                     600
Met Met Asn Gly Gly Pro Ala Ala Arg Ser Gly Lys Leu Ser Ile
                605                 610                     615
Gly Asp Gln Ile Met Ser Ile Asn Gly Thr Ser Leu Val Gly Leu
                620                 625                     630
Pro Leu Ala Thr Cys Gln Gly Ile Ile Lys Gly Leu Lys Asn Gln
                635                 640                     645
Thr Gln Val Lys Leu Asn Ile Val Ser Cys Pro Pro Val Thr Thr
                650                 655                     660
Val Leu Ile Lys Arg Pro Asp Leu Lys Tyr Gln Leu Gly Phe Ser
                665                 670                     675
Val Gln Asn Gly Ile Ile Cys Ser Leu Met Arg Gly Gly Ile Ala
                680                 685                     690
Glu Arg Gly Gly Val Arg Val Gly His Arg Ile Ile Glu Ile Asn
                695                 700                     705
Gly Gln Ser Val Val Ala Thr Ala His Glu Lys Ile Val Gln Ala
                710                 715                     720
Leu Ser Asn Ser Val Gly Glu Ile His Met Lys Thr Met Pro Ala
                725                 730                     735
Ala Met Phe Arg Leu Leu Thr Gly Gln Glu Thr Pro Leu Tyr Ile
                740                 745                     750
```

FIGURE 13EE

```
Met Ala His Arg Lys Arg Gln Ser Thr Ala Ser Ser Met Leu Asp
 1            5                      10                   15
His Arg Ala Arg Pro Gly Pro Ile Pro His Asp Gln Glu Pro Glu
             20                      25                   30
Asn Glu Asp Thr Glu Leu Pro Leu Glu Ser Tyr Val Pro Thr Gly
             35                      40                   45
Leu Glu Leu Gly Thr Leu Arg Pro Asp Ser Pro Thr Pro Glu Glu
             50                      55                   60
Gln Glu Cys His Asn His Ser Pro Asp Gly Asp Ser Ser Ser Asp
             65                      70                   75
Tyr Val Asn Asn Thr Ser Glu Glu Glu Asp Tyr Asp Glu Gly Leu
             80                      85                   90
Pro Glu Glu Glu Glu Gly Val Thr Tyr Tyr Ile Arg Tyr Cys Pro
             95                     100                  105
Glu Asp Asp Ser Tyr Leu Glu Gly Met Asp Cys Asn Gly Glu Glu
            110                     115                  120
Tyr Leu Ala His Gly Ala His Pro Val Asp Thr Asp Glu Cys Gln
            125                     130                  135
Glu Ala Val Glu Asp Trp Thr Asp Ser Val Gly Pro His Thr His
            140                     145                  150
Ser His Gly Ala Glu Asn Ser Gln Glu Tyr Pro Asp Ser His Leu
            155                     160                  165
Pro Ile Pro Glu Asp Asp Pro Thr Val Leu Glu Val His Asp Gln
            170                     175                  180
Glu Glu Asp Gly His Tyr Cys Pro Ser Lys Glu Ser Tyr Gln Asp
            185                     190                  195
Tyr Tyr Pro Pro Glu Thr Asn Gly Asn Thr Gly Gly Ala Ser Pro
            200                     205                  210
Tyr Arg Met Arg Arg Gly Asp Gly Asp Leu Glu Glu Gln Glu Glu
            215                     220                  225
Asp Ile Asp Gln Ile Val Ala Glu Ile Lys Met Ser Leu Ser Met
            230                     235                  240
Thr Ser Ile Thr Ser Ala Ser Glu Ala Ser Pro Glu His Met Pro
            245                     250                  255
Glu Leu Asp Pro Gly Asp Ser Thr Glu Ala Cys Ser Pro Ser Asp
            260                     265                  270
Thr Gly Arg Gly Pro Ser Arg Gln Glu Ala Arg Pro Lys Ser Leu
            275                     280                  285
```

FIGURE 13FF

```
Asn Leu Pro Pro Glu Val Lys His Ser Gly Asp Pro Gln Arg Gly
                290                 295                 300
Leu Lys Thr Lys Thr Arg Thr Pro Glu Glu Arg Pro Lys Trp Pro
                305                 310                 315
Gln Glu Gln Val Cys Asn Gly Leu Glu Gln Pro Arg Lys Gln Gln
                320                 325                 330
Arg Ser Asp Leu Asn Gly Pro Thr Asp Asn Asn Ile Pro Glu
                335                 340                 345
Thr Lys Lys Val Ala Ser Phe Pro Ser Phe Val Ala Val Pro Gly
                350                 355                 360
Pro Cys Glu Pro Glu Asp Leu Ile Asp Gly Ile Ile Phe Ala Ala
                365                 370                 375
Asn Tyr Leu Gly Ser Thr Gln Leu Leu Ser Glu Arg Asn Pro Ser
                380                 385                 390
Lys Asn Ile Arg Met Met Gln Ala Gln Glu Ala Val Ser Arg Val
                395                 400                 405
Lys Arg Met Gln Lys Ala Ala Lys Ile Lys Lys Ala Asn Ser
                410                 415                 420
Glu Gly Asp Ala Gln Thr Leu Thr Glu Val Asp Leu Phe Ile Ser
                425                 430                 435
Thr Gln Arg Ile Lys Val Leu Asn Ala Asp Thr Gln Glu Thr Met
                440                 445                 450
Met Asp His Ala Leu Arg Thr Ile Ser Tyr Ile Ala Asp Ile Gly
                455                 460                 465
Asn Ile Val Val Leu Met Ala Arg Arg Arg Met Pro Arg Ser Ala
                470                 475                 480
Ser Gln Asp Cys Ile Glu Thr Thr Pro Gly Ala Gln Glu Gly Lys
                485                 490                 495
Lys Gln Tyr Lys Met Ile Cys His Val Phe Glu Ser Glu Asp Ala
                500                 505                 510
Gln Leu Ile Ala Gln Ser Ile Gly Gln Ala Phe Ser Val Ala Tyr
                515                 520                 525
Gln Glu Phe Leu Arg Ala Asn Gly Ile Asn Pro Glu Asp Leu Ser
                530                 535                 540
Gln Lys Glu Tyr Ser Asp Ile Ile Asn Thr Gln Glu Met Tyr Asn
                545                 550                 555
Asp Asp Leu Ile His Phe Ser Asn Ser Glu Asn Cys Lys Glu Leu
                560                 565                 570
```

FIGURE 13GG

| | | | | | | | | | | | | |
|---|---|---|---|---|---|---|---|---|---|---|---|---|
| <u>Met</u> | <u>Glu</u> | <u>Gln</u> | <u>Lys</u> | <u>Leu</u> | <u>Ile</u> | <u>Ser</u> | <u>Glu</u> | <u>Glu</u> | <u>Asp</u> | <u>Leu</u> | <u>Asn</u> | <u>Gly</u> | <u>Ile</u> | <u>Gln</u> |
| 1 | | | | 5 | | | | | 10 | | | | | 15 |
| <u>Ile</u> | <u>Trp</u> | <u>Tyr</u> | Pro | Cys | Glu | Pro | Glu | Asp | Leu | Ile | Asp | Gly | Ile | Ile |
| | | | | 20 | | | | | 25 | | | | | 30 |
| Phe | Ala | Ala | Asn | Tyr | Leu | Gly | Ser | Thr | Gln | Leu | Leu | Ser | Glu | Arg |
| | | | | 35 | | | | | 40 | | | | | 45 |
| Asn | Pro | Ser | Lys | Asn | Ile | Arg | Met | Met | Gln | Ala | Gln | Glu | Ala | Val |
| | | | | 50 | | | | | 55 | | | | | 60 |
| Ser | Arg | Val | Lys | Arg | Met | Gln | Lys | Ala | Ala | Lys | Ile | Lys | Lys | Lys |
| | | | | 65 | | | | | 70 | | | | | 75 |
| Ala | Asn | Ser | Glu | Gly | Asp | Ala | Gln | Thr | Leu | Thr | Glu | Val | Asp | Leu |
| | | | | 80 | | | | | 85 | | | | | 90 |
| Phe | Ile | Ser | Thr | Gln | Arg | Ile | Lys | Val | Leu | Asn | Ala | Asp | Thr | Gln |
| | | | | 95 | | | | | 100 | | | | | 105 |
| Glu | Thr | Met | Met | Asp | His | Ala | Leu | Arg | Thr | Ile | Ser | Tyr | Ile | Ala |
| | | | | 110 | | | | | 115 | | | | | 120 |
| Asp | Ile | Gly | Asn | Ile | Val | Val | Leu | Met | Ala | Arg | Arg | Arg | Met | Pro |
| | | | | 125 | | | | | 130 | | | | | 135 |
| Arg | Ser | Ala | Ser | Gln | Asp | Cys | Ile | Glu | Thr | Thr | Pro | Gly | Ala | Gln |
| | | | | 140 | | | | | 145 | | | | | 150 |
| Glu | Gly | Lys | Lys | Gln | Tyr | Lys | Met | Ile | Cys | His | Val | Phe | Glu | Ser |
| | | | | 155 | | | | | 160 | | | | | 165 |
| Glu | Asp | Ala | Gln | Leu | Ile | Ala | Gln | Ser | Ile | Gly | Gln | Ala | Phe | Ser |
| | | | | 170 | | | | | 175 | | | | | 180 |
| Val | Ala | Tyr | Gln | Glu | Phe | Leu | Arg | Ala | Asn | Gly | Ile | Asn | Pro | Glu |
| | | | | 185 | | | | | 190 | | | | | 195 |
| Asp | Leu | Ser | Gln | Lys | Glu | Tyr | Ser | Asp | Ile | Ile | Asn | Thr | Gln | Glu |
| | | | | 200 | | | | | 205 | | | | | 210 |
| Met | Tyr | Asn | Asp | Asp | Leu | Ile | His | Phe | Ser | Asn | Ser | Glu | Asn | Cys |
| | | | | 215 | | | | | 220 | | | | | 225 |
| Lys | Glu | Leu | Gln | Leu | Glu | Lys | His | Lys | Gly | Glu | Ile | Leu | Gly | Val |
| | | | | 230 | | | | | 235 | | | | | 240 |
| Val | Val | Val | Glu | Ser | Gly | Trp | Gly | Ser | Ile | Leu | Pro | Thr | Val | Ile |
| | | | | 245 | | | | | 250 | | | | | 255 |
| Leu | Ala | Asn | Met | Met | Asn | Gly | Gly | Pro | Ala | Ala | Arg | Ser | Gly | Lys |
| | | | | 260 | | | | | 265 | | | | | 270 |
| Leu | Ser | Ile | Gly | Asp | Gln | Ile | Met | Ser | Ile | Asn | Gly | Thr | Ser | Leu |
| | | | | 275 | | | | | 280 | | | | | 285 |

FIGURE 13HH

```
Val Gly Leu Pro Leu Ala Thr Cys Gln Gly Ile Ile Lys Gly Leu
                290                 295                 300
Lys Asn Gln Thr Gln Val Lys Leu Asn Ile Val Ser Cys Pro Pro
                305                 310                 315
Val Thr Thr Val Leu Ile Lys Arg Pro Asp Leu Lys Tyr Gln Leu
                320                 325                 330
Gly Phe Ser Val Gln Asn Gly Ile Ile Cys Ser Leu Met Arg Gly
                335                 340                 345
Gly Ile Ala Glu Arg Gly Gly Val Arg Val Gly His Arg Ile Ile
                350                 355                 360
Glu Ile Asn Gly Gln Ser Val Val Ala Thr Ala His Glu Lys Ile
                365                 370                 375
Val Gln Ala Leu Ser Asn Ser Val Gly Glu Ile His Met Lys Thr
                380                 385                 390
Met Pro Ala Ala Met Phe Arg Leu Leu Thr Gly Gln Glu Thr Pro
                395                 400                 405
Leu Tyr Ile
```

A

B

SEQUENCE LISTING

<160> NUMBER OF SEQ ID NOS: 24

<210> SEQ ID NO 1
<211> LENGTH: 2520
<212> TYPE: DNA
<213> ORGANISM: rattus norvegicus

<400> SEQUENCE: 1

```
atgaaccact tggagggctc cgcggaggtg gaggtggccg acgaggcgcc aggaggggag        60
gtgaacgagt ccgtggaggc cgacctggag cacccgagg tggaggaaga gcagcagccg        120 tcgccccgc cgcccgcagg tcacgcaccc gaggaccacc gcgcgcatcc ggcgccgccg        180
ccgccgccac caccgcagga ggaggaggag gagcgcggcg agtgcctggc tcgctcggcc        240
agcaccgaga gcggcttcca caaccacacg gacaccgctg agggcgacgt gctcgccgcg        300
gcccgagacg gctacgaggc ggagcgcgcg caggacgccg acgatgagag cgcctacgcc        360
gtgcagtacc ggcccgaggc cgaggagtac acggagcagg cggaggccga gcacgccgag        420
gcggcgcagc ggcgcgcgct gcccaaccac ctgcacttcc actcgctgga gcacgaggaa        480
gccatgaacg ccgcctactc gggctatgtc tacacgcacc ggctcttcca ccgcgccgag        540
```

```
gacgagccct acgccgagcc ctacgccgac tacggcggcc tccaggagca cgtgtacgag    600
gagatcgggg acgcgcctga gctggaggcg cgcgacggcc tgcggctcta tgagcgggag    660
cgcgacgagg cggccgccta ccgccaggag gccctaggcg cgcggctgca ccactacgac    720
gagcgctccg acggcgagtc cgacagcccc gagaaggagg cggagttcgc gccctacccg    780
cgcatggaca gttatgagca ggaagaggac atcgaccaga tcgtggccga ggtcaagcag    840
agcatgagct cgcagagcct cgacaaggcg gccgaagaca tgcccgaggc ggagcaggac    900
ctggagcgcg ccccgacccc gggaggggga caccccgaca gccctgggct gccagcacct    960
gccgggcagc agcagcgagt tgtgggaacc ccggaggca gcgaggttgg tcagcggtac   1020
agcaaggaaa agagggatgc catctcgctg gccatcaagg acatcaagga ggccatcgaa   1080
gaagtgaaaa ccaggaccat ccgttcgcct acaccccccg acgaacccaa agagcccatc   1140
tgggtcatgc gccaggacat tagccccaca agggactgtg acgaccagag gcccgtggac   1200
ggagattctc cgtctcctgg cagttcctca cccctgggtg ctgagtcatc aatcacaccc   1260
cttcatcccg gtgaccccac ggaagcctcc actaataaag agtcaagaaa aagcttggct   1320
tcattcccaa cctacgttga agttcctgga ccctgcgacc ctgaagactt gatcgatgga   1380
attattttg ctgccaatta ccttggttcc actcagctac tctcagacaa aactccctcc   1440
aaaaacgtgc gcatgatgca ggcccaggaa gcagtaagcc ggatcaagac ggcccagaaa   1500
ttagccaaaa gcaggaagaa ggctcctgaa ggcgaatctc agccaatgac tgaggtggac   1560
ctcttcatct ccacccagag gatcaaagtg ttgaatgcag atacacagga gcctatgatg   1620
gaccaccctc tgaggaccat ttcctacatc gcagacattg gaacatcgt cgtgctgatg   1680
gccgcaggc ggatgccccg ctccaactcc caggagaatg tggaggcctc tcacccatcc   1740
caggatgcaa acggcagta caagatgatc tgtcatgtct ttgagtctga ggacgcccag   1800
ctgatcgcac agtccatcgg gcaggccttc agcgttgcat accaggagtt cctcagggcc   1860
aacgggatta acccagaaga cctgagccag aaggagtaca gcgacctgct caacacccag   1920
gacatgtaca cgatgacct gatccacttc tccaagtcgg aaaactgcaa agatgtcttc   1980
atagagaagc agaaaggaga atcctgggga gttgtgattg tggagtctgg ctgggatcc   2040
attctgccaa ccgtgatcat tgccaacatg atgcacggag ccccgccga aagtcgggg    2100
aagctgaaca tcggggacca gatcatgtcc attaacggca ccagcctggt gggcctgccc   2160
ctgtccacct gccagagcat cattaaggc ttaaagaacc agtcccgcgt gaagctgaac   2220
atcgtgaggt gccccccagt gaccacagtg ctaattagga ggccggacct tcgctaccag   2280
ctgggtttca gcgtgcagaa tggaattatc tgtagcctca tgagagggggg aatagctgag   2340
agaggaggtg tccgcgtggg acatcggatc attgaaatca acggccagag tgtcgtagcc   2400
acaccacacg agaagatcgt ccacatactc tccaatgctg ttggggagat ccacatgaag   2460
acaatgccag cagccatgta cagactgctg acagcccagg agcagcccgt ttacatctga   2520
```

<210> SEQ ID NO 2
<211> LENGTH: 2520
<212> TYPE: DNA
<213> ORGANISM: rattus norvegicus

<400> SEQUENCE: 2

```
atgaaccact tggagggctc cgcggaggtg gaggtggccg acgaggcgcc aggaggggag     60
gtgaacgagt ccgtggaggc cgacctggag caccccgagg tggaggaaga gcagcagccg    120
```

-continued

```
tcgccccgc cgcccgcagg tcacgcaccc gaggaccacc gcgcgcatcc ggcgccgccg      180
ccgccgccac caccgcagga ggaggaggag gagcgcggcg agtgcctggc tcgctcggcc      240
agcaccgaga gcggcttcca caaccacacg gacaccgctg agggcgacgt gctcgccgcg      300
gcccgagacg gctacgaggc ggagcgcgcg caggacgcca acgatgagag cgcctacgcc      360
gtgcagtacc ggcccgaggc cgaggagtac acggagcagg cggaggccga gcacgccgag      420
gcggcgcagc ggcgcgcgct gcccaaccac ctgcacttcc actcgctgga gcacgaggaa      480
gccatgaacg ccgcctactc gggctatgtc tacacgcacc ggctcttcca ccgcgccgag      540
gacgagccct acgccgagcc ctacgccgac tacggcggcc tccaggagca cgtgtacgag      600
gagatcgggg acgcgcctga gctggaggcg cgcgacggcc tgcggctcta tgagcgggag      660
cgcgacgagg cggccgccta ccgccaggag gccctaggcg cgcggctgca ccactacgac      720
gagcgctccg acggcgagtc cgacagcccc gagaaggagg cggagttcgc gccctacccg      780
cgcatggaca gttatgagca ggaagaggac atcgaccaga tcgtggccga ggtcaagcag      840
agcatgagct cgcagagcct cgacaaggcg gccgaagaca tgcccgaggc ggagcaggac      900
ctggagcgcg ccccgacccc gggaggggga caccccgaca gccctgggct gccagcacct      960
gccgggcagc agcagcgagt tgtgggaacc ccgggaggca gcgaggttgg tcagcggtac     1020
agcaaggaaa agagggatgc catctcgctg gccatcaagg acatcaagga ggccatcgaa     1080
gaagtgaaaa ccaggaccat ccgttcgcct tacacccccg acgaacccaa agagcccatc     1140
tgggtcatgc gccaggacat tagccccaca agggactgtg acgaccagag gcccgtggac     1200
ggagattctc cgtctcctgg cagttcctca ccctgggtg ctgagtcatc aatcacaccc      1260
cttcatcccg gtgaccccac ggaagcctcc actaataaag agtcaagaaa aagcttggct     1320
tcattcccaa cctacgttga agttcctgga ccctgcgacc ctgaagactt gatcgatgga     1380 attattttg ctgccaatta ccttggttcc actcagctac tctcagacaa aactccctcc      1440
aaaaacgtgc gcatgatgca ggcccaggaa gcagtaagcc ggatcaagac ggcccagaaa     1500
ttagccaaaa gcaggaagaa ggctcctgaa ggcgaatctc agccaatgac tgaggtggac     1560
ctcttcatct ccacccagag gatcaaagtg ttgaatgcag atacacagga gcctatgatg     1620
gaccaccctc tgaggaccat ttcctacatc gcagacattg ggaacatcgt cgtgctgatg     1680
gcccgcaggc ggatgccccg ctccaactcc caggagaatg tggaggcctc tcacccatcc     1740
caggatgcaa aacggcagta caagatgatc tgtcatgtct ttgagtctga ggacgcccag     1800
ctgatcgcac agtccatcgg gcaggccttc agcgttgcat accaggagtt cctcagggcc     1860
aacgggatta acccagaaga cctgagccaa aaggagtaca cgcgacctgct caacacccag     1920 gacatgtaca acgatgacct gatccacttc tccaagtcgg aaaactgcaa agatgtcttc     1980
atagagaagc agaaaggaga aatcctggcg gccgtgattg tggagtctgg ctggggatcc     2040
attctgccaa ccgtgatcat tgccaacatg atgcacggag gccccgccga agtcgggg       2100 aagctgaaca tcggggacca gatcatgtcc attaacggca ccagcctggt gggcctgccc      2160
ctgtccacct gccagagcat cattaaggcc ttaaagaacc agtcccgcgt gaagctgaac     2220
atcgtgaggt gccccccagt gaccacagtg ctaattagga ggccggacct tcgctaccag     2280
ctgggtttca gcgtgcagaa tggaattatc tgtagcctca tgagagggg aatagctgag     2340 agaggaggtg tccgcgtggg acatcggatc attgaaatca acggccagag tgtcgtagcc     2400
acaccacacg agaagatcgt ccacatactc tccaatgctg ttggggagat ccacatgaag     2460
acaatgccag cagccatgta cagactgctg acagcccagg agcagcccgt ttacatctga     2520
```

<210> SEQ ID NO 3
<211> LENGTH: 1980
<212> TYPE: DNA
<213> ORGANISM: rattus norvegicus

<400> SEQUENCE: 3

| | | | | | |
|---|---|---|---|---|---|
| atgaaccact | tggagggctc | cgcggaggtg | gaggtggccg | acgaggcgcc | aggaggggag | 60 |
| gtgaacgagt | ccgtggaggc | cgacctggag | caccccgagg | tggaggaaga | gcagcagccg | 120 |
| tcgccccgc | cgcccgcagg | tcacgcaccc | gaggaccacc | cgcgcatcc | ggcgccgccg | 180 |
| ccgccgccac | caccgcagga | ggaggaggag | gagcgcggcg | agtgcctggc | tcgctcggcc | 240 |
| agcaccgaga | gcggcttcca | caaccacacg | acaccgctg | agggcgacgt | gctcgccgcg | 300 |
| gcccgagacg | gctacgaggc | ggagcgcgcg | caggacgccg | acgatgagag | cgcctacgcc | 360 |
| gtgcagtacc | ggcccgaggc | cgaggagtac | acggagcagg | cggaggccga | gcacgccgag | 420 |
| gcggcgcagc | ggcgcgcgct | gcccaaccac | ctgcacttcc | actcgctgga | gcacgaggaa | 480 |
| gccatgaacg | ccgcctactc | gggctatgtc | tacacgcacc | ggctcttcca | ccgcgccgag | 540 |
| gacgagccct | acgccgagcc | ctacgccgac | tacgcgggcc | tccaggagca | cgtgtacgag | 600 |
| gagatcgggg | acgcgcctga | gctggaggcg | cgcgacggcc | tgcggctcta | tgagcgggag | 660 |
| cgcgacgagg | cggccgccta | ccgccaggag | gccctaggcg | cgcggctgca | ccactacgac | 720 |
| gagcgctccg | acggcgagtc | cgacagcccc | gagaaggagg | cggagttcgc | gccctacccg | 780 |
| cgcatggaca | gttatgagca | ggaagaggac | atcgaccaga | tcgtggccga | ggtcaagcag | 840 |
| agcatgagct | cgcagagcct | cgacaaggcg | gccgaagaca | tgcccgaggc | ggagcaggac | 900 |
| ctggagcgcg | ccccgacccc | gggagggga | caccccgaca | gccctgggct | gccagcacct | 960 |
| gccgggcagc | agcagcgagt | tgtgggaacc | ccggaggca | gcgaggttgg | tcagcggtac | 1020 |
| agcaaggaaa | agagggatgc | catctcgctg | gccatcaagg | acatcaagga | ggccatcgaa | 1080 |
| gaagtgaaaa | ccaggaccat | ccgttcgcct | tacacccccg | acgaacccaa | agagcccatc | 1140 |
| tgggtcatgc | gccaggacat | tagccccaca | agggactgtg | acgaccagag | gcccgtggac | 1200 |
| ggagattctc | cgtctcctgg | cagttcctca | ccctgggtg | ctgagtcatc | aatcacaccc | 1260 |
| cttcatcccg | gtgaccccac | ggaagcctcc | actaataaag | agtcaagaaa | aagcttggct | 1320 |
| tcattcccaa | cctacgttga | agttcctgga | ccctgcgacc | ctgaagactt | gatcgatgga | 1380 |
| attattttg | ctgccaatta | ccttggttcc | actcagctac | tctcagacaa | aactccctcc | 1440 |
| aaaaacgtgc | gcatgatgca | ggcccaggaa | gcagtaagcc | ggatcaagac | ggcccagaaa | 1500 |
| ttagccaaaa | gcaggaagaa | ggctcctgaa | ggcgaatctc | agccaatgac | tgaggtggac | 1560 |
| ctcttcatct | ccacccagag | gatcaaagtg | ttgaatgcag | atacacagga | gcctatgatg | 1620 |
| gaccaccctc | tgaggaccat | ttcctacatc | gcagacattg | gaacatcgt | cgtgctgatg | 1680 |
| gcccgcaggc | ggatgccccg | ctccaactcc | caggagaatg | tggaggcctc | tcacccatcc | 1740 |
| caggatgcaa | aacggcagta | caagatgatc | tgtcatgtct | ttgagtctga | ggacgcccag | 1800 |
| ctgatcgcac | agtccatcgg | gcaggccttc | agcgttgcat | accaggagtt | cctcagggcc | 1860 |
| aacgggatta | acccagaaga | cctgagccag | aaggagtaca | cgcgacctgct | caacacccag | 1920 |
| gacatgtaca | acgatgacct | gatccacttc | tccaagtcgg | aaaactgcaa | agatgtctag | 1980 |

<210> SEQ ID NO 4
<211> LENGTH: 1224
<212> TYPE: DNA

<213> ORGANISM: rattus norvegicus

<400> SEQUENCE: 4

| | | | | |
|---|---|---|---|---|
| atggagcaga | agctgatcag | cgaggaggac | ctgaacggaa | ttcagatctg | gtacccctgc | 60 |
| gaccctgaag | acttgatcga | tggaattatt | tttgctgcca | attaccttgg | ttccactcag | 120 |
| ctactctcag | acaaaactcc | ctccaaaaac | gtgcgcatga | tgcaggccca | ggaagcagta | 180 |
| agccggatca | agacggccca | gaaattagcc | aaaagcagga | agaaggctcc | tgaaggcgaa | 240 |
| tctcagccaa | tgactgaggt | ggacctcttc | atctccaccc | agaggatcaa | agtgttgaat | 300 |
| gcagatacac | aggagcctat | gatggaccac | cctctgagga | ccatttccta | catcgcagac | 360 |
| attgggaaca | tcgtcgtgct | gatggcccgc | aggcggatgc | cccgctccaa | ctcccaggag | 420 |
| aatgtggagg | cctctcaccc | atcccaggat | gcaaaacggc | agtacaagat | gatctgtcat | 480 |
| gtctttgagt | ctgaggacgc | ccagctgatc | gcacagtcca | tcgggcaggc | cttcagcgtt | 540 |
| gcataccagg | agttcctcag | ggccaacggg | attaacccag | aagacctgag | ccagaaggag | 600 |
| tacagcgacc | tgctcaacac | ccaggacatg | tacaacgatg | acctgatcca | cttctccaag | 660 |
| tcggaaaact | gcaaagatgt | cttcatagag | aagcagaaag | gagaaatcct | ggagttgtg | 720 |
| attgtggagt | ctggctgggg | atccattctg | ccaaccgtga | tcattgccaa | catgatgcac | 780 |
| ggaggccccg | ccgagaagtc | ggggaagctg | aacatcgggg | accagatcat | gtccattaac | 840 |
| ggcaccagcc | tggtgggcct | gcccctgtcc | acctgccaga | gcatcattaa | gggcttaaag | 900 |
| aaccagtccc | gcgtgaagct | gaacatcgtg | aggtgccccc | cagtgaccac | agtgctaatt | 960 |
| aggaggccgg | accttcgcta | ccagctgggt | ttcagcgtgc | agaatggaat | tatctgtagc | 1020 |
| ctcatgagag | ggggaatagc | tgagagagga | ggtgtccgcg | tgggacatcg | gatcattgaa | 1080 |
| atcaacggcc | agagtgtcgt | agccacacca | cacgagaaga | tcgtccacat | actctccaat | 1140 |
| gctgttgggg | agatccacat | gaagacaatg | ccagcagcca | tgtacagact | gctgacagcc | 1200 |
| caggagcagc | ccgtttacat | ctga | | | | 1224 |

<210> SEQ ID NO 5
<211> LENGTH: 2253
<212> TYPE: DNA
<213> ORGANISM: rattus norvegicus

<400> SEQUENCE: 5

| | | | | |
|---|---|---|---|---|
| atggcccacc | gcaagcgcca | gagcactgca | agcagcatgt | tggaccacag | ggcccggcca | 60 |
| ggtcctatcc | cccatgacca | ggagcctgag | aatgaggata | cagaactgcc | tctggagagc | 120 |
| tatgtaccca | aggcctgga | gctaggcact | ctgagaccag | acagccccac | gcctgaggaa | 180 |
| caggagtgcc | acaaccatag | ccctgatggg | gactccagct | ctgactatgt | gaacaacacg | 240 |
| tctgaggagg | aggactatga | cgagggcctc | cctgaggagg | aggaaggtgt | cacctactac | 300 |
| atccgctatt | gtcctgagga | tgacagctac | ctggagggca | tggactgtaa | tggggaggag | 360 |
| tacctagccc | atggtgcaca | tcctgtggac | actgatgagt | gtcaggaggc | ggtagaggac | 420 |
| tggacggact | cagtgggtcc | tcatactcat | agccacgggg | ctgaaaacag | ccaagagtat | 480 |
| ccagacagcc | acctgcctat | cccagaggat | gaccсctactg | tcctggaggt | ccatgaccag | 540 |
| gaagaagatg | ccactactg | tcccagcaag | gagagctacc | aggactatta | tcccccagag | 600 |
| accaatggga | acacgggtgg | cgcttctccc | tatcgcatga | ggcgtgggga | tgggaccta | 660 |
| gaggagcagg | aggaagacat | cgaccagata | gtggctgaga | tcaagatgag | cctgagcatg | 720 |
| accagtatta | ccagtgccag | tgaggccagc | cctgagcaca | tgcctgagct | ggaccctggg | 780 |

-continued

```
gactccactg aggcctgttc acccagtgac actggccgtg gacccagtag gcaagaagcg      840
aggcccaagt cgctgaacct tcccctgag gttaagcact ccggagaccc caaagagga       900
ctcaagacca agaccaggac cccagaggag aggccaaagt ggccccaaga gcaggtttgc      960
aatggcttgg aacagccgag gaagcagcag cgctctgatc tcaatggacc cactgacaat    1020
aacaacatcc cagagacaaa gaaggtggcc tcgtttccaa gctttgtagc tgttccaggg    1080
ccctgtgagc cagaagacct catcgatggc atcatctttg cagccaacta cctgggctcc    1140
acccagctgc tctctgagcg caaccccctcc aaaaacatcc gaatgatgca agctcaagaa    1200
gctgtcagca gggtcaagag gatgcagaag gctgctaaga tcaagaaaaa agcgaattct    1260
gagggtgatg ctcagacact gacagaagta gacctcttca tttctaccca gaggatcaaa    1320
gtcttaaacg ctgacacaca ggaaaccatg atggaccatg ccttgcgcac catctcctac    1380
attgcagaca ttgggaacat cgtggttctg atgccaggc gccgcatgcc caggtcagcc    1440
tctcaggact gcatcgagac cacgcctggg gcccaggaag gaagaagca gtacaagatg    1500
atctgtcacg tgttcgagtc agaggatgcc cagctgatag cccagtcaat tgggcaggcc    1560
ttcagtgtgg cctaccagga gttcctgagg gccaacggca tcaaccctga ggacctgagc    1620
cagaaggaat acagtgatat cataaatacc caggagatgt ataatgatga ccttatccac    1680
ttctcaaaact cggagaactg caaggagctg cagctggaga agcacaaggg tgagattttg    1740
ggtgtggtgg tcgtggagtc aggctggggc tccatcctgc ccactgtgat cctggcgaac    1800
atgatgaacg gcggcccagc agctcgctcg gggaagctga gcattggcga ccagatcatg    1860
tccatcaatg gcaccagcct ggtggggctg cccctcgcta cctgccaggg tatcatcaag    1920
ggcctgaaga ccaaacaca ggtaaagctc aacatcgtca gctgtccccc agtcaccaca    1980
gtcctcatca acgtccaga tctcaagtac cagctgggtt tcagcgtgca aaatggaatc    2040
atttgcagcc tcatgagagg gggtattgca gagcgaggtg tgtccgagt cggccaccgt    2100
atcatcgaga tcaacggaca gagtgtggta gccacagccc acgagaagat agtccaggct    2160
ctgtctaact cagttggaga gattcacatg aagaccatgc ctgcagccat gttcaggctc    2220
ctcacaggcc aggagacacc gctgtacatc tag                                 2253
```

<210> SEQ ID NO 6
<211> LENGTH: 2253
<212> TYPE: DNA
<213> ORGANISM: rattus norvegicus

<400> SEQUENCE: 6

```
atggcccacc gcaagcgcca gagcactgca agcagcatgt tggaccacag ggcccggcca      60
ggtcctatcc cccatgacca ggagcctgag aatgaggata cagaactgcc tctggagagc     120
tatgtaccca caggcctgga gctaggcact ctgagaccag acagccccac gcctgaggaa     180
caggagtgcc acaaccatag ccctgatggg gactccagct ctgactatgt gaacaacacg     240
tctgaggagg aggactatga cgagggcctc cctgaggagg aggaaggtgt cacctactac     300
atccgctatt gtcctgagga tgacagctac ctggagggca tggactgtaa tggggaggag     360
tacctagccc atggtgcaca tcctgtggac actgatgagt gtcaggaggc ggtagaggac     420
tggacggact cagtgggtcc tcatactcat agccacgggg ctgaaaacag ccaagagtat     480
ccagacagcc acctgcctat cccagaggat gacctactg tcctggaggt ccatgaccag     540
gaagaagatg gccactactg tcccagcaag gagagctacc aggactatta tcccccagag     600
```

-continued

| | |
|---|---|
| accaatggga acacgggtgg cgcttctccc tatcgcatga ggcgtgggga tggggaccta | 660 |
| gaggagcagg aggaagacat cgaccagata gtggctgaga tcaagatgag cctgagcatg | 720 |
| accagtatta ccagtgccag tgaggccagc cctgagcaca tgcctgagct ggaccctggg | 780 |
| gactccactg aggcctgttc acccagtgac actggccgtg acccagtag gcaagaagcg | 840 |
| aggcccaagt cgctgaacct tcccctgag gttaagcact ccggagaccc caaagagga | 900 |
| ctcaagacca agaccaggac cccagaggag aggccaaagt ggcccaaga gcaggtttgc | 960 |
| aatggcttgg aacagccgag gaagcagcag cgctctgatc tcaatggacc cactgacaat | 1020 |
| aacaacatcc cagagacaaa gaaggtggcc tcgtttccaa gctttgtagc tgttccaggg | 1080 |
| ccctgtgagc cagaagacct catcgatggc atcatctttg cagccaacta cctgggctcc | 1140 |
| acccagctgc tctctgagcg caaccccctcc aaaaacatcc gaatgatgca agctcaagaa | 1200 |
| gctgtcagca gggtcaagag gatgcagaag gctgctaaga tcaagaaaaa agcgaattct | 1260 |
| gagggtgatg ctcagacact gacagaagta gacctcttca tttctaccca gaggatcaaa | 1320 |
| gtcttaaacg ctgacacaca ggaaaccatg atggaccatg ccttgcgcac catctcctac | 1380 |
| attgcagaca ttgggaacat cgtggttctg atggccaggc gccgcatgcc caggtcagcc | 1440 |
| tctcaggact gcatcgagac cacgcctggg gcccaggaag ggaagaagca gtacaagatg | 1500 |
| atctgtcacg tgttcgagtc agaggatgcc cagctgatag cccagtcaat tgggcaggcc | 1560 |
| ttcagtgtgg cctaccagga gttcctgagg gccaacggca tcaaccctga ggacctgagc | 1620 |
| cagaaggaat acagtgatat cataaatacc caggagatgt ataatgatga ccttatccac | 1680 |
| ttctcaaact cggagaactg caaggagctg cagctggaga agcacaaggg tgagattttg | 1740 |
| gcagcagtgg tcgtggagtc aggctggggc tccatcctgc ccactgtgat cctggcgaac | 1800 |
| atgatgaacg gcggcccagc agctcgctcg gggaagctga gcattggcga ccagatcatg | 1860 |
| tccatcaatg gcaccagcct ggtggggctg cccctcgcta cctgccaggg tatcatcaag | 1920 |
| ggcctgaaga accaaacaca ggtaaagctc aacatcgtca gctgtccccc agtcaccaca | 1980 |
| gtcctcatca acgtccaga tctcaagtac cagctgggtt tcagcgtgca aaatggaatc | 2040 |
| atttgcagcc tcatgagagg gggtattgca gagcgaggtg gtgtccgagt cggccaccgt | 2100 |
| atcatcgaga tcaacggaca gagtgtggta gccacagccc acgagaagat agtccaggct | 2160 |
| ctgtctaact cagttggaga gattcacatg aagaccatgc ctgcagccat gttcaggctc | 2220 |
| ctcacaggcc aggagacacc gctgtacatc tag | 2253 |

<210> SEQ ID NO 7
<211> LENGTH: 1713
<212> TYPE: DNA
<213> ORGANISM: rattus norvegicus

<400> SEQUENCE: 7

| | |
|---|---|
| atggcccacc gcaagcgcca gagcactgca agcagcatgt ggaccacag ggcccggcca | 60 |
| ggtcctatcc cccatgacca ggagcctgag aatgaggata cagaactgcc tctggagagc | 120 |
| tatgtaccca caggcctgga gctaggcact ctgagaccag acagccccac gcctgaggaa | 180 |
| caggagtgcc acaaccatag ccctgatggg gactccagct ctgactatgt gaacaacacg | 240 |
| tctgaggagg aggactatga cgagggcctc cctgaggagg aggaaggtgt cacctactac | 300 |
| atccgctatt gtcctgagga tgacagctac ctggagggca tggactgtaa tgggggaggag | 360 |
| tacctagccc atggtgcaca tcctgtggac actgatgagt gtcaggaggc ggtagaggac | 420 |
| tggacggact cagtgggtcc tcatactcat agccacgggg ctgaaaacag ccaagagtat | 480 |

-continued

```
ccagacagcc acctgcctat cccagaggat gaccctactg tcctggaggt ccatgaccag      540
gaagaagatg ccactactg tcccagcaag gagagctacc aggactatta tcccccagag       600
accaatggga acacggtgg cgcttctccc tatcgcatga ggcgtgggga tggggaccta       660
gaggagcagg aggaagacat cgaccagata gtggctgaga tcaagatgag cctgagcatg     720
accagtatta ccagtgccag tgaggccagc cctgagcaca tgcctgagct ggaccctggg     780
gactccactg aggcctgttc acccagtgac actggccgtg acccagtag caagaagcg       840 aggcccaagt cgctgaacct tccccctgag gttaagcact ccggagaccc caaagagga     900 ctcaagacca agaccaggac cccagaggag aggccaaagt ggccccaaga gcaggtttgc     960
aatggcttgg aacagccgag gaagcagcag cgctctgatc tcaatggacc cactgacaat   1020
aacaacatcc agagacaaa gaaggtggcc tcgtttccaa gctttgtagc tgttccaggg    1080
ccctgtgagc cagaagacct catcgatggc atcatctttg cagccaacta cctgggctcc   1140
acccagctgc tctctgagcg caaccccctcc aaaaacatcc gaatgatgca agctcaagaa   1200
gctgtcagca gggtcaagag gatgcagaag gctgctaaga tcaagaaaaa agcgaattct   1260
gagggtgatg ctcagacact gacagaagta gacctcttca tttctaccca gaggatcaaa   1320
gtcttaaacg ctgacacaca ggaaaccatg atggaccatg ccttgcgcac catctcctac   1380
attgcagaca ttgggaacat cgtggttctg atggccaggc gccgcatgcc caggtcagcc   1440
tctcaggact gcatcgagac cacgcctggg gcccaggaag ggaagaagca gtacaagatg   1500
atctgtcacg tgttcgagtc agaggatgcc cagctgatga cccagtcaat tgggcaggcc   1560
ttcagtgtgg cctaccagga gttcctgagg gccaacggca tcaaccctga ggacctgagc   1620
cagaaggaat acagtgatat cataaatacc caggagatgt ataatgatga ccttatccac   1680 ttctcaaaact cggagaactg caaggagctc tag                                1713
```

<210> SEQ ID NO 8
<211> LENGTH: 1227
<212> TYPE: DNA
<213> ORGANISM: rattus norvegicus

<400> SEQUENCE: 8

```
atggagcaga agctgatcag cgaggaggac ctgaacggaa ttcagatctg gtaccctgt       60 gagccagaag acctcatcga tggcatcatc tttgcagcca actacctggg ctccacccag     120
ctgctctctg agcgcaaccc ctccaaaaac atccgaatga tgcaagctca agaagctgtc     180
agcagggtca agaggatgca gaaggctgct aagatcaaga aaaagcgaa ttctgagggt     240 gatgctcaga cactgacaga agtagacctc ttcatttcta cccagaggat caaagtctta    300
aacgctgaca cacaggaaac catgatggac catgccttgc gcaccatctc ctacattgca    360
gacattggga acatcgtggt tctgatggcc aggcgccgca tgcccaggtc agcctctcag    420
gactgcatcg agaccacgcc tggggcccag gaagggaaga gcagtacaa gatgatctgt     480 cacgtgttcg agtcagagga tgcccagctg atagcccagt caattgggca ggccttcagt    540
gtggcctacc aggagttcct gagggccaac ggcatcaacc tgaggacct gagccagaag    600 gaatacagtg atatcataaa tacccaggag atgtataatg atgacctat ccacttctca     660 aactcggaga actgcaagga gctgcagctg agaagcaca agggtgagat tttgggtgtg    720
gtggtcgtgg agtcaggctg ggctccatc ctgcccactg tgatcctggc gaacatgatg    780
aacggcggcc cagcagctcg ctcggggaag ctgagcattg cgaccagat catgtccatc    840
```

-continued

```
aatggcacca gcctggtggg gctgcccctc gctacctgcc agggtatcat caagggcctg      900
aagaaccaaa cacaggtaaa gctcaacatc gtcagctgtc ccccagtcac acagtcctc      960 atcaaacgtc cagatctcaa gtaccagctg ggtttcagcg tgcaaaatgg aatcatttgc     1020
agcctcatga gaggggtat tgcagagcga ggtggtgtcc gagtcggcca ccgtatcatc     1080
gagatcaacg acagagtgt ggtagccaca gcccacgaga agatagtcca ggctctgtct     1140
aactcagttg gagagattca catgaagacc atgcctgcag ccatgttcag gctcctcaca     1200
ggccaggaga caccgctgta catctag                                         1227
```

<210> SEQ ID NO 9
<211> LENGTH: 839
<212> TYPE: PRT
<213> ORGANISM: rattus norvegicus

<400> SEQUENCE: 9

```
Met Asn His Leu Glu Gly Ser Ala Glu Val Glu Val Ala Asp Glu Ala
 1               5                  10                  15

Pro Gly Gly Glu Val Asn Glu Ser Val Glu Ala Asp Leu Glu His Pro
            20                  25                  30

Glu Val Glu Glu Glu Gln Gln Pro Ser Pro Pro Pro Ala Gly His
        35                  40                  45

Ala Pro Glu Asp His Arg Ala His Pro Ala Pro Pro Pro Pro Pro
    50                  55                  60

Pro Gln Glu Glu Glu Glu Arg Gly Glu Cys Leu Ala Arg Ser Ala
65                  70                  75                  80

Ser Thr Glu Ser Gly Phe His Asn His Thr Asp Thr Ala Glu Gly Asp
                85                  90                  95

Val Leu Ala Ala Ala Arg Asp Gly Tyr Glu Ala Glu Arg Ala Gln Asp
            100                 105                 110

Ala Asp Asp Glu Ser Ala Tyr Ala Val Gln Tyr Arg Pro Glu Ala Glu
        115                 120                 125

Glu Tyr Thr Glu Gln Ala Glu Ala Glu His Ala Glu Ala Ala Gln Arg
    130                 135                 140

Arg Ala Leu Pro Asn His Leu His Phe His Ser Leu Glu His Glu Glu
145                 150                 155                 160

Ala Met Asn Ala Ala Tyr Ser Gly Tyr Val Tyr Thr His Arg Leu Phe
                165                 170                 175

His Arg Ala Glu Asp Glu Pro Tyr Ala Glu Pro Tyr Ala Asp Tyr Gly
            180                 185                 190

Gly Leu Gln Glu His Val Tyr Glu Glu Ile Gly Asp Ala Pro Glu Leu
        195                 200                 205

Glu Ala Arg Asp Gly Leu Arg Leu Tyr Glu Arg Glu Arg Asp Glu Ala
    210                 215                 220

Ala Ala Tyr Arg Gln Glu Ala Leu Gly Ala Arg Leu His His Tyr Asp
225                 230                 235                 240

Glu Arg Ser Asp Gly Glu Ser Asp Ser Pro Glu Lys Glu Ala Glu Phe
                245                 250                 255

Ala Pro Tyr Pro Arg Met Asp Ser Tyr Glu Gln Glu Glu Asp Ile Asp
            260                 265                 270

Gln Ile Val Ala Glu Val Lys Gln Ser Met Ser Ser Gln Ser Leu Asp
        275                 280                 285

Lys Ala Ala Glu Asp Met Pro Glu Ala Glu Gln Asp Leu Glu Arg Ala
    290                 295                 300
```

-continued

```
Pro Thr Pro Gly Gly Gly His Pro Asp Ser Pro Gly Leu Pro Ala Pro
305                 310                 315                 320

Ala Gly Gln Gln Gln Arg Val Val Gly Thr Pro Gly Gly Ser Glu Val
            325                 330                 335

Gly Gln Arg Tyr Ser Lys Glu Lys Arg Asp Ala Ile Ser Leu Ala Ile
                340                 345                 350

Lys Asp Ile Lys Glu Ala Ile Glu Glu Val Lys Thr Arg Thr Ile Arg
            355                 360                 365

Ser Pro Tyr Thr Pro Asp Glu Pro Lys Glu Pro Ile Trp Val Met Arg
    370                 375                 380

Gln Asp Ile Ser Pro Thr Arg Asp Cys Asp Asp Gln Arg Pro Val Asp
385                 390                 395                 400

Gly Asp Ser Pro Ser Pro Gly Ser Ser Ser Pro Leu Gly Ala Glu Ser
                405                 410                 415

Ser Ile Thr Pro Leu His Pro Gly Asp Pro Thr Glu Ala Ser Thr Asn
            420                 425                 430

Lys Glu Ser Arg Lys Ser Leu Ala Ser Phe Pro Thr Tyr Val Glu Val
            435                 440                 445

Pro Gly Pro Cys Asp Pro Glu Asp Leu Ile Asp Gly Ile Ile Phe Ala
    450                 455                 460

Ala Asn Tyr Leu Gly Ser Thr Gln Leu Leu Ser Asp Lys Thr Pro Ser
465                 470                 475                 480

Lys Asn Val Arg Met Met Gln Ala Gln Glu Ala Val Ser Arg Ile Lys
                485                 490                 495

Thr Ala Gln Lys Leu Ala Lys Ser Arg Lys Lys Ala Pro Glu Gly Glu
            500                 505                 510

Ser Gln Pro Met Thr Glu Val Asp Leu Phe Ile Ser Thr Gln Arg Ile
    515                 520                 525

Lys Val Leu Asn Ala Asp Thr Gln Glu Pro Met Met Asp His Pro Leu
530                 535                 540

Arg Thr Ile Ser Tyr Ile Ala Asp Ile Gly Asn Ile Val Val Leu Met
545                 550                 555                 560

Ala Arg Arg Arg Met Pro Arg Ser Asn Ser Gln Glu Asn Val Glu Ala
                565                 570                 575

Ser His Pro Ser Gln Asp Ala Lys Arg Gln Tyr Lys Met Ile Cys His
            580                 585                 590

Val Phe Glu Ser Glu Asp Ala Gln Leu Ile Ala Gln Ser Ile Gly Gln
    595                 600                 605

Ala Phe Ser Val Ala Tyr Gln Glu Phe Leu Arg Ala Asn Gly Ile Asn
610                 615                 620

Pro Glu Asp Leu Ser Gln Lys Glu Tyr Ser Asp Leu Leu Asn Thr Gln
625                 630                 635                 640

Asp Met Tyr Asn Asp Asp Leu Ile His Phe Ser Lys Ser Glu Asn Cys
                645                 650                 655

Lys Asp Val Phe Ile Glu Lys Gln Lys Gly Glu Ile Leu Gly Val Val
            660                 665                 670

Ile Val Glu Ser Gly Trp Gly Ser Ile Leu Pro Thr Val Ile Ile Ala
    675                 680                 685

Asn Met Met His Gly Gly Pro Ala Glu Lys Ser Gly Lys Leu Asn Ile
690                 695                 700

Gly Asp Gln Ile Met Ser Ile Asn Gly Thr Ser Leu Val Gly Leu Pro
705                 710                 715                 720

Leu Ser Thr Cys Gln Ser Ile Ile Lys Gly Leu Lys Asn Gln Ser Arg
```

```
                725                 730                 735
Val Lys Leu Asn Ile Val Arg Cys Pro Val Thr Thr Val Leu Ile
            740                 745                 750

Arg Arg Pro Asp Leu Arg Tyr Gln Leu Gly Phe Ser Val Gln Asn Gly
            755                 760                 765

Ile Ile Cys Ser Leu Met Arg Gly Gly Ile Ala Glu Arg Gly Gly Val
            770                 775                 780

Arg Val Gly His Arg Ile Ile Glu Ile Asn Gly Gln Ser Val Val Ala
785                 790                 795                 800

Thr Pro His Glu Lys Ile Val His Ile Leu Ser Asn Ala Val Gly Glu
            805                 810                 815

Ile His Met Lys Thr Met Pro Ala Ala Met Tyr Arg Leu Leu Thr Ala
            820                 825                 830

Gln Glu Gln Pro Val Tyr Ile
            835

<210> SEQ ID NO 10
<211> LENGTH: 839
<212> TYPE: PRT
<213> ORGANISM: rattus norvegicus

<400> SEQUENCE: 10

Met Asn His Leu Glu Gly Ser Ala Glu Val Glu Val Ala Asp Glu Ala
1               5                   10                  15

Pro Gly Gly Glu Val Asn Glu Ser Val Glu Ala Asp Leu Glu His Pro
            20                  25                  30

Glu Val Glu Glu Glu Gln Gln Pro Ser Pro Pro Pro Ala Gly His
        35                  40                  45

Ala Pro Glu Asp His Arg Ala His Pro Ala Pro Pro Pro Pro Pro
    50                  55                  60

Pro Gln Glu Glu Glu Glu Arg Gly Glu Cys Leu Ala Arg Ser Ala
65                  70                  75                  80

Ser Thr Glu Ser Gly Phe His Asn His Thr Asp Thr Ala Glu Gly Asp
                85                  90                  95

Val Leu Ala Ala Ala Arg Asp Gly Tyr Glu Ala Glu Arg Ala Gln Asp
            100                 105                 110

Ala Asp Asp Glu Ser Ala Tyr Ala Val Gln Tyr Arg Pro Glu Ala Glu
            115                 120                 125

Glu Tyr Thr Glu Gln Ala Glu Ala Glu His Ala Glu Ala Ala Gln Arg
        130                 135                 140

Arg Ala Leu Pro Asn His Leu His Phe His Ser Leu Glu His Glu Glu
145                 150                 155                 160

Ala Met Asn Ala Ala Tyr Ser Gly Tyr Val Tyr Thr His Arg Leu Phe
                165                 170                 175

His Arg Ala Glu Asp Glu Pro Tyr Ala Glu Pro Tyr Ala Asp Tyr Gly
            180                 185                 190

Gly Leu Gln Glu His Val Tyr Glu Glu Ile Gly Asp Ala Pro Glu Leu
        195                 200                 205

Glu Ala Arg Asp Gly Leu Arg Leu Tyr Glu Arg Glu Arg Asp Glu Ala
    210                 215                 220

Ala Ala Tyr Arg Gln Glu Ala Leu Gly Ala Arg Leu His His Tyr Asp
225                 230                 235                 240

Glu Arg Ser Asp Gly Glu Ser Asp Ser Pro Glu Lys Glu Ala Glu Phe
                245                 250                 255
```

```
Ala Pro Tyr Pro Arg Met Asp Ser Tyr Glu Gln Glu Asp Ile Asp
            260                 265                 270

Gln Ile Val Ala Glu Val Lys Gln Ser Met Ser Ser Gln Ser Leu Asp
        275                 280                 285

Lys Ala Ala Glu Asp Met Pro Glu Ala Glu Gln Asp Leu Glu Arg Ala
290                 295                 300

Pro Thr Pro Gly Gly Gly His Pro Asp Ser Pro Gly Leu Pro Ala Pro
305                 310                 315                 320

Ala Gly Gln Gln Gln Arg Val Val Gly Thr Pro Gly Gly Ser Glu Val
            325                 330                 335

Gly Gln Arg Tyr Ser Lys Glu Lys Arg Asp Ala Ile Ser Leu Ala Ile
            340                 345                 350

Lys Asp Ile Lys Glu Ala Ile Glu Glu Val Lys Thr Arg Thr Ile Arg
        355                 360                 365

Ser Pro Tyr Thr Pro Asp Glu Pro Lys Glu Pro Ile Trp Val Met Arg
    370                 375                 380

Gln Asp Ile Ser Pro Thr Arg Asp Cys Asp Asp Gln Arg Pro Val Asp
385                 390                 395                 400

Gly Asp Ser Pro Ser Pro Gly Ser Ser Pro Leu Gly Ala Glu Ser
            405                 410                 415

Ser Ile Thr Pro Leu His Pro Gly Asp Pro Thr Glu Ala Ser Thr Asn
        420                 425                 430

Lys Glu Ser Arg Lys Ser Leu Ala Ser Phe Pro Thr Tyr Val Glu Val
            435                 440                 445

Pro Gly Pro Cys Asp Pro Glu Asp Leu Ile Asp Gly Ile Ile Phe Ala
        450                 455                 460

Ala Asn Tyr Leu Gly Ser Thr Gln Leu Leu Ser Asp Lys Thr Pro Ser
465                 470                 475                 480

Lys Asn Val Arg Met Met Gln Ala Gln Glu Ala Val Ser Arg Ile Lys
            485                 490                 495

Thr Ala Gln Lys Leu Ala Lys Ser Arg Lys Lys Ala Pro Glu Gly Glu
            500                 505                 510

Ser Gln Pro Met Thr Glu Val Asp Leu Phe Ile Ser Thr Gln Arg Ile
        515                 520                 525

Lys Val Leu Asn Ala Asp Thr Gln Glu Pro Met Met Asp His Pro Leu
530                 535                 540

Arg Thr Ile Ser Tyr Ile Ala Asp Ile Gly Asn Ile Val Val Leu Met
545                 550                 555                 560

Ala Arg Arg Arg Met Pro Arg Ser Asn Ser Gln Glu Asn Val Glu Ala
            565                 570                 575

Ser His Pro Ser Gln Asp Ala Lys Arg Gln Tyr Lys Met Ile Cys His
        580                 585                 590

Val Phe Glu Ser Glu Asp Ala Gln Leu Ile Ala Gln Ser Ile Gly Gln
    595                 600                 605

Ala Phe Ser Val Ala Tyr Gln Glu Phe Leu Arg Ala Asn Gly Ile Asn
610                 615                 620

Pro Glu Asp Leu Ser Gln Lys Glu Tyr Ser Asp Leu Leu Asn Thr Gln
625                 630                 635                 640

Asp Met Tyr Asn Asp Asp Leu Ile His Phe Ser Lys Ser Glu Asn Cys
            645                 650                 655

Lys Asp Val Phe Ile Glu Lys Gln Lys Gly Glu Ile Leu Ala Ala Val
            660                 665                 670

Ile Val Glu Ser Gly Trp Gly Ser Ile Leu Pro Thr Val Ile Ile Ala
```

-continued

```
            675                 680                 685
Asn Met Met His Gly Pro Ala Glu Lys Ser Gly Lys Leu Asn Ile
        690                 695                 700
Gly Asp Gln Ile Met Ser Ile Asn Gly Thr Ser Leu Val Gly Leu Pro
705                 710                 715                 720
Leu Ser Thr Cys Gln Ser Ile Ile Lys Gly Leu Lys Asn Gln Ser Arg
                725                 730                 735
Val Lys Leu Asn Ile Val Arg Cys Pro Val Thr Thr Val Leu Ile
                740                 745                 750
Arg Arg Pro Asp Leu Arg Tyr Gln Leu Gly Phe Ser Val Gln Asn Gly
            755                 760                 765
Ile Ile Cys Ser Leu Met Arg Gly Gly Ile Ala Glu Arg Gly Gly Val
        770                 775                 780
Arg Val Gly His Arg Ile Ile Glu Ile Asn Gly Gln Ser Val Val Ala
785                 790                 795                 800
Thr Pro His Glu Lys Ile Val His Ile Leu Ser Asn Ala Val Gly Glu
                805                 810                 815
Ile His Met Lys Thr Met Pro Ala Ala Met Tyr Arg Leu Leu Thr Ala
            820                 825                 830
Gln Glu Gln Pro Val Tyr Ile
            835

<210> SEQ ID NO 11
<211> LENGTH: 659
<212> TYPE: PRT
<213> ORGANISM: rattus norvegicus

<400> SEQUENCE: 11

Met Asn His Leu Glu Gly Ser Ala Glu Val Glu Ala Asp Glu Ala
1               5                   10                  15
Pro Gly Gly Glu Val Asn Glu Ser Val Glu Ala Asp Leu Glu His Pro
                20                  25                  30
Glu Val Glu Glu Glu Gln Gln Pro Ser Pro Pro Pro Ala Gly His
            35                  40                  45
Ala Pro Glu Asp His Arg Ala His Pro Ala Pro Pro Pro Pro Pro
50                  55                  60
Pro Gln Glu Glu Glu Glu Arg Gly Glu Cys Leu Ala Arg Ser Ala
65                  70                  75                  80
Ser Thr Glu Ser Gly Phe His Asn His Thr Asp Thr Ala Glu Gly Asp
                85                  90                  95
Val Leu Ala Ala Ala Arg Asp Gly Tyr Glu Ala Glu Arg Ala Gln Asp
                100                 105                 110
Ala Asp Asp Glu Ser Ala Tyr Ala Val Gln Tyr Arg Pro Glu Ala Glu
            115                 120                 125
Glu Tyr Thr Glu Gln Ala Glu Ala Glu His Ala Glu Ala Ala Gln Arg
        130                 135                 140
Arg Ala Leu Pro Asn His Leu His Phe His Ser Leu Glu His Glu Glu
145                 150                 155                 160
Ala Met Asn Ala Ala Tyr Ser Gly Tyr Val Tyr Thr His Arg Leu Phe
                165                 170                 175
His Arg Ala Glu Asp Glu Pro Tyr Ala Glu Pro Tyr Ala Asp Tyr Gly
                180                 185                 190
Gly Leu Gln Glu His Val Tyr Glu Glu Ile Gly Asp Ala Pro Glu Leu
            195                 200                 205
```

-continued

Glu Ala Arg Asp Gly Leu Arg Leu Tyr Glu Arg Glu Arg Asp Glu Ala
210                 215                 220

Ala Ala Tyr Arg Gln Glu Ala Leu Gly Ala Arg Leu His His Tyr Asp
225                 230                 235                 240

Glu Arg Ser Asp Gly Glu Ser Asp Ser Pro Glu Lys Glu Ala Glu Phe
                245                 250                 255

Ala Pro Tyr Pro Arg Met Asp Ser Tyr Glu Gln Glu Glu Asp Ile Asp
            260                 265                 270

Gln Ile Val Ala Glu Val Lys Gln Ser Met Ser Ser Gln Ser Leu Asp
        275                 280                 285

Lys Ala Ala Glu Asp Met Pro Glu Ala Glu Gln Asp Leu Glu Arg Ala
290                 295                 300

Pro Thr Pro Gly Gly Gly His Pro Asp Ser Pro Gly Leu Pro Ala Pro
305                 310                 315                 320

Ala Gly Gln Gln Gln Arg Val Val Gly Thr Pro Gly Gly Ser Glu Val
                325                 330                 335

Gly Gln Arg Tyr Ser Lys Glu Lys Arg Asp Ala Ile Ser Leu Ala Ile
            340                 345                 350

Lys Asp Ile Lys Glu Ala Ile Glu Glu Val Lys Thr Arg Thr Ile Arg
        355                 360                 365

Ser Pro Tyr Thr Pro Asp Glu Pro Lys Glu Pro Ile Trp Val Met Arg
370                 375                 380

Gln Asp Ile Ser Pro Thr Arg Asp Cys Asp Asp Gln Arg Pro Val Asp
385                 390                 395                 400

Gly Asp Ser Pro Ser Pro Gly Ser Ser Ser Pro Leu Gly Ala Glu Ser
                405                 410                 415

Ser Ile Thr Pro Leu His Pro Gly Asp Pro Thr Glu Ala Ser Thr Asn
            420                 425                 430

Lys Glu Ser Arg Lys Ser Leu Ala Ser Phe Pro Thr Tyr Val Glu Val
        435                 440                 445

Pro Gly Pro Cys Asp Pro Glu Asp Leu Ile Asp Gly Ile Ile Phe Ala
450                 455                 460

Ala Asn Tyr Leu Gly Ser Thr Gln Leu Leu Ser Asp Lys Thr Pro Ser
465                 470                 475                 480

Lys Asn Val Arg Met Met Gln Ala Gln Glu Ala Val Ser Arg Ile Lys
                485                 490                 495

Thr Ala Gln Lys Leu Ala Lys Ser Arg Lys Lys Ala Pro Glu Gly Glu
            500                 505                 510

Ser Gln Pro Met Thr Glu Val Asp Leu Phe Ile Ser Thr Gln Arg Ile
        515                 520                 525

Lys Val Leu Asn Ala Asp Thr Gln Glu Pro Met Met Asp His Pro Leu
530                 535                 540

Arg Thr Ile Ser Tyr Ile Ala Asp Ile Gly Asn Ile Val Val Leu Met
545                 550                 555                 560

Ala Arg Arg Arg Met Pro Arg Ser Asn Ser Gln Glu Asn Val Glu Ala
                565                 570                 575

Ser His Pro Ser Gln Asp Ala Lys Arg Gln Tyr Lys Met Ile Cys His
            580                 585                 590

Val Phe Glu Ser Glu Asp Ala Gln Leu Ile Ala Gln Ser Ile Gly Gln
        595                 600                 605

Ala Phe Ser Val Ala Tyr Gln Glu Phe Leu Arg Ala Asn Gly Ile Asn
610                 615                 620

Pro Glu Asp Leu Ser Gln Lys Glu Tyr Ser Asp Leu Leu Asn Thr Gln

```
                    625                 630                 635                 640
Asp Met Tyr Asn Asp Asp Leu Ile His Phe Ser Lys Ser Glu Asn Cys
                    645                 650                 655
Lys Asp Val

<210> SEQ ID NO 12
<211> LENGTH: 407
<212> TYPE: PRT
<213> ORGANISM: rattus norvegicus

<400> SEQUENCE: 12

Met Glu Gln Lys Leu Ile Ser Glu Glu Asp Leu Asn Gly Ile Gln Ile
1               5                   10                  15

Trp Tyr Pro Cys Asp Pro Glu Asp Leu Ile Asp Gly Ile Ile Phe Ala
            20                  25                  30

Ala Asn Tyr Leu Gly Ser Thr Gln Leu Leu Ser Asp Lys Thr Pro Ser
        35                  40                  45

Lys Asn Val Arg Met Met Gln Ala Gln Glu Ala Val Ser Arg Ile Lys
    50                  55                  60

Thr Ala Gln Lys Leu Ala Lys Ser Arg Lys Lys Ala Pro Glu Gly Glu
65                  70                  75                  80

Ser Gln Pro Met Thr Glu Val Asp Leu Phe Ile Ser Thr Gln Arg Ile
                85                  90                  95

Lys Val Leu Asn Ala Asp Thr Gln Glu Pro Met Met Asp His Pro Leu
            100                 105                 110

Arg Thr Ile Ser Tyr Ile Ala Asp Ile Gly Asn Ile Val Val Leu Met
        115                 120                 125

Ala Arg Arg Arg Met Pro Arg Ser Asn Ser Gln Glu Asn Val Glu Ala
    130                 135                 140

Ser His Pro Ser Gln Asp Ala Lys Arg Gln Tyr Lys Met Ile Cys His
145                 150                 155                 160

Val Phe Glu Ser Glu Asp Ala Gln Leu Ile Ala Gln Ser Ile Gly Gln
                165                 170                 175

Ala Phe Ser Val Ala Tyr Gln Glu Phe Leu Arg Ala Asn Gly Ile Asn
            180                 185                 190

Pro Glu Asp Leu Ser Gln Lys Glu Tyr Ser Asp Leu Leu Asn Thr Gln
        195                 200                 205

Asp Met Tyr Asn Asp Asp Leu Ile His Phe Ser Lys Ser Glu Asn Cys
    210                 215                 220

Lys Asp Val Phe Ile Glu Lys Gln Lys Gly Glu Ile Leu Gly Val Val
225                 230                 235                 240

Ile Val Glu Ser Gly Trp Gly Ser Ile Leu Pro Thr Val Ile Ile Ala
                245                 250                 255

Asn Met Met His Gly Gly Pro Ala Glu Lys Ser Gly Lys Leu Asn Ile
            260                 265                 270

Gly Asp Gln Ile Met Ser Ile Asn Gly Thr Ser Leu Val Gly Leu Pro
        275                 280                 285

Leu Ser Thr Cys Gln Ser Ile Ile Lys Gly Leu Lys Asn Gln Ser Arg
    290                 295                 300

Val Lys Leu Asn Ile Val Arg Cys Pro Pro Val Thr Thr Val Leu Ile
305                 310                 315                 320

Arg Arg Pro Asp Leu Arg Tyr Gln Leu Gly Phe Ser Val Gln Asn Gly
                325                 330                 335

Ile Ile Cys Ser Leu Met Arg Gly Gly Ile Ala Glu Arg Gly Gly Val
```

340                 345                 350
Arg Val Gly His Arg Ile Ile Glu Ile Asn Gly Gln Ser Val Val Ala
            355                 360                 365

Thr Pro His Glu Lys Ile Val His Ile Leu Ser Asn Ala Val Gly Glu
    370                 375                 380

Ile His Met Lys Thr Met Pro Ala Ala Met Tyr Arg Leu Leu Thr Ala
385                 390                 395                 400

Gln Glu Gln Pro Val Tyr Ile
                405

<210> SEQ ID NO 13
<211> LENGTH: 750
<212> TYPE: PRT
<213> ORGANISM: rattus norvegicus

<400> SEQUENCE: 13

Met Ala His Arg Lys Arg Gln Ser Thr Ala Ser Ser Met Leu Asp His
1               5                   10                  15

Arg Ala Arg Pro Gly Pro Ile Pro His Asp Gln Glu Pro Glu Asn Glu
            20                  25                  30

Asp Thr Glu Leu Pro Leu Glu Ser Tyr Val Pro Thr Gly Leu Glu Leu
        35                  40                  45

Gly Thr Leu Arg Pro Asp Ser Pro Thr Pro Glu Gln Glu Cys His
    50                  55                  60

Asn His Ser Pro Asp Gly Asp Ser Ser Ser Asp Tyr Val Asn Asn Thr
65                  70                  75                  80

Ser Glu Glu Glu Asp Tyr Asp Glu Gly Leu Pro Glu Glu Glu Gly
                85                  90                  95

Val Thr Tyr Tyr Ile Arg Tyr Cys Pro Glu Asp Asp Ser Tyr Leu Glu
            100                 105                 110

Gly Met Asp Cys Asn Gly Glu Glu Tyr Leu Ala His Gly Ala His Pro
        115                 120                 125

Val Asp Thr Asp Glu Cys Gln Glu Ala Val Glu Asp Trp Thr Asp Ser
    130                 135                 140

Val Gly Pro His Thr His Ser His Gly Ala Glu Asn Ser Gln Glu Tyr
145                 150                 155                 160

Pro Asp Ser His Leu Pro Ile Pro Glu Asp Pro Thr Val Leu Glu
                165                 170                 175

Val His Asp Gln Glu Glu Asp Gly His Tyr Cys Pro Ser Lys Glu Ser
            180                 185                 190

Tyr Gln Asp Tyr Tyr Pro Pro Glu Thr Asn Gly Asn Thr Gly Gly Ala
        195                 200                 205

Ser Pro Tyr Arg Met Arg Arg Gly Asp Gly Asp Leu Glu Glu Gln Glu
    210                 215                 220

Glu Asp Ile Asp Gln Ile Val Ala Glu Ile Lys Met Ser Leu Ser Met
225                 230                 235                 240

Thr Ser Ile Thr Ser Ala Ser Glu Ala Ser Pro Glu His Met Pro Glu
                245                 250                 255

Leu Asp Pro Gly Asp Ser Thr Glu Ala Cys Ser Pro Ser Asp Thr Gly
            260                 265                 270

Arg Gly Pro Ser Arg Gln Glu Ala Arg Pro Lys Ser Leu Asn Leu Pro
        275                 280                 285

Pro Glu Val Lys His Ser Gly Asp Pro Gln Arg Gly Leu Lys Thr Lys
    290                 295                 300

-continued

```
Thr Arg Thr Pro Glu Glu Arg Pro Lys Trp Pro Gln Glu Gln Val Cys
305                 310                 315                 320

Asn Gly Leu Glu Gln Pro Arg Lys Gln Gln Arg Ser Asp Leu Asn Gly
            325                 330                 335

Pro Thr Asp Asn Asn Ile Pro Glu Thr Lys Lys Val Ala Ser Phe
            340                 345                 350

Pro Ser Phe Val Ala Val Pro Gly Pro Cys Glu Pro Glu Asp Leu Ile
            355                 360                 365

Asp Gly Ile Ile Phe Ala Ala Asn Tyr Leu Gly Ser Thr Gln Leu Leu
370                 375                 380

Ser Glu Arg Asn Pro Ser Lys Asn Ile Arg Met Met Gln Ala Gln Glu
385                 390                 395                 400

Ala Val Ser Arg Val Lys Arg Met Gln Lys Ala Ala Lys Ile Lys Lys
                405                 410                 415

Lys Ala Asn Ser Glu Gly Asp Ala Gln Thr Leu Thr Glu Val Asp Leu
            420                 425                 430

Phe Ile Ser Thr Gln Arg Ile Lys Val Leu Asn Ala Asp Thr Gln Glu
            435                 440                 445

Thr Met Met Asp His Ala Leu Arg Thr Ile Ser Tyr Ile Ala Asp Ile
            450                 455                 460

Gly Asn Ile Val Val Leu Met Ala Arg Arg Met Pro Arg Ser Ala
465                 470                 475                 480

Ser Gln Asp Cys Ile Glu Thr Thr Pro Gly Ala Gln Glu Gly Lys Lys
                485                 490                 495

Gln Tyr Lys Met Ile Cys His Val Phe Glu Ser Glu Asp Ala Gln Leu
            500                 505                 510

Ile Ala Gln Ser Ile Gly Gln Ala Phe Ser Val Ala Tyr Gln Glu Phe
            515                 520                 525

Leu Arg Ala Asn Gly Ile Asn Pro Glu Asp Leu Ser Gln Lys Glu Tyr
530                 535                 540

Ser Asp Ile Ile Asn Thr Gln Glu Met Tyr Asn Asp Asp Leu Ile His
545                 550                 555                 560

Phe Ser Asn Ser Glu Asn Cys Lys Glu Leu Gln Leu Glu Lys His Lys
            565                 570                 575

Gly Glu Ile Leu Gly Val Val Val Glu Ser Gly Trp Gly Ser Ile
            580                 585                 590

Leu Pro Thr Val Ile Leu Ala Asn Met Met Asn Gly Gly Pro Ala Ala
            595                 600                 605

Arg Ser Gly Lys Leu Ser Ile Gly Asp Gln Ile Met Ser Ile Asn Gly
610                 615                 620

Thr Ser Leu Val Gly Leu Pro Leu Ala Thr Cys Gln Gly Ile Ile Lys
625                 630                 635                 640

Gly Leu Lys Asn Gln Thr Gln Val Lys Leu Asn Ile Val Ser Cys Pro
                645                 650                 655

Pro Val Thr Thr Val Leu Ile Lys Arg Pro Asp Leu Lys Tyr Gln Leu
            660                 665                 670

Gly Phe Ser Val Gln Asn Gly Ile Ile Cys Ser Leu Met Arg Gly Gly
            675                 680                 685

Ile Ala Glu Arg Gly Gly Val Arg Val Gly His Arg Ile Ile Glu Ile
690                 695                 700

Asn Gly Gln Ser Val Val Ala Thr Ala His Glu Lys Ile Val Gln Ala
705                 710                 715                 720

Leu Ser Asn Ser Val Gly Glu Ile His Met Lys Thr Met Pro Ala Ala
```

```
                      725                 730                 735
Met Phe Arg Leu Leu Thr Gly Gln Glu Thr Pro Leu Tyr Ile
              740                 745                 750

<210> SEQ ID NO 14
<211> LENGTH: 750
<212> TYPE: PRT
<213> ORGANISM: rattus norvegicus

<400> SEQUENCE: 14

Met Ala His Arg Lys Arg Gln Ser Thr Ala Ser Ser Met Leu Asp His
 1               5                  10                  15

Arg Ala Arg Pro Gly Pro Ile Pro His Asp Gln Glu Pro Glu Asn Glu
             20                  25                  30

Asp Thr Glu Leu Pro Leu Glu Ser Tyr Val Pro Thr Gly Leu Glu Leu
         35                  40                  45

Gly Thr Leu Arg Pro Asp Ser Pro Thr Pro Glu Glu Gln Glu Cys His
     50                  55                  60

Asn His Ser Pro Asp Gly Asp Ser Ser Asp Tyr Val Asn Asn Thr
 65                  70                  75                  80

Ser Glu Glu Glu Asp Tyr Asp Glu Gly Leu Pro Glu Glu Glu Gly
                 85                  90                  95

Val Thr Tyr Tyr Ile Arg Tyr Cys Pro Glu Asp Ser Tyr Leu Glu
            100                 105                 110

Gly Met Asp Cys Asn Gly Glu Glu Tyr Leu Ala His Gly Ala His Pro
            115                 120                 125

Val Asp Thr Asp Glu Cys Gln Glu Ala Val Glu Asp Trp Thr Asp Ser
    130                 135                 140

Val Gly Pro His Thr His Ser His Gly Ala Glu Asn Ser Gln Glu Tyr
145                 150                 155                 160

Pro Asp Ser His Leu Pro Ile Pro Glu Asp Asp Pro Thr Val Leu Glu
                165                 170                 175

Val His Asp Gln Glu Glu Asp Gly His Tyr Cys Pro Ser Lys Glu Ser
            180                 185                 190

Tyr Gln Asp Tyr Tyr Pro Pro Glu Thr Asn Gly Asn Thr Gly Gly Ala
        195                 200                 205

Ser Pro Tyr Arg Met Arg Arg Gly Asp Gly Asp Leu Glu Glu Gln Glu
    210                 215                 220

Glu Asp Ile Asp Gln Ile Val Ala Glu Ile Lys Met Ser Leu Ser Met
225                 230                 235                 240

Thr Ser Ile Thr Ser Ala Ser Glu Ala Ser Pro Glu His Met Pro Glu
                245                 250                 255

Leu Asp Pro Gly Asp Ser Thr Glu Ala Cys Ser Pro Ser Asp Thr Gly
            260                 265                 270

Arg Gly Pro Ser Arg Gln Glu Ala Arg Pro Lys Ser Leu Asn Leu Pro
        275                 280                 285

Pro Glu Val Lys His Ser Gly Asp Pro Gln Arg Gly Leu Lys Thr Lys
    290                 295                 300

Thr Arg Thr Pro Glu Glu Arg Pro Lys Trp Pro Gln Glu Gln Val Cys
305                 310                 315                 320

Asn Gly Leu Glu Gln Pro Arg Lys Gln Arg Ser Asp Leu Asn Gly
                325                 330                 335

Pro Thr Asp Asn Asn Asn Ile Pro Glu Thr Lys Lys Val Ala Ser Phe
            340                 345                 350
```

```
Pro Ser Phe Val Ala Val Pro Gly Pro Cys Glu Pro Glu Asp Leu Ile
        355                 360                 365

Asp Gly Ile Ile Phe Ala Ala Asn Tyr Leu Gly Ser Thr Gln Leu Leu
        370                 375                 380

Ser Glu Arg Asn Pro Ser Lys Asn Ile Arg Met Met Gln Ala Gln Glu
385                 390                 395                 400

Ala Val Ser Arg Val Lys Arg Met Gln Lys Ala Ala Lys Ile Lys Lys
                405                 410                 415

Lys Ala Asn Ser Glu Gly Asp Ala Gln Thr Leu Thr Glu Val Asp Leu
            420                 425                 430

Phe Ile Ser Thr Gln Arg Ile Lys Val Leu Asn Ala Asp Thr Gln Glu
        435                 440                 445

Thr Met Met Asp His Ala Leu Arg Thr Ile Ser Tyr Ile Ala Asp Ile
        450                 455                 460

Gly Asn Ile Val Val Leu Met Ala Arg Arg Met Pro Arg Ser Ala
465                 470                 475                 480

Ser Gln Asp Cys Ile Glu Thr Thr Pro Gly Ala Gln Glu Gly Lys Lys
                485                 490                 495

Gln Tyr Lys Met Ile Cys His Val Phe Glu Ser Glu Asp Ala Gln Leu
            500                 505                 510

Ile Ala Gln Ser Ile Gly Gln Ala Phe Ser Val Ala Tyr Gln Glu Phe
        515                 520                 525

Leu Arg Ala Asn Gly Ile Asn Pro Glu Asp Leu Ser Gln Lys Glu Tyr
        530                 535                 540

Ser Asp Ile Ile Asn Thr Gln Glu Met Tyr Asn Asp Asp Leu Ile His
545                 550                 555                 560

Phe Ser Asn Ser Glu Asn Cys Lys Glu Leu Gln Leu Glu Lys His Lys
                565                 570                 575

Gly Glu Ile Leu Ala Ala Val Val Glu Ser Gly Trp Gly Ser Ile
            580                 585                 590

Leu Pro Thr Val Ile Leu Ala Asn Met Met Asn Gly Gly Pro Ala Ala
        595                 600                 605

Arg Ser Gly Lys Leu Ser Ile Gly Asp Gln Ile Met Ser Ile Asn Gly
        610                 615                 620

Thr Ser Leu Val Gly Leu Pro Leu Ala Thr Cys Gln Gly Ile Ile Lys
625                 630                 635                 640

Gly Leu Lys Asn Gln Thr Gln Val Lys Leu Asn Ile Val Ser Cys Pro
                645                 650                 655

Pro Val Thr Thr Val Leu Ile Lys Arg Pro Asp Leu Lys Tyr Gln Leu
            660                 665                 670

Gly Phe Ser Val Gln Asn Gly Ile Ile Cys Ser Leu Met Arg Gly Gly
        675                 680                 685

Ile Ala Glu Arg Gly Gly Val Arg Val Gly His Arg Ile Ile Glu Ile
        690                 695                 700

Asn Gly Gln Ser Val Val Ala Thr Ala His Glu Lys Ile Val Gln Ala
705                 710                 715                 720

Leu Ser Asn Ser Val Gly Glu Ile His Met Lys Thr Met Pro Ala Ala
                725                 730                 735

Met Phe Arg Leu Leu Thr Gly Gln Glu Thr Pro Leu Tyr Ile
            740                 745                 750

<210> SEQ ID NO 15
<211> LENGTH: 570
<212> TYPE: PRT
```

-continued

<213> ORGANISM: rattus norvegicus

<400> SEQUENCE: 15

```
Met Ala His Arg Lys Arg Gln Ser Thr Ala Ser Ser Met Leu Asp His
1               5                   10                  15

Arg Ala Arg Pro Gly Pro Ile Pro His Asp Gln Glu Pro Glu Asn Glu
            20                  25                  30

Asp Thr Glu Leu Pro Leu Glu Ser Tyr Val Pro Thr Gly Leu Glu Leu
        35                  40                  45

Gly Thr Leu Arg Pro Asp Ser Pro Thr Pro Glu Glu Gln Glu Cys His
    50                  55                  60

Asn His Ser Pro Asp Gly Asp Ser Ser Ser Asp Tyr Val Asn Asn Thr
65                  70                  75                  80

Ser Glu Glu Glu Asp Tyr Asp Glu Gly Leu Pro Glu Glu Glu Glu Gly
                85                  90                  95

Val Thr Tyr Tyr Ile Arg Tyr Cys Pro Glu Asp Asp Ser Tyr Leu Glu
            100                 105                 110

Gly Met Asp Cys Asn Gly Glu Glu Tyr Leu Ala His Gly Ala His Pro
        115                 120                 125

Val Asp Thr Asp Glu Cys Gln Glu Ala Val Glu Asp Trp Thr Asp Ser
    130                 135                 140

Val Gly Pro His Thr His Ser His Gly Ala Glu Asn Ser Gln Glu Tyr
145                 150                 155                 160

Pro Asp Ser His Leu Pro Ile Pro Glu Asp Asp Pro Thr Val Leu Glu
                165                 170                 175

Val His Asp Gln Glu Glu Asp Gly His Tyr Cys Pro Ser Lys Glu Ser
            180                 185                 190

Tyr Gln Asp Tyr Tyr Pro Pro Glu Thr Asn Gly Asn Thr Gly Gly Ala
        195                 200                 205

Ser Pro Tyr Arg Met Arg Arg Gly Asp Gly Asp Leu Glu Glu Gln Glu
    210                 215                 220

Glu Asp Ile Asp Gln Ile Val Ala Glu Ile Lys Met Ser Leu Ser Met
225                 230                 235                 240

Thr Ser Ile Thr Ser Ala Ser Glu Ala Ser Pro Glu His Met Pro Glu
                245                 250                 255

Leu Asp Pro Gly Asp Ser Thr Glu Ala Cys Ser Pro Ser Asp Thr Gly
            260                 265                 270

Arg Gly Pro Ser Arg Gln Glu Ala Arg Pro Lys Ser Leu Asn Leu Pro
        275                 280                 285

Pro Glu Val Lys His Ser Gly Asp Pro Gln Arg Gly Leu Lys Thr Lys
    290                 295                 300

Thr Arg Thr Pro Glu Glu Arg Pro Lys Trp Pro Gln Glu Gln Val Cys
305                 310                 315                 320

Asn Gly Leu Glu Gln Pro Arg Lys Gln Arg Ser Asp Leu Asn Gly
                325                 330                 335

Pro Thr Asp Asn Asn Asn Ile Pro Glu Thr Lys Lys Val Ala Ser Phe
            340                 345                 350

Pro Ser Phe Val Ala Val Pro Gly Pro Cys Glu Pro Glu Asp Leu Ile
        355                 360                 365

Asp Gly Ile Ile Phe Ala Ala Asn Tyr Leu Gly Ser Thr Gln Leu Leu
    370                 375                 380

Ser Glu Arg Asn Pro Ser Lys Asn Ile Arg Met Met Gln Ala Gln Glu
385                 390                 395                 400
```

```
Ala Val Ser Arg Val Lys Arg Met Gln Lys Ala Ala Lys Ile Lys Lys
                405                 410                 415

Lys Ala Asn Ser Glu Gly Asp Ala Gln Thr Leu Thr Glu Val Asp Leu
            420                 425                 430

Phe Ile Ser Thr Gln Arg Ile Lys Val Leu Asn Ala Asp Thr Gln Glu
        435                 440                 445

Thr Met Met Asp His Ala Leu Arg Thr Ile Ser Tyr Ile Ala Asp Ile
    450                 455                 460

Gly Asn Ile Val Val Leu Met Ala Arg Arg Met Pro Arg Ser Ala
465                 470                 475                 480

Ser Gln Asp Cys Ile Glu Thr Thr Pro Gly Ala Gln Glu Gly Lys Lys
                485                 490                 495

Gln Tyr Lys Met Ile Cys His Val Phe Glu Ser Glu Asp Ala Gln Leu
            500                 505                 510

Ile Ala Gln Ser Ile Gly Gln Ala Phe Ser Val Ala Tyr Gln Glu Phe
        515                 520                 525

Leu Arg Ala Asn Gly Ile Asn Pro Glu Asp Leu Ser Gln Lys Glu Tyr
    530                 535                 540

Ser Asp Ile Ile Asn Thr Gln Glu Met Tyr Asn Asp Asp Leu Ile His
545                 550                 555                 560

Phe Ser Asn Ser Glu Asn Cys Lys Glu Leu
                565                 570

<210> SEQ ID NO 16
<211> LENGTH: 408
<212> TYPE: PRT
<213> ORGANISM: rattus norvegicus

<400> SEQUENCE: 16

Met Glu Gln Lys Leu Ile Ser Glu Glu Asp Leu Asn Gly Ile Gln Ile
1               5                   10                  15

Trp Tyr Pro Cys Glu Pro Glu Asp Leu Ile Asp Gly Ile Ile Phe Ala
                20                  25                  30

Ala Asn Tyr Leu Gly Ser Thr Gln Leu Leu Ser Glu Arg Asn Pro Ser
            35                  40                  45

Lys Asn Ile Arg Met Met Gln Ala Gln Glu Ala Val Ser Arg Val Lys
    50                  55                  60

Arg Met Gln Lys Ala Ala Lys Ile Lys Lys Ala Asn Ser Glu Gly
65                  70                  75                  80

Asp Ala Gln Thr Leu Thr Glu Val Asp Leu Phe Ile Ser Thr Gln Arg
                85                  90                  95

Ile Lys Val Leu Asn Ala Asp Thr Gln Glu Thr Met Met Asp His Ala
            100                 105                 110

Leu Arg Thr Ile Ser Tyr Ile Ala Asp Ile Gly Asn Ile Val Val Leu
        115                 120                 125

Met Ala Arg Arg Met Pro Arg Ser Ala Ser Gln Asp Cys Ile Glu
    130                 135                 140

Thr Thr Pro Gly Ala Gln Glu Gly Lys Lys Gln Tyr Lys Met Ile Cys
145                 150                 155                 160

His Val Phe Glu Ser Glu Asp Ala Gln Leu Ile Ala Gln Ser Ile Gly
                165                 170                 175

Gln Ala Phe Ser Val Ala Tyr Gln Glu Phe Leu Arg Ala Asn Gly Ile
            180                 185                 190

Asn Pro Glu Asp Leu Ser Gln Lys Glu Tyr Ser Asp Ile Ile Asn Thr
        195                 200                 205
```

```
Gln Glu Met Tyr Asn Asp Asp Leu Ile His Phe Ser Asn Ser Glu Asn
        210                 215                 220

Cys Lys Glu Leu Gln Leu Glu Lys His Lys Gly Glu Ile Leu Gly Val
225                 230                 235                 240

Val Val Val Glu Ser Gly Trp Gly Ser Ile Leu Pro Thr Val Ile Leu
                245                 250                 255

Ala Asn Met Met Asn Gly Gly Pro Ala Ala Arg Ser Gly Lys Leu Ser
                260                 265                 270

Ile Gly Asp Gln Ile Met Ser Ile Asn Gly Thr Ser Leu Val Gly Leu
                275                 280                 285

Pro Leu Ala Thr Cys Gln Gly Ile Ile Lys Gly Leu Lys Asn Gln Thr
                290                 295                 300

Gln Val Lys Leu Asn Ile Val Ser Cys Pro Pro Val Thr Thr Val Leu
305                 310                 315                 320

Ile Lys Arg Pro Asp Leu Lys Tyr Gln Leu Gly Phe Ser Val Gln Asn
                325                 330                 335

Gly Ile Ile Cys Ser Leu Met Arg Gly Gly Ile Ala Glu Arg Gly Gly
                340                 345                 350

Val Arg Val Gly His Arg Ile Ile Glu Ile Asn Gly Gln Ser Val Val
                355                 360                 365

Ala Thr Ala His Glu Lys Ile Val Gln Ala Leu Ser Asn Ser Val Gly
                370                 375                 380

Glu Ile His Met Lys Thr Met Pro Ala Ala Met Phe Arg Leu Leu Thr
385                 390                 395                 400

Gly Gln Glu Thr Pro Leu Tyr Ile
                405

<210> SEQ ID NO 17
<211> LENGTH: 4
<212> TYPE: PRT
<213> ORGANISM: homo sapiens
<220> FEATURE:
<221> NAME/KEY: BINDING
<222> LOCATION: (0)...(0)
<223> OTHER INFORMATION: Binds to PTB binding domain

<400> SEQUENCE: 17

Asn Pro Thr Tyr
1

<210> SEQ ID NO 18
<211> LENGTH: 12
<212> TYPE: PRT
<213> ORGANISM: homo sapiens

<400> SEQUENCE: 18

Cys Met Asp Gln Leu Ala Phe His Gln Phe Tyr Ile
1               5                   10

<210> SEQ ID NO 19
<211> LENGTH: 12
<212> TYPE: PRT
<213> ORGANISM: homo sapiens

<400> SEQUENCE: 19

Cys Met Asp Thr Leu Ala Ser His Gln Leu Tyr Ile
1               5                   10

<210> SEQ ID NO 20
```

```
<211> LENGTH: 12
<212> TYPE: PRT
<213> ORGANISM: drosophila melanogaster

<400> SEQUENCE: 20

Cys Met Glu Asp Leu Ser Ala Lys Gln Val Phe Ile
 1               5                  10

<210> SEQ ID NO 21
<211> LENGTH: 12
<212> TYPE: PRT
<213> ORGANISM: homo sapiens

<400> SEQUENCE: 21

Cys Gly Ser Leu Ile Ser Arg Arg Ala Val Tyr Val
 1               5                  10

<210> SEQ ID NO 22
<211> LENGTH: 12
<212> TYPE: PRT
<213> ORGANISM: homo sapiens

<400> SEQUENCE: 22

Cys Trp Phe Ser Ile Thr Asn Trp Leu Trp Tyr Ile
 1               5                  10

<210> SEQ ID NO 23
<211> LENGTH: 14
<212> TYPE: PRT
<213> ORGANISM: homo sapiens

<400> SEQUENCE: 23

Gln Asn Gly Tyr Glu Asn Pro Thr Tyr Lys Phe Phe Glu Gln
 1               5                  10

<210> SEQ ID NO 24
<211> LENGTH: 14
<212> TYPE: PRT
<213> ORGANISM: homo sapiens

<400> SEQUENCE: 24

Gln Asn Gly Tyr Glu Asn Ala Thr Ala Lys Phe Phe Glu Gln
 1               5                  10
```

METHODS FOR MODULATING TRANSCRIPTIONAL ACTIVATION USING MINT PROTEINS

CROSS REFERENCE TO RELATED APPLICATIONS

This application is continuation-in-part of U.S. patent application Ser. No. 09/821,861 of Südhof et al., filed Mar. 30, 2001 now U.S. Pat. No. 6,649,346 which is incorporated herein by reference.

The subject matter described herein was supported, at least in part, by funds provided by the United States Government. Accordingly, the United States Government may have certain rights to this invention.

INTRODUCTION

The present invention relates to methods for modulating transcriptional activation and hence to methods for the treatment of Alzheimer's disease (AD). The invention is based, at least in part, on the observation that, while all three MsX2-interacting nuclear target (Mint) proteins (Mints 1–3) can bind to the cytoplasmic tail of APP, only Mints 1 and 2 modulate the transcriptional activation mediated by the cytoplasmic tail of APP.

BACKGROUND OF THE INVENTION

Alzheimer's disease (AD) is a degenerative brain disorder that is characterized clinically by progressive loss of memory and cognitive impairment. Pathologically, the disease is characterized by lesions comprising neurofibrillary tangles, cerebrovascular amyloid deposits, and neuritic plaques. The cerebrovascular amyloid deposits and neuritic plaques contain amyloid-β peptide. The aggregation of amyloid-β peptide may be instrumental in the pathogenesis of AD.

Amyloid-β peptide is derived from amyloid-β precursor protein (APP). APP is a ubiquitous type 1 membrane protein (Kang et al., 1987, Nature 325:733–736; Kitaguchi et al., 1988, Nature 331:530–532; Tanzi et al., 1988, Nature 331: 528–30) that is physiologically processed by proteolytic cleavage. (Selkoe, 1998, Trends Cell Biol 8: 447–453; Bayer et al, 1999, Mol Psychiatry 4:524–528; Haass and De Strooper, 1999, Science 286:916–919; Wolfe and Haass, 2001, J Biol Chem 276:5413–5416). First, cleavage by α- or β-secretases releases the large extracellular portion of APP. Subsequently, the remaining sequences of APP composed of a small extracellular stub, the transmembrane region (TMR), and the cytoplasmic tail are digested by γ-secretase at multiple positions. See Sastre et al., 2001, EMBO Rep 2:835–841; Yu et al., 2001, J Biol Chem 276:43756–43760. γ-Cleavage liberates an intracellular cytoplasmic fragment that may be translocated to the nucleus (Cupers et al., 2001, J Neurochem 78:1168–1178; Kimberly et al., 2001, J Biol Chem 276:40288–40292) and may function as a transcriptional activator (Cao and Südhof, 2001, Science 293:115–120; Gao and Pimplikar, 2001, Proc Natl Acad Sci USA 98:14979–14984). In addition, γ-cleavage generates small peptides derived from the TMR and adjacent extracellular sequences that include Aβ340 and Aβ42 which form the amyloid fibrils in Alzheimer's disease. See Glenner and Wong, 1984, Biochem Biophys Res Commun 122:1131–1135; Masters et al, 1985, EMBO J 4:2757–2763; reviewed in Selkoe, 1998, Trends Cell Biol 8: 447–453; Haass and De Strooper, 1999, Science 286:916–919.

The γ-cleavage of APP is mediated by presenilins, intrinsic membrane proteins that may correspond to γ-secretase and that are mutated in some cases of familial AD. See, e.g., Esler et al., 2000, Nat Cell Biol 2:428–434. Also, γ-cleavage occurs in APP homologs that are not implicated in AD. For example, Notch proteins are membrane proteins that are also cleaved in the middle of the TMR in a presenilin-dependent reaction. See, e.g., Yea et al., 1999, Nature 398:525–529; De Strooper et al., 1999, Nature 398:518–522; Struhl et al., 1999, Nature 398:522–525. Notch proteins are cell-surface proteins involved in intercellular signaling in which presenilin-dependent cleavage liberates a cytoplasmic fragment that functions in nuclear transcription. Struhl et al., 2000, Mol Cell 6:625–636. Sterol regulatory element binding proteins (SREPPs) are also cleaved to generate nuclear transcription factors. Brown et al., 2000, Cell 100:391–398. These observations suggested that the short cytoplasmic tail fragment of APP also may function as a transcriptional activator, and that feedback loops may exist between the nucleus and the cytoplasm or cell membrane whereby the rate of APP proteolysis is regulated.

This first of these hypotheses was confirmed by the findings that the short cytoplasmic tail of APP contains an NPTY (SEQ ID NO: 17) sequence that binds to phosphotyrosine binding (PTB) domains in multiple proteins, including Fe65 and Mints/X11a. See Fiore et al., 1995, J Biol Chem 270:30853–30856; Borg et al., 1996, Mol Cell Biol 16:6229–6241; Guenette et al., 1996, Proc Natl Acad Sci USA 93:10832–10837; McLoughlin and Miller, 1996, FEBS Lett 397:197–200; Zhang et al., 1997, EMBO J. 16: 6141–6150. Fe65 is an adaptor protein that forms a transcriptionally active complex with the released APP tail and a nuclear histone acetyltransferase, Tip60. See Cao and Südhof, 2001, Science 293:115–120.

In published U.S. patent application 20010034884, Peraus modified APP to create an APP fusion protein that incorporated a Gal4 binding domain and a VP16 transactivating domain, so that the rate of formation of the cytoplasmic tail of APP could be monitored by measuring the level of expression of a reporter gene whose transcription was controlled by a regulatable promoter containing Gal 4 binding sites. However, in contrast to the study of Cao and Südhof (2001), Peraus expressed no appreciation that the cytoplasmic tail of APP, without modification, acted as a transcription factor under physiological conditions, through an interaction with Fe65 and Tip60.

As introduced above, the NPTY sequence in the cytoplasmic tail fragment of APP can facilitate the binding of this protein to the PTB domains that are present in proteins of the Mints/X 11 family. Mints 1 and 2 are genes initially identified as candidates for Friedreich's ataxia. Based on partial sequence analysis, these genes were thought to be orthologs. See Duclos and Koenig, 1995, Mamm Genome 6: 57–58. However, the sequencing of full-length cDNAs showed that the encoded proteins were products of distinct genes. See Okamoto and Sühof, 1997, J Biol Chem 272: 31459–31464. To prevent confusion among different types of X11s, these proteins were named Mints 1 and 2. A third isoform was dubbed Mint 3. See Okamoto and Südhof, 1997, J Biol Chem 272:31459–31464; Okamoto and Südhof, 1998, Eur J Cell Biol 77:161–165. Subsequent recloning of the same proteins led to further renaming, and they are now also variably referred to as X11α/β/γ, mLin-10s, X11a/b/c, or X11L1/L2.

Mints/X11 proteins are composed of a long isoform-specific N-terminal sequence, a central PTB domain, and two C-terminal PSD-95, *Drosophila* disc large, zona occludens (PDZ) domains. Mint proteins interact with several other proteins in addition to APP. Mint 1 (but not Mints 2 or 3) binds to calcium/calmodulin-dependent serine protein kinase (CASK) (Butz et al., 1998, Cell 94:773–782), another adaptor protein (Hata et al., 1996, J Neurosci 16: 2488–2494). In *C. elegans*, CASK and Mint 1 homologs are encoded by the Lin-2 and Lin-10 genes whose mutation causes similar vulvaless phenotypes, suggesting that the Mint 1/CASK complex is evolutionarily conserved. See Butz et al., 1998, Cell 94:773–782; Kaech et al., 1998, Cell 94:761–771; Borg et al., 1998b, J Biol Chem 273:31633–31636; and Borg et Al., 1999, J Neurosci 19:1307–1316. Mints 1 and 2 also bind to Munc18-1, an essential fusion protein at the, synapse (Okamoto and Südhof, 1997, J Biol Chem 272:31459–31464; Biederer and Südhof, 2000, J Biol Chem. 275:39803–39806; Verhage et al., 2000, Science 287:864–869), and to presenilins which are intrinsic components of the γ-secretase (Lau et al., 2000, Mol Cell Neurosci 16:557–565).

The functions of the mint proteins remain obscure. In *C. elegans*, Lin-10 (Mint 1) mediates the correct targeting of EGF-like receptors to the basolateral membrane of vulval precursor cells (Whitfield et al., 1999, Mol Biol Cell 10:2087–2100), and is necessary for delivery of AMPA-like glutamate receptors to synapses (Rongo et al., 1998, Cell 94:751–759). These data suggest that Lin-10/Mint 1 functions in membrane traffic of proteins to specific plasma membrane domains. In vertebrates, however, a variety of somewhat contradictory functions for Mints have been proposed. Transfection experiments revealed that Mints alter production of Aβ peptides, indicating a role in APP cleavage. See Borg et al., 1998a, J Biol Chem 273:14761–14766; Sastre et al., 1998, J Biol Chem 273:22351–22357; Mueller et al., 2000, J Biol Chem 275:39302–39306. In contrast, an interaction of Mint 1 with KIF17 in vitro led to the proposal that Mint 1 functions in trafficking neuronal NMDA-, but not AMPA-type glutamate receptors in vertebrates. See Setou et al., 2000, Science 288:1796–1802. This study renamed Mint 1 "mLin-10" in analogy to the *C. elegans* gene, but did not reference the previous finding that in nematodes Lin-10 only affects AMPA- but not NMDA-receptors (Rongo et al., 1998, Cell 94:751–759).

The small size of the APP cytodomain and the overlapping of its regions involved in the binding of Fe65 and the Mints proteins suggest that the latter may be involved in the competitive regulation of the intracellular signaling events mediated by the cytoplasmic tail of APP. Because it is likely that the rate of APP proteolysis is directly or indirectly regulated through feedback mechanisms that operate between the nucleus and the cytoplasm or cell membrane, a better understanding of the interactions between the cytoplasmic tail of APP and the Mints proteins will expand our knowledge of the mechanisms whereby the rate of APP proteolysis is regulated, thereby leading to greater insight into the pathophysiology of AD.

These studies may also facilitate the development of new methods of treatment for this disease. At present, the only medications approved by the U.S. Food and Drug Administration for the treatment of AD are cholinesterase inhibitors. Unfortunately, these drugs provide only limited clinical benefit in controlling the symptoms of AD, and do little to actually intervene in the disease process. Thus, there is a strong need for the development of better treatments for AD.

In accordance with the present invention, it has been discovered that, while all three Mint proteins (Mints 1–3) bind to the cytoplasmic tail of APP, only Mint 1 and 2 can modulate the transcriptional activation mediated by a fusion protein consisting of the cytoplasmic tail of APP coupled to the transcription factor Gal4/VP16. These findings suggest that Mints 1 and 2, variants of these proteins that display enhanced abilities to modulate the transcriptional activation mediated by the cytoplasmic tail of APP relative to wild-type Mints 1 and 2, or small molecules which either mimic, inhibit or potentiate the effects of these proteins in modulating the transcriptional activation mediated by the cytoplasmic tail of APP, may be useful in regulating the rate of APP proteolysis and hence in the treatment of AD.

SUMMARY OF THE INVENTION

The present invention is directed to isolated nucleic acids encoding Mint protein variants having enhanced abilities to modulate the transcriptional activation mediated by the cytoplasmic tail of the amyloid precursor protein (APP) relative to wild-type Mint proteins. In preferred embodiments, the nucleic acids are those having the nucleotide sequences of SEQ ID NOS:1–8.

The present invention is further directed to purified Mint protein variants having enhanced abilities to modulate the transcriptional activation mediated by the cytoplasmic tail of APP relative to wild-type Mint proteins. In preferred embodiments, these proteins are those having the amino acid sequences of SEQ ID NOS:9–16.

The present invention further provides a method of modulating transcriptional activation. In one embodiment, this method comprises introducing into a target cell a nucleic acid encoding a wild-type Mint protein or a Mint protein variant having enhanced abilities to modulate transcriptional activation relative to wild-type Mint proteins. In preferred embodiments, the nucleic acids are those having the nucleotide sequences of SEQ ID NOS:1–8. In another embodiment, this method comprises introducing into a target cell a wild-type Mint protein or a Mint protein variant having enhanced abilities to modulate transcriptional activation relative to wild-type Mint proteins. In preferred embodiments, these proteins are those having the amino acid sequences of SEQ ID NOS:9–16. The Mint proteins and Mint protein variants of the present invention modulate transcriptional activation mediated by the cytoplasmic tail of APP.

The present invention also provides a method of identifying compounds that modulate transcriptional activation comprising contacting a cell containing an APP molecule modified in the C-terminal cytoplasmic tail to permit the specific transcriptional activation of a reporter gene and measuring the levels of reporter gene transcription in the presence and absence of the compound, wherein increased or decreased levels of reporter gene transcription in the presence of the compound indicate that the compound is capable of modulating transcriptional activation. Such compounds may be useful as candidate therapeutics for AD, or as models for the rational design of drugs useful for the treatment of AD.

The present invention further provides for transgenic knockout mice for Mint 1, Mint 2 and Mint 3. These animals may be useful for elucidating the pathophysiology of AD and for developing improved treatments for this disease.

In other embodiments, the present invention is directed to vectors, transfected cells and kits useful for modulating transcriptional activation or for the identification of compounds that can modulate APP-mediated transactivation.

BRIEF DESCRIPTION OF THE DRAWINGS

FIGS. 3A–3C show the binding of both PDZ domains of Mints to the cytoplasmic C-terminal sequence of presenilins. A. Percent of Mints solubilized from a rat forebrain membrane preparation that bound to an affinity column containing a peptide corresponding to the C-terminus of presenilin 1 or a control peptide derived from gp41 (n=3). B. Binding of Mint 1 to the immobilized C-terminal sequences of human presenilins 1 and 2, Drosophila presenilin, and control peptides derived from HPV2 and gp41 (n=3). C. Binding of various Mint 1 mutants prepared from transfected COS cells to the immobilized cytoplasmic C-terminal sequence of presenilin 1. Mint 1 mutants containing inactivating point mutations in either the first (Mint 1 PDZ1 *), the second (Mint 1 PDZ2*), or both PDZ domains (Mint 1 PDZ1/2*), or a truncation mutant of Mint 1 lacking the two PDZ domains (Mint 1)PDZ) were analyzed by affinity chromatography on immobilized presenilin 1 or gp41 control peptides.

FIGS. 13A–13HH show the sequences of the various Mint 1 and 2 nucleic acids and peptides. FIGS. 13A–13B. Mint 1 cDNA (SEQ ID NO:1). FIGS. 13C–13D. Mint 1 PDZ1* cDNA Sequence (SEQ ID NO:2). FIGS. 13E–13F. Mint 1)PDZ cDNA Sequence (SEQ ID NO:3). FIG. 13G. Mint 1) N-term cDNA Sequence (SEQ ID NO:4). FIGS. 13H–13I. Mint 2 cDNA Sequence (SEQ ID NO:5). FIGS. 13J–13K. Mint 2 PDZ1* cDNA Sequence (SEQ ID NO:6). FIG. 13L. Mint 2) PDZ cDNA Sequence (SEQ ID NO:7). FIG. 13M. Mint 2) N-term cDNA Sequence (SEQ ID NO:8). FIGS. 13N–13P. MINT 1 Peptide Sequence (SEQ ID NO:9). FIGS. 13Q–13S. MINT 1 PDZ1* Peptide Sequence (SEQ ID NO:10). FIGS. 13T–13V. MINT 1) PDZ Peptide Sequence (SEQ ID NO:11). FIGS. 13W–13X. MINT 1) N-term Peptide Sequence (SEQ ID NO:12). FIGS.

13Y–13AA. MINT 2 Peptide Sequence (SEQ ID NO:13). FIGS. 13BB–13DD. MINT 2 PDZ1* Peptide Sequence (SEQ ID NO:14). FIGS. 13EE–13FF. MINT 2) PDZ Peptide Sequence (SEQ ID NO:15). FIGS. 13GG–13HH. MINT 2) N-term Peptide Sequence (SEQ ID NO:16).

DETAILED DESCRIPTION OF THE INVENTION

Figure 1:
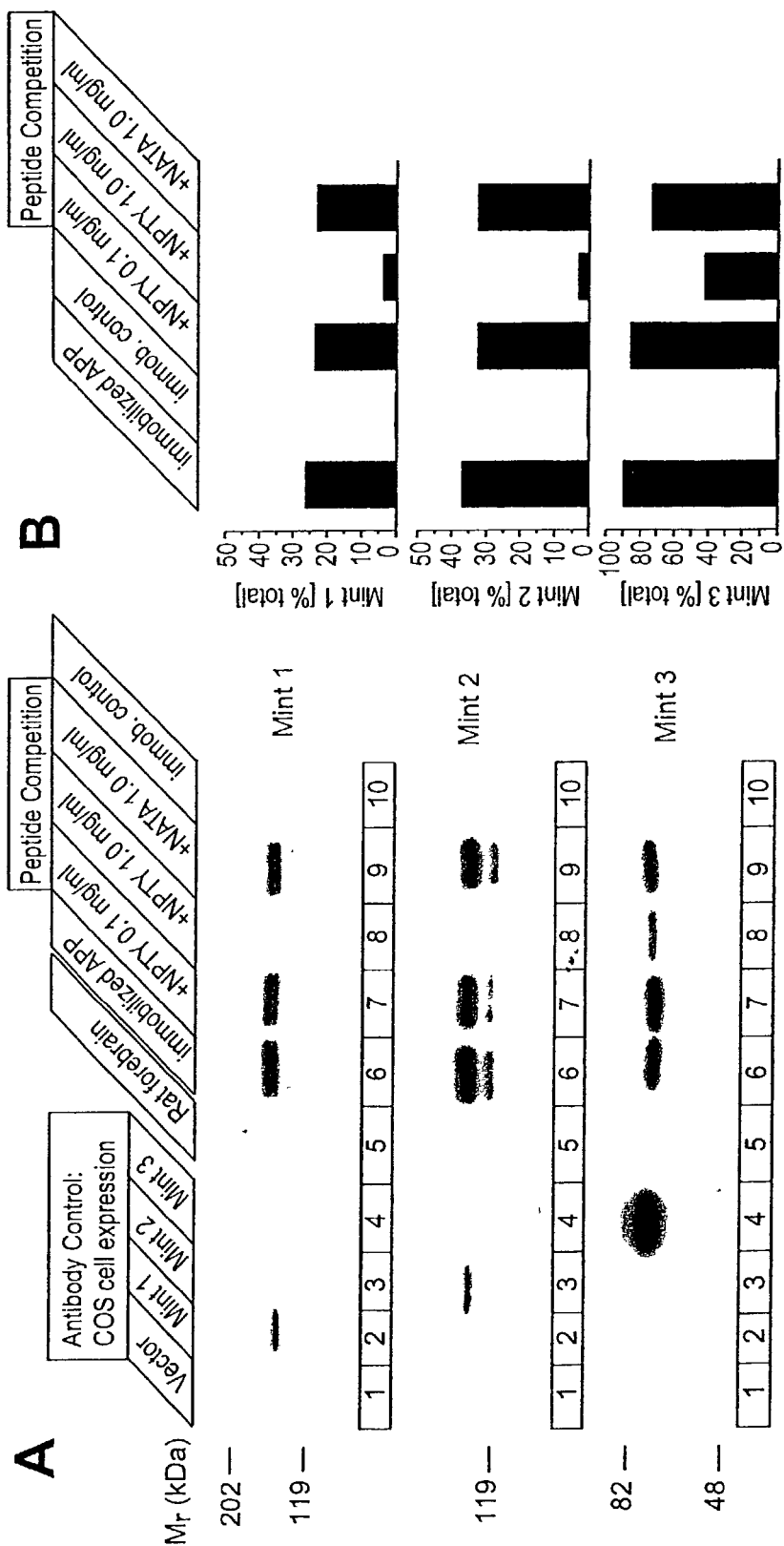
FIGS. 1A–1B show the similarly tight binding of Mints 1, 2, and 3 to the cytoplasmic tail of APP. A. Immunoblot analysis of Mint binding to the immobilized cytoplasmic tail of APP. B. Quantitation of the amount of Mints bound to the immobilized cytoplasmic tail of APP as percent of Mints in the starting brain extract.

Proteolytic processing of the amyloid precursor protein (APP) produces, inter alia, amyloid-β peptide, which may contribute to the pathogenesis of Alzheimer's disease (AD), and a C-terminal cytoplasmic tail, which may act as a transcriptional activator. In accordance with the present invention, it has been discovered that the proteins Mint 1, Mint 2 and Mint 3 can strongly bind to the PDZ domain of the C-terminal cytoplasmic tail of APP (see Example #1). Moreover, it has been discovered that the binding of Mint 1 and Mint 2 to the cytoplasmic tail of APP strongly inhibits the transcriptional activation produced by this protein (see Example #6). In particular, it has been discovered that the transcriptional activation of a reporter gene whose transcription is regulated by the binding of the GAL4/VP-16 transcription factor by an APP-Gal4/VP16 fusion protein can be strongly inhibited by Mint 1 and Mint 2 (see Example #6). This observation suggests that Mint proteins, especially Mint 1 and 2, variants of these proteins with enhanced abilities to modulate transcriptional activation relative to wild-type Mint proteins, or other molecules that may mimic the effects of the Mints or inhibit or potentiate the interaction between Mint proteins and the cytoplasmic tail of APP may be useful either as candidate therapeutics for the treatment of AD, as reagents for the identification of candidate therapeutics for the treatment of AD, or as models or targets for rational drug design.

The present invention relates to isolated nucleic acids encoding Mint proteins or Mint protein variants having enhanced abilities to modulate transcriptional activation relative to wild-type Mint proteins. In preferred embodiments, the nucleic acids are those having the nucleotide sequences of SEQ ID NOS:1–8. In other preferred embodiments, the nucleic acids are nucleic acids encoding the polypeptides having the amino acid sequences of SEQ ID NOS:9–16. In other embodiments, the nucleic acids are nucleic acids comprising the nucleic acids having the nucleotide sequences of SEQ ID NOS:1–8 or the nucleic acids encoding the polypeptides having the amino acid sequences of SEQ ID NOS:9–16. In still further embodiments, the nucleic acids are those substantially identical to the nucleic acids of SEQ ID NOS:1–8 or nucleic acids comprising nucleic acids substantially identical to the nucleic acids of SEQ ID NOS:1–8, wherein substantial identity at the nucleotide level occurs when at least about 60% to 75% or preferably at least about 80% or most preferably at least about 90% of the nucleotides comprising the nucleic acid molecule are identical over a defined length of the molecule, while the substantially identical nucleic acids retain the ability to encode for proteins having the biological function of the polypeptides having the amino acid sequences of SEQ ID NOS:9–16.

Substantially identical nucleic acid molecules may be identified by hybridization under suitably stringent hybridization conditions. Defining appropriate hybridization conditions is within the skill of the art. See e.g. Current Protocols in Molecular Biology, Volume I. Ausubel et al., eds. John Wiley:New York N.Y., pp. 2.10.1–2.10.16, first published in 1989 but with annual updating, wherein maximum hybridization specificity for DNA samples immobilized on nitrocellulose filters may be achieved through the use of repeated washings in a solution comprising 0.1–2× SSC (15–30 mM NaCl, 1.5–3 mM sodium citrate, pH 7.0) and 0.1% SDS (sodium dodecylsulfate) at temperatures of 65–68° C. or greater. For DNA samples immobilized on nylon filters, a stringent hybridization washing solution may be comprised of 40 mM NaPO$_4$, pH 7.2, 1–2% SDS and 1 mM EDTA. Again, a washing temperature of at least 65–68° C. is recommended, but the optimal temperature required for a truly stringent wash will depend on the length of the nucleic acid probe, its GC content, the concentration of monovalent cations and the percentage of formamide, if any, that was contained in the hybridization solution (Current Protocols in Molecular Biology, Volume I. Ausubel et al., eds. John Wiley:New York N.Y., pp. 2.10.1–2.10.16. 1989 with annual updating), all of which can be determined by the skilled artisan.

The present invention is further directed to purified Mint proteins or Mint protein variants having enhanced abilities to modulate transcriptional activation, and particularly the transcriptional activation mediated by the cytoplasmic tail of APP, relative to wild-type Mint proteins. In preferred embodiments, these proteins are those having the amino acid sequences of SEQ ID NOS:9–16. In further embodiments, the proteins are polypeptides encoded by the nucleic acids having the nucleotide sequences of SEQ ID NOS:1–8. In other embodiments, the proteins are polypeptides encoded by nucleic acids that are substantially identical to the nucleic acids of SEQ ID NOS:1–8, wherein substantial identity at the nucleotide level occurs when at least about 60% to 75% or preferably at least about 80% or most preferably at least about 90% of the nucleotides comprising the nucleic acid molecule are identical over a defined length of the molecule.

The present invention further provides a method of modulating the transcriptional activation mediated by the cytoplasmic tail of APP. In one embodiment, this method comprises introducing into a target cell a nucleic acid encoding a Mint protein or a Mint protein variant having enhanced abilities to modulate the transcriptional activation mediated by the cytoplasmic tail of APP relative to wild-type Mint proteins.

In preferred embodiments, the nucleic acids are those having the nucleotide sequences of SEQ ID NOS:1–8. In other preferred embodiments, the nucleic acids are nucleic acids encoding the polypeptides having the amino acid sequences of SEQ ID NOS:9–16. In other embodiments, the nucleic acids are nucleic acids comprising the nucleic acids having the nucleotide sequences of SEQ ID NOS:1–8 or the nucleic acids encoding the polypeptides having the amino acid sequences of SEQ ID NOS:9–16. In still further embodiments, the nucleic acids are those substantially identical to the nucleic acids of SEQ ID NOS:1–8 or nucleic acids comprising nucleic acids substantially identical to the nucleic acids of SEQ ID NOS:1–8, wherein substantial identity at the nucleotide level occurs when at least about 65% to 70% or preferably at least about 80% or most preferably at least about 90% of the nucleotides comprising the nucleic acid molecule are identical over a defined length of the molecule.

The nucleic acids described above may be introduced into target cells using a variety of vectors. These vectors include virus-based vectors and non-virus based DNA or RNA delivery systems. Examples of potential virus-based gene transfer vectors include, but are not limited to, those derived from the following nonlimiting virus types: Adenoviridae; Birnaviridae; Bunyaviridae; Caliciviridae, the Capillovirus group; the Carlavirus group; the Carmovirus group; the Caulimovirus group; the Closterovirus group; the Commelina Yellow Mottle Virus group; the Comovirus virus group; Coronaviridae; the PM2 Phage group; Corcicoviridae; the Cryptic Virus group; the Cryptovirus group; the Cucumovirus Virus group; the Family Φ6 Phage group; Cysioviridae; the Carnation Ringspot group; the Dianthovirus group; the Broad Bean Wilt virus group; the Fabavirus virus group; Filoviridae; Flaviviridae; the Furovirus group; the Germinivirus group; the Giardiavirus group; Hepadnaviridae; Herpesviridae; the Hordeivirus virus group; the Illarvirus group; Inoviridae; Iridoviridae; Leviviridae; Lipothrixviridae; the Luteovirus group; the Marafivirus group; the Maize Chlorotic Dwarf Virus group; Icroviridae; Myoviridae; the Necrovirus group; the Nepovirus group; Nodaviridae; Orthomyxoviridae; Papovaviridae; Paramyxoviridae; the Parsnip Yellow Fleck Virus group; Partitiviridae; Parvoviridae; the Pea Enation Mosaic Virus group; Phycodnaviridae; Picornaviridae; Plasmaviridae; Prodoviridae; Polydnaviridae; the Potexvirus group; Potyvirus; Poxviridae; Reoviridae; Retroviridae; Rhabdovindae; the Rhizidiovirus group; Siphoviridae; the Sobemovirus group; SSV1-Type Phages; Tectiviridae; Tenuivirus; Tetraviridae; the Tobamovirus group; the Tobravirus group; Togaviridae; the Tombusvirus group; the Torovirus group; Totiviridae; the Tymovirus group; and Plant virus satellites.

In preferred embodiments, the viral vectors are those derived from retroviruses, for example Moloney murine leukemia-virus based vectors such as LX, LNSX, LNCX or LXSN (Miller and Rosman, Biotechniques 1989;7:980–989); lentiviruses, for example human immunodeficiency virus ("HIV"), feline leukemia virus ("FIV") or equine infectious anemia virus ("EIAV")-based vectors (Case et al., 1999, Proc Natl Acad Sci USA 96:2988–2993; Curran et al., 2000, Molecular Ther 1:31–38; Olsen, 1998, Gene Ther 5:1481–1487); adenoviruses (Zhang, 1999, Cancer Gene Ther 6:113–138; Connelly, 1999, Curr Opin Mol Ther 1:565–572), for example Ad5/CMV-based E1-deleted vectors (Li et al., 1993, Human Gene Ther 4:403–409); adeno-associated viruses, for example pSub201-based AAV2-derived vectors (Walsh et al., 1992, Proc Natl Acad Sci USA 89:7257–7261); herpes simplex viruses, for example vectors based on HSV-1 (Geller and Freese, 1990, Proc Natl Acad Sci USA 87:1149–1153); baculoviruses, for example AcMNPV-based vectors (Boyce and Bucher, 1996, Proc Natl Acad Sci USA 93:2348–2352); SV40, for example SVluc (Strayer and Milano, 1996, Gene Ther 3:581–587); Epstein-Barr viruses, for example EBV-based replicon vectors (Hambor et al, 1988, Proc Natl Acad Sci USA 85:4010–4014); alphaviruses, for example Semliki Forest virus- or Sindbis virus-based vectors (Polo et al., 1999, Proc Natl Acad Sci USA 96:4598–4603); vaccinia viruses, for example modified vaccinia virus (MVA)-based vectors (Sutter and Moss, 1992, Proc Natl Acad Sci USA 89:10847–10851) or any other class of viruses that can efficiently transduce human tumor cells and that can accommodate the nucleic acid sequences required for physiologic efficacy.

Non-limiting examples of non-virus-based delivery systems that may be used according to the invention include, but are not limited to, so-called naked nucleic acids (Wolff et al., 1990, Science 247:1465–1468), nucleic acids encapsulated in liposomes (Nicolau et al., 1987, Meth Enzymology 149:157–176), nucleic acid/lipid complexes (Legendre and Szoka, 1992, Pharmaceutical Res 9:1235–1242), and nucleic acid/protein complexes (Wu and Wu, 1991, Biother 3:87–95). The vectors comprising these nucleic acids may include, but are not limited to, plasmids, cosmids, phagemids, bacmids, artificial chromosomes or replicons.

In another embodiment, the method of modulating transcriptional activation comprises introducing into a target cell a Mint protein or a Mint protein variant having enhanced abilities to modulate transcriptional activation relative to wild-type Mint proteins. In preferred embodiments, these proteins are those having the amino acid sequences of SEQ ID NOS:9–16. In other embodiments, the proteins are polypeptides encoded by the nucleic acids having the nucleotide sequences of SEQ ID NOS:1–8. In other embodiments, the proteins are polypeptides encoded by nucleic acids that are substantially identical to the nucleic acids of SEQ ID NOS:1–8, wherein substantial identity at the nucleotide level occurs when at least about 60% to 75% or preferably at least about 80% or most preferably at least about 90% of the nucleotides comprising the nucleic acid molecule are identical over a defined length of the molecule.

The amount of a Mint protein within a cell may be increased by introducing the protein directly into the target cell. For example, for introduction into a cell, the Mint protein could be incorporated into a microparticle for uptake by pinocytosis or phagocytosis. In other embodiments, the Mint protein could be incorporated into a liposome. Other protein-stabilizing formulations useful for the delivery of proteins to target cells are known in the art.

The present invention also provides a method of identifying compounds that modulate transcriptional activation comprising contacting a cell containing an APP molecule modified in the C-terminal cytoplasmic tail to permit the specific transcriptional activation of a reporter gene and measuring the levels of reporter gene transcription in the presence and absence of the compound, wherein increased or decreased levels of reporter gene transcription in the presence of the compound indicate that the compound is capable of modulating transcriptional activation.

The term APP as used herein includes naturally occurring mammalian APP and also APP that has been modified, for example in a way to facilitate measurement of the transcriptional activation produced by the cytoplasmic tail of APP. Naturally occurring human APP is a 695 amino acid protein, in which the C-terminal 47 residues are designated the cytoplasmic tail. The gene encoding APP, its splice variants, and resulting nucleotide and amino acid sequences are known in the art and disclosed for example by Kang et al., supra; Selkoe, supra; Bayer et al., 1999, supra; Haass et al., supra; and Price et al., supra, the disclosures of which are incorporated herein by reference.

Further, APP as defined herein may include other modifications such as insertions, deletions and substitutions provided that the functions of ability of the cytoplasmic tail or part thereof to be cleaved from the remainder of APP and translocated to the nucleus are retained.

The C-terminal cytoplasmic tail of APP may be modified to allow detection of nuclear localization. The modification may be in any region of the cytoplasmic tail. The modification may be at the C-terminal or N-terminal end of the tail, for example at the junction of the transmembrane and cytoplasmic domains. In one embodiment, the cytoplasmic tail of APP is modified to include the DNA binding domain and the activation domain of the same or different heterologous transcription factors. Heterologous as used herein means not derived from a gene encoding APP. In this embodiment, nuclear localization is measured by determining activation of transcription of a reporter gene that is under the transcriptional control of a binding site for the DNA binding domain. Transcription factors and their component DNA-binding and activation domains are well known in the art.

In a preferred embodiment, the cytoplasmic tail is modified to include a heterologous DNA-binding domain such as the DNA-binding domain of the yeast transcription factor Gal4, or the bacterial LexA DNA binding domain. The Gal4 and LexA DNA binding domains are known in the art and disclosed for example by Giniger et al, 1985, Cell 40:767–774 and Hurstel et al., 1986, EMBO J 5:793–798. The modification may further contain the transcriptional activation domain of Gal4, or another activator such as the viral VP16 activator, which is disclosed for example by Stringer et al., 1990, Nature 345:783–786. In a preferred embodiment, the cytoplasmic tail of APP is modified to include Gal4 and VP16. A transcription factor module of Gal4-VP16 is described by Sadowski et al., 1988, Nature 335:563–564. Accordingly, the modification of the cytoplasmic tail may consist of a module consisting of a DNA-binding domain and a transcriptional activation domain, which may be from the same or different sources.

The reporter gene is operably linked to a binding site for the DNA-binding protein. For example, the reporter gene may be provided in the form of a Gal4- or LexA-dependent reporter plasmid containing a reporter gene such as luciferase or chloramphenicol acetyl transferase under the control of a Gal4 or LexA regulatory element, respectively, such as an upstream activating sequence. Translocation of the cytoplasmic tail of APP to the nucleus results in translocation of the transcription factor as well, resulting in activation of transcription of the reporter gene. Accordingly, detection of the reporter gene product provides an assay for nuclear localization of the cytoplasmic tail of APP, and hence measures cleavage of APP. Transcriptional activation assays are described by Fields et al., 1989, Nature 340:245–246, the disclosure of which is incorporated herein by reference. Gal4 and LexA reporter plasmids are described by Lillie et al., 1989, Nature 338:38–44 and Hollenberg et al., 1995, Mol Cell Biol 15:3813–3822.

Candidate compounds that may be tested by the assays of the present invention include proteins, peptides, non-peptide small molecules, and any other source of therapeutic candidate compounds. The compounds may be naturally occurring or synthetic, and may be a single substance or a mixture. Screening may be performed in high throughput format using combinatorial libraries, expression libraries and the like. Compounds identified as inhibitors of the transcriptional activation mediated by the cytoplasmic tail of APP may be subsequently tested for biological activity and used as therapeutics or as models for rational drug design.

Modulation in this context is defined as little as a 5% increase or decrease in transcriptional activation of the cytoplasmic tail of APP in the presence of the compound relative to the level of transcriptional activation in the absence of the compound. In preferred embodiments, the level of increase or decrease greater than 10% or more preferably greater than 20%.

Cells useful for the assays of the present invention include eukaryotic cells in which the cytoplasmic tail of APP can be translocated to the nucleus. Suitable cells include, for example, insect and mammalian cells. Preferred cells include Schneider, PC12, COS, HeLa and HEK293 cells.

Cells containing APP may be cells stably or transiently transfected with a construct encoding APP as described above using methods known to those of ordinary skill in the art. Constructs containing chimeric genes comprising a promoter operably linked to nucleic acid encoding an APP modified to include a module comprising the DNA-binding domains and transcriptional activation domain of the same or different transcription factor, are constructed using well-known recombinant DNA methods. These constructs are co-transfected into cells with the corresponding reporter constructs described above.

The transfected cells are contacted with the compound to be tested for its ability to modulate the transactivation mediated by the cytoplasmic tail of APP. A detectable increase or decrease in transcriptional activation of the reporter gene is indicative of a compound that modulates APP-mediated transcriptional activation. In one embodiment, the cells may be contacted with the candidate compound before expression of the modified APP is induced from an inducible promoter.

In a preferred embodiment of the present invention, human APP is modified to include Gal4-VP16 within the cytoplasmic tail. In particular, Gal4-VP16 is inserted between residues 651 and 652 of APP. The modified APP is generated by means of a mammalian expression plasmid containing a chimeric gene encoding residues 1–651 of APP, Gal4, VP16, and residues 652–695 of APP (i.e. the cytoplasmic tail of APP) under the control of a promoter (see Example #4). The plasmid may further comprise regulatory sequences, linkers, and other elements to facilitate cloning, replication, transfection and expression.

A cell comprising the modified APP is provided by transfecting a cell, preferably a mammalian cell, and most preferably a human cell, with the expression plasmid. The cell is co-transfected with a Gal4 reporter plasmid in which luciferase mRNA is driven by multiple copies of the Gal4 upstream activating sequence (UAS). When the modified APP is cleaved by γ-secretase, the cleavage product containing Gal4-VP16 enters the nucleus and activates transcription from the Gal4 reporter plasmid. The transfected cells are contacted with a candidate compound, and luciferase expression is measured in the presence and absence of the compound. Expression of luciferase is measured by standard assays, for example by measuring luciferase activity using a commercially available kit. Luciferase expression is a measure of transactivation. The compound that increases or decreases luciferase expression is the compound that modulates transcriptional activation.

In another preferred embodiment of the present invention, a cell, preferably a mammalian cell, and most preferably a human cell, is co-transfected with plasmids expressing the APP/Gal4-VP16 fusion protein, a Gal4 reporter plasmid in which luciferase mRNA is driven by multiple copies of the Gal4 upstream activating sequence (UAS), and a plasmid expressing one of the Mint proteins encoded by the nucleic acids of SEQ ID NOS:1–8, the nucleic acids encoding the polypeptides having the amino acid sequences of SEQ ID NOS:9–16, nucleic acids comprising the nucleic acids having the nucleotide sequences of SEQ ID NOS:1–8 or the nucleic acids encoding the polypeptides having the amino acid sequences of SEQ ID NOS:9–16, or nucleic acids substantially identical to the nucleic acids of SEQ ID NOS:1–8 or nucleic acids comprising nucleic acids substantially identical to the nucleic acids of SEQ ID NOS:1–8. The Mint protein expressed from one of these nucleic acids will interact with the cytoplasmic tail of the APP/Gal4-VP16 fusion protein, preventing it from activating transcription of the luciferase gene present on the reporter plasmid (see Example #7). Compounds which potentiate the modulatory affects of Mint on transcriptional activation may be identified by comparing the level of expression of the luciferase or any other suitable reporter gene from the reporter plasmid in the presence and absence of the compound. The compound that increases or decreases luciferase expression is the compound that potentiates the modulatory affects of Mint on transcriptional activation. Other reporter genes suitable for use in this assay are known to those of ordinary skill in the art.

In another embodiment, the present invention provides vectors that contain nucleic acids encoding the Mints proteins. In preferred embodiments, the vector comprises one of the nucleic acids having the nucleotide sequences of SEQ ID NOS:1–8 operably linked to expression control sequences, e.g. a promoter. In other preferred embodiments, the vector comprises a nucleic acid encoding one of the polypeptides having the amino acid sequences of SEQ ID NOS:9–16 operably linked to a promoter. In other embodiments, the vector comprises nucleic acids that are substantially identical to the nucleic acids of SEQ ID NOS:1–8 operably linked to a promoter, wherein substantial identity at the nucleotide level occurs when at least about 60% to 75% or preferably at least about 80% or most preferably at least about 90% of the nucleotides comprising the nucleic acid molecule are identical over a defined length of the molecule, and wherein the nucleic acids still encode peptides having the biological function of the polypeptides having the amino acid sequences of SEQ ID NOS:9–16.

In another embodiment, the present invention provides vectors that contain nucleic acids encoding the modified APP protein. In preferred embodiments, the vector comprises a nucleic acid encoding APP operably linked to a promoter wherein a nucleic acid module encoding a heterologous DNA binding domain of a transcription factor and a transcriptional activator of the same or a different transcription factor is contained within the portion of the nucleic acid that encodes the C-terminal cytoplasmic tail of APP. A module "within" the tail includes embodiments in which the module is at the 5'-end or 3'-end of the region encoding the cytoplasmic tail. In a preferred embodiment the module is Gal4-VP16. The vectors may further comprise regulatory sequences, linkers, and other elements to facilitate cloning, replication, transfection and expression.

The present invention further provides cells containing the foregoing vectors. The cells are eukaryotic, preferably mammalian, and most preferably human. Cells containing the vectors of the invention may be obtained by methods known in the art, and may be transiently or stably transfected. The cells may also further contain a corresponding reporter plasmid as described hereinabove.

The present invention further provides kits useful for identifying a compound that modulates transcriptional activation. The kits may comprise vectors encoding modified APP, modified Mint proteins, and the reporter gene. Alternatively, the kits may contain cells transformed by one or more of these vectors or cells suitable for transfection by these vectors and a means for transfecting these cells. The kits may also comprise a means for measuring expression of the reporter gene contained in the reporter plasmid.

The present invention also provides for transgenic knockout mice for Mint 1, Mint 2 and Mint 3. These animals may be useful for elucidating the pathophysiology of AD and for developing improved treatments for this disease.

The following nonlimiting examples serve to further illustrate the present invention.

EXAMPLES

Materials and Methods

Plasmid construction. 1. Gal4-containing transactivation plasmids. Most of the plasmids used for the transactivation experiments described herein were reported previously (Cao and Südhof, 2001, Science 293:115–120). All eukaryotic expression vectors containing Gal4 or Gal4/VP16 were based on pMst (Gal4) and pMst-GV (Gal4/VP16) which are derived from the SV40 promoter-based mammalian expression vector pM (Clontech; Cao and Südhof, 2001, Science 293:115–120). In addition to the previously described vectors, the following vectors were constructed: pMst-GV-APP$_{ICF}$ (APP$_{ICF}$-Gal4/VP16), generated by cloning the intracellular fragment of human APP$_{695}$ (APP$_{ICF}$, residues 652–695) into the BamHI/SalI sites of pMst-GV; pMst-GV-APP (APP-Gal4/VP16), by cloning the extracellular and TMR fragments of human APP$_{695}$ (APPe, residues 1–651) into the NheI site of pMst-GV-APP$_{ICF}$; pMst-GV-APPγ (APPγ-Gal4/VP16), by cloning residues 639–651 of human APP$_{695}$ preceded by a methionine into the BglII/NheI sites of pMst-GV-APP$_{ICF}$. pMst-GV-APP$_{ICF}$* (APP$_{ICF}$*-Gal4/VP16), pMst-GV-APP* (APP*-Gal4/VP16), and pMst-GV-APPγ* (APPγ*-Gal4/VP16) were generated from their respective parent plasmid by site-specific mutagenesis replacing NPTY$_{(684-687)}$ with NATA$_{(684-687)}$ using the QUIKCHANGE® mutagenesis kit (Stratagene, La Jolla). pMst-GV-NRX (NRX-Gal4/VP16) was generated by cloning the intracellular fragment of rat Neurexin 1β (NRX$_{ICF}$, residues 414–468) into the BamH/SalI sites of pMst-GV, followed by cloning the extracellular and TMR fragments (NRXe, residues 1–417) into the NheI site. pMst-GV-NA (NRXe-Gal4/VP16-APP$_{ICF}$) was generated by cloning NRXe into the NheI site of pM5t-GV-APP$_{ICF}$, and pMst-GV-AN (APPe-Gal4/VP16-NRX$_{ICF}$) by cloning the intracellular fragment of Neurexin 1β (NRX$_{ICF}$) into the BamHI/SalI-sites of pMst-GV, followed by cloning of APPe into the NheI site. 2. Mint plasmids. The eukaryotic pCMV5 expression vectors for full-length rat Mints 1, 2 and 3 have been described previously (Okamoto and Südhof, 1997, J Biol Chem 272:31459–31464; Okamoto and Südhof, 1998, Eur J Cell Biol 77:161–165). Mutations were inserted in these parent vectors by site-specific mutagenesis as described above. pCMV-Mint 1-PDZ1* was constructed by mutating GV$_{(670,671)}$ to AA$_{(670,671)}$ in the first PDZ domain's carboxylate binding loop, and pCMV-Mint 1-PDZ2* was created by mutating GF$_{(762,763)}$ to AA$_{(762,763)}$ in the carboxylate binding loop of the second PDZ domain. pCMV-Mint 1-ΔPDZ was generated by introducing a stop codon after residue 659 in pCMV-Mint 1. A hydrophobic pocket of the PTB domain of Mint 1 was altered at positions YQEF$_{(613-616)}$ (SEQ ID NO:26) to SQES$_{(613-616)}$ (SEQ ID NO:27) to generate the pCMV-Mint 1-PTB* construct. pCMVmyc-Mint 1 was generated by cloning the full-length Mint 1 coding sequence from pEGFP-Mint 1 (a gift from Dr. Anton Maximov, UT Southwestern, Dallas) into the EcoRI/KpnI sites of pCMV-myc. To construct pCMVmyc-Mint 1-ΔNterm, the C-terminal part of Mint 1 encoding residues 451–839 was cloned into the KpnI/XbaI sites of pCMVmyc. pCMV-Mint 2-ΔPDZ was generated by introducing a stop codon after residue 570 in pCMV-Mint 2, and pCMV-Mint 3-ΔPDZ by introducing a stop codon after residue 391 in pCMV-Mint 3.

3. Other plasmids. The eukaryotic expression vectors for CASK (Hata et al., 1996, J Neurosci 16: 2488–2494) and Fe65 (Cao and Südhof, 2001, Science 293:115–120) were described previously.

Antibodies. Some antibodies were described previously (Biederer and Südhof, 2000, J Biol Chem 275:39803–39806; Biederer and Südhof, 2001, J Biol Chem 276: 47869–47876; Cao and Südhof, 2001, Science 293: 115–120). The APP antibody used was a polyclonal rabbit serum (U955) raised against the cytosolic, extreme C-terminal 15 residues of APP coupled to keyhole-limpet hemocyanin. Monoclonal antibodies to Mints 1, 2 and 3, TGN 38, and EEA1 were obtained from Transduction Laboratories (Lexington Ky.); monoclonal antibodies to calnexin were obtained from Chemicon (Temecula Calif.); and monoclonal antibodies to Golgi 58K protein were obtained from Sigma (St. Louis Mo.). Polyclonal Mint 1 antibodies were described previously (P932; Okamoto and Südhof, 1997, J Biol Chem 272:31459–31464), as were antibodies against Velis (T813; Butz et al., 1998, Cell 94:773–782). Polyclonal anti-myc antibodies were obtained from Santa Cruz Biotechnology (Santa Cruz Calif.), and polyclonal antibodies directed against Mint 3 were obtained from Affinity Bioreagents (Denver Colo.). For all Mint antibodies, specificity was confirmed using preparations from COS cells transfected with expression vectors for Mints 1–3 (data not shown).

Biochemical preparations. All steps were carried out on ice or at 4° C. Rat forebrains (Pel Freez, Rogers Ak.) were homogenized in a pestle tissue grinder using a slow speed stiffer at a tissue:buffer ratio of 10% (w/v) in buffer RMP (20 mM Hepes-KOH (pH 7.4), 125 mM K-acetate, 5 mM $MgCl_2$, 320 mM sucrose) adjusted to 1.0% TRITON® X-100 (octyl phenol ethoxylate) in the presence of protease inhibitors. For preparation of membrane proteins, rat forebrains were homogenized in buffer RMP, the samples were centrifuged in an Eppendorf (Hamburg, Germany) microcentrifuge at 600 g for 10 min to obtain the postnuclear supernatant, and membranes were pelleted in a Sorvall (Kendro Laboratory Products, Newtown Conn.) S80-AT3 rotor at 280,000 g for 20 min. The membrane pellet was extracted in buffer RMIP adjusted to 1.0% TRITON® X-100 (octyl phenol ethoxylate) using a pestle tissue grinder, and centrifuged again at 280,000 g for 20 min to yield the solubilized membrane proteins.

Peptide bead affinity chromatography. Peptides were synthesized on an ABI (Applied Biosystems, Foster City Calif.) synthesizer with an added N-terminal cysteine for coupling to SULFOLINK® Beads (a 6% cross-linked beaded agarose matrix that has been derivatized with a 12-atom spacer arm that ends in an iodoacetyl group; Pierce, Rockford Ill.) according to the manufacturer's instructions at 1.0 mg peptide/ml beads. For binding to the APP NPTY (SEQ ID NO:17) motif, a peptide corresponding to the APP-derived sequence CGYENPTYKFFEQMQN (human APP, residues 398–412; SEQ ID NO:25), was immobilized on SULFOLINK® (a 6% cross-linked beaded agarose matrix that has been derivatized with a 12-atom spacer arm that ends in an iodoacetyl group; Pierce, Rockford Ill.) beads. For binding to Presenilin C-terminal sequences, peptides corresponding to the extreme C-termini of human Presenilin 1 (sequence CMDQLAFHQFYI; SEQ ID NO:18), human Presenilin 2 (sequence CMDTLASHQLYI; SEQ ID NO:19), or *Drosophila Presenilin* (sequence CMEDLSAKQVFI; SEQ ID NO:20) were immobilized. As negative controls, peptides corresponding to the extreme C-terminus of human HPV2 (poliovirus receptor-related protein 2; sequence CGSLISRRAVYV; SEQ ID NO:21) and a peptide derived from the gp41 glycoprotein (sequence CWFSITNWLWYI; SEQ ID NO:22) were utilized. Extracts of transfected eukaryotic cells or proteins solubilized from rat brain were incubated with 20 μg peptide immobilized on SULFOLINK® (a 6% cross-linked beaded agarose matrix that has been derivatized with a 12-atom spacer arm that ends in an iodoacetyl group; Pierce. Rockford Ill.) beads for 12–16 h at 4° C. under mild agitation. Binding was performed in buffer RMP adjusted to 1.0% TRITON® X-100 (octyl phenol ethoxylate) and 600 mM potassium acetate. For APP competition experiments, the soluble peptides QNGYENPTYKFFEQ (SEQ ID NO:23) or QNGYENATAKFFEQ (SEQ ID NO:24), corresponding to the native or mutated APP NPTY (SEQ ID NO:17) motif, were added during the binding incubation at the concentrations of 0.1 mg/ml and 1.0 mg/ml. Bound proteins were eluted with 2% SDS.

Immunoprecipitations. HEK293 were co-transfected for APP and the individual Mints 1, 2 or 3, respectively, and after 2 days collected in IP buffer (25 mM Hepes-KOH (pH 7.4), 125 mM K-acetate, 5 mM $MgCl_2$, 1.0% IGEPAL CA-630, Sigma), 10% glycerol) in the presence of protease inhibitors. After passing the cell suspension through a 28 gauge syringe, the lysate was centrifuged in an Eppendorf microcentrifuge at 21,000 g for 20 min and the detergent-extracted material was subjected for 2 h to immunoprecipitation using antibodies directed against APP (U955) or the respective pre-immune serum.

Miscellaneous biochemical procedures. SDS-PAGE and immunoblotting was performed as described (Laemmli, 1970, Nature 277:680–685; Towbin et al., 1979, Proc Natl Acad Sci USA 76:4350–4354). For standard immunodetection on Western blots, enhanced chemiluminiscence (ECL; Amersham) was applied. Quantitative immunoblotting was performed using radiolabeled $^{125}I$ secondary antibodies (Amersham Biosciences, Piscataway N.J.), and the signals were quantitated on a Phosphorimager (Molecular Dynamics, Sunnyvale Calif.) using ImageQuant software. To determine levels of expressed Mint 1 protein, signals of cell lysates were compared to those from known amounts of purified GST-Mint 1. Protein concentrations were determined using the BCA protein assay (Pierce, Rockford Ill.).

Immunocytochemistry. 1. Immunoperoxidase staining: Adult mice were perfusion-fixed in 4% paraformaldehyde in phosphate-buffered saline (PBS) pH 7.4. 35 μm vibratome sections from brain were blocked in 10% normal goat serum containing 0.1% TRITON® X-100 (octyl phenol ethoxylate) for one hour, incubated with the various primary antibodies overnight at 4° C. and with the biotinylated secondary antibody for 1 hr. Sections were processed using a VECTASTAIN® ABC Elite Kit, which contains avidin DH and biotinviated enzyme (Vector, Burlingame, Calif.) according to the manufacturer's instruction. The final immunosignal was developed using 3'3-diaminobenzidine tetrahydrochloride (DAB). For immunofluorescence labeling, primary hippocampal cells on cover slips were fixed in situ for 10 min with absolute methanol at −20° C., permeabilized in 0.1% saponin/PBS, and blocked in 3% milk/PBS. The primary incubation was carried out in blocking buffer for one hour at room temperature. After washing with PBS, the cells were incubated with goat anti-rabbit or goat anti-mouse secondary antibodies that were coupled with ALEXA FLUOR® 488 and ALEXA FLUOR® 546 (fluorescent dyes; Molecular Probes, Eugene Oreg.). Labeled cells were viewed with a Leica (Leica Microsystems, Bannockburn Ill.) TCS SP2 confocal microscope or a Zeiss (Carl Zeiss Optical Inc., Chester Va.) fluorescent microscope with a Hamamatsu (Bridgewater N.J.) ORCA-100 digital camera. Final images were processed by METAMORPH® (an integrated software and hardware system for the capture and analysis of microsconic or macrosconic images from scientific grade digital and video CCD cameras; Universal Imaging, Downingtown Pa.) and ADOBE® PHOTOSHOP® imaging analysis software.

Transfections were performed at 50–80% confluency in 6-well plates using FUGENE6 transfection reagent (Roche, Basel, Switzerland).

Transactivation assays. PC12, COS, HeLa, and HEK293 cells were co-transfected with three or four plasmids: a. pG5E1B-luc (HEK293 cells, HeLa cells, and COS cells=0.2–0.5 μg DNA; PC12 cells=1.0 μg); b. pCMV-LacZ (HEK293 cells, HeLa cells, and COS cells=0.05 μg DNA; PC12 cells=0.5 μg DNA); c. pMst (Gal4), pMst-GV-APP (APP-GV), pMst-GV (GV), pMst-GV-APPct (APPct-GV), pMst-APPct (APPct-Gal4), pMst-GV-APP* (AAP*-Gv), pMst-GV-APPct* (APPct*-GV), pMst-APPct* (APPct*-Gal4), pMst-GV-APP( (APP(-GV), pMst-GV-NRX (NRX-GV), pMst-GV-NA (NRXe-GV-APPc), pMst-GV-AN (APPe-GV-NRXc)(HEK293, HeLa, and COS cells=0.1–0.3 μg DNA; PC12 cells=1.0 μg DNA). Where indicated, a fourth plasmid was co-transfected: pcDNA3.1-PS2D366A (kind gift of Dr. C. Haass, Munich); pCMV-Mint1; pCMV-Mint 1-PDZ1*; pCMV-Mint 1-PDZ2*; pCMV-Mint 1-PTB*; pCMVmyc-Mint 1; pCMVmyc-Mint 1-ΔNterm; pCMV-Mint 1-ΔPDZ; pCMV-Mint 2; pCMV-Mint 2-ΔPDZ; pCMV-Mint 3; pCMV-Mint 3-ΔPDZ; pCMV5-Fe65; pCMV-CASK (HEK293, HeLa, and COS cells=0.1–0.3 μg DNA or as specified in the discussion of each individual experiment; PC12 cells=0.5 μg DNA). For negative controls, the expression vector pCMV5 was used without insert. Cells were harvested 48 hr post-transfection in 0.2 ml/well reporter lysis buffer (Promega, Madison Wiss.), and their luciferase and β-galactosidase activities were determined with the Promega luciferase assay kit using a chemiluminescence reader (LUCY2, Anthos Labtec, Austria) and the standard O-nitrophenyl-D-galacto-pyranoside (Sigma, St. Louis Mo.) method, respectively. The luciferase activity was standardized by the β-galactosidase activity to control for transfection efficiency and general effects on transcription, and further normalized for the transactivation observed in cells expressing Gal4 alone where indicated. Values shown are averages of transactivation assays carried out in duplicate, and repeated at least three times for each cell type and constructs. All constructs were assayed in three or four cell lines, but usually only representative results for one cell line are shown.

Example 1

Comparison of the binding of Mints/X11 1, 2, and 3 to APP. Previous results have separately examined the ability of Mints to bind to APP or to presenilins, and to stabilize APP in co-transfected cultured cells (Borg et Al., 1996, Mol Cell Biol 16:6229–6241; McLoughlin and Miller, 1996, FEBS Lett 397:197–200; Zhang et al., 1997, EMBO J. 16: 6141–6150; Borg et al., 1998a, J Biol Chem 273:14761–14766; Sastre et al., 1998, J Biol Chem 273: 22351–22357; Lau et al., 2000, Mol Cell Neurosci 16:557–565; Okamoto et al., 2001, Eur J Neurosci 12:3067–3072). These experiments established a potentially important connection between Mints, presenilins, and APP, but the relative activities of the three Mints and the generality of these putative targets were not analyzed.

As an initial step towards understanding the common versus unique properties of Mint isoforms, a comparison of the binding of different Mints to APP and presenilin, and their effect on APP in transfected cells, was performed. Since these and subsequent experiments critically depended on the specificity of the Mint antibodies used, a study validating the specificity of these antibodies was first performed using transfected COS cells that express individual Mints. As shown in FIG. 1, antibodies used for the respective Mint isoforms bound specifically to protein extracts prepared from COS cells transfected with a control vector (lane 1) or Mint 1–3 expression vectors (lanes 2–4). Immunoblotting was performed using monoclonal antibodies against Mints 1 and 2, and polyclonal antibodies against Mint 3. Fractions were also analyzed by immunoblotting for the negative control proteins Rab GDP-dissociation inhibitor protein (GDI), a soluble protein, and for synaptophysin 1 (Syp), a membrane protein of synaptic vesicles. This study confirmed the mono-specificity of the antibodies, which could thus be applied to detect each Mint isoform separately in complex solutions containing multiple Mints, such as brain homogenates.

Affinity chromatography of rat brain proteins on the immobilized cytoplasmic tail of APP was then used to examine the binding of endogenous Mints to APP. Proteins from rat forebrain homogenates (lane 5) were bound to an immobilized cytoplasmic peptide derived from APP in the absence of added soluble peptide (lane 6), or in the presence of 0.1 or 1.0 mg/ml of a soluble peptide containing the wild-type sequence of the APP cytoplasmic tail (lanes 7 and 8), or of a APP tail peptide point-mutated in the NPTY binding sequence for Mints (lane 9). As a further control, binding of Mints to a control column with an immobilized peptide derived from gp41 was examined (lane 10). Binding was performed at 600 mM salt. The samples tested in lanes 6–10 are proteins bound to beads after the respective binding and peptide competition experiments. Recovery of the three Mints from the brain homogenates was quantitated with $^{125}$I-labeled secondary antibodies, as shown in FIG. 1A, lanes 5–10. All three Mints tightly bound to APP (FIG. 1A, lane 6), and binding was inhibited by high concentrations of the corresponding wild-type but not mutant APP tail peptide (FIG. 1A, lanes 7–9). As shown in FIG. 1B, quantitation revealed that Mints from the brain homogenate were recovered efficiently on the affinity column with yields of 25% to 90%; for example, the immobilized APP tail extracted almost all of the brain Mint 3, and even 1 mg/ml of competing peptide was unable to completely block it from binding to the column. In contrast, only 25% of brain Mint 1 were bound. No Mint binding to a control peptide was observed (FIG. 1A, lane 10).

To test if Mints interact with APP in vivo, the levels of the transfected APP were measured by quantitative immunoblotting using $^{125}$I-labeled secondary antibodies (FIGS. 2A and 2B). As a control, the gene for Fe65, a protein that also binds to the cytoplasmic tail of APP (Fiore et al., 1995, J Biol Chem 270:30853–30856), was transfected. Under control conditions (lane 1), little $APP_{695}$ is expressed in the cells because the predominant splice variants in peripheral tissues include the Kunitz domain (Kitaguchi et al., 1988, Nature 331:530–532; Tanzi et al., 1988, Nature 331:528–30). The migration position of the endogenous APP containing the Kunitz domain and the transfected $APP_{695}$ lacking this domain are indicated on the right of the panel. The quantities of loaded lysates were normalized to equal amounts of transfected cells based on the activity of co-transfected β-galactosidase.

Figure 2:
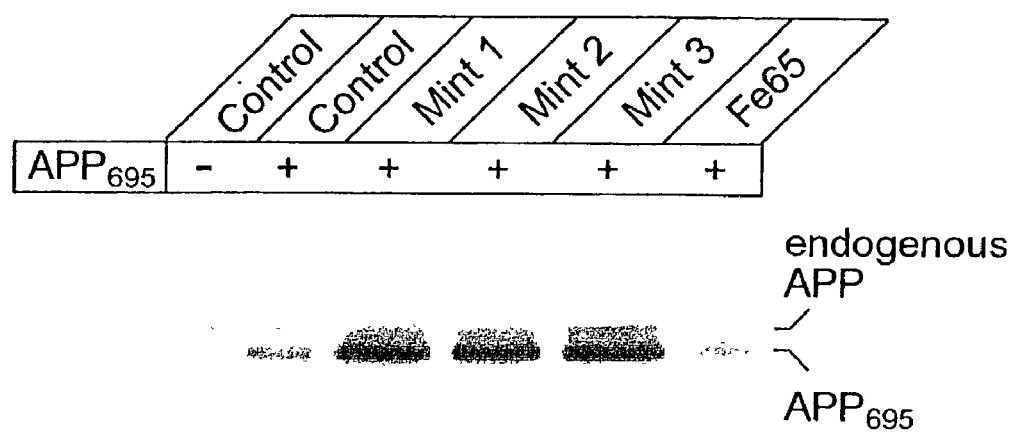
FIGS. 2A–2B show that co-transfection of Mints 1, 2, or 3 increases the steady-state levels of APP. A. Immunoblot analysis of HEK293 cells co-transfected with expression plasmids encoding $APP_{695}$, Mints 1–3, and Fe65 as indicated. B. Quantitation of the levels of $APP_{695}$ in transfected HEK293 cells shown in A.
Figure 2:
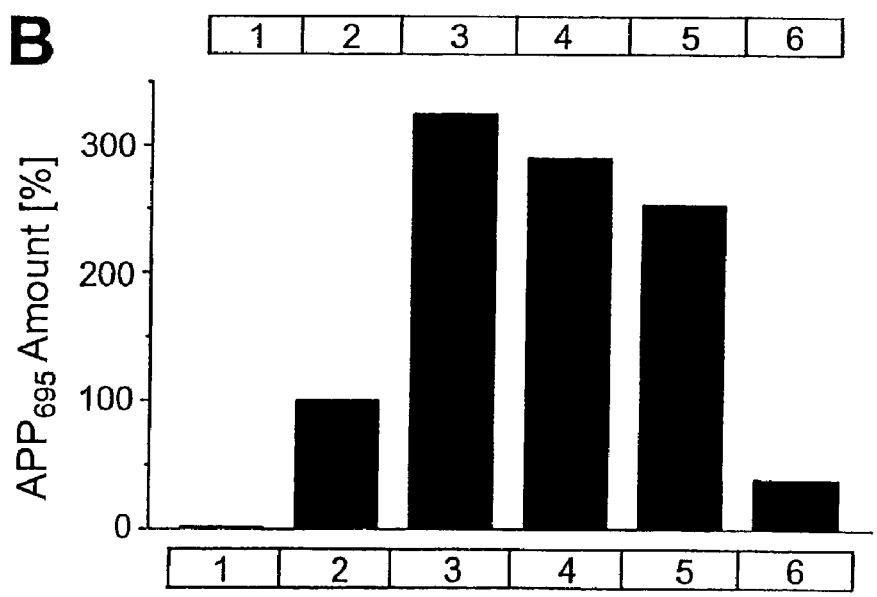

All three Mints dramatically increased APP levels (up to three-fold; FIG. 2, lanes 3–5), extending previous observations that Mint 1 stabilizes transfected APP and increases its steady-state levels (Borg et al., 1998a, J Biol Chem 273: 14761–14766; Sastre et al., 1998, J Biol Chem 273:22351–22357). As a control, Fe65 (which also binds to APP) slightly decreased the steady-state levels of transfected APP, although this was not necessarily a specific effect since co-transfection of any protein usually decreases expression because it dilutes the transcription/translation machinery. The stabilization of APP in the transfected cells could be due to a direct or indirect interaction of Mints with APP. The levels of endogenous APP do not change significantly because most of the cells are not transfected, and thus are not exposed to the transfected Mints.

Although the affinity chromatography experiments already suggested a direct interaction (FIG. 1), this question was further examined by the co-immunoprecipitation of Mints with APP from the transfected cells (FIG. 2C). In these studies, $APP_{695}$ and Mints 1, 2, or 3 were co-expressed in transfected HEK293 cells ("Start"; lane 1). Cellular proteins were then immunoprecipitated with an antibody to the C-terminus of APP ("IP APP"; lane 2), or a control antibody ("IP Control"; lane 3). Samples were analyzed by immunoblotting with monoclonal antibodies to the indicated proteins. The double band for Mint 2 is probably due to a hypersensitive proteolytic site in the N-terminus of Mint 2. For detection of APP, the quantity loaded in lanes 2 and 3 was 5-fold less than for detection of Mints. Indeed, Mints 1, 2 and 3 were co-immunoprecipitated with antibodies to APP, but not with control antibodies (FIG. 2C), supporting the notion that Mints directly bind to APP.

Example 2

Figure 3:
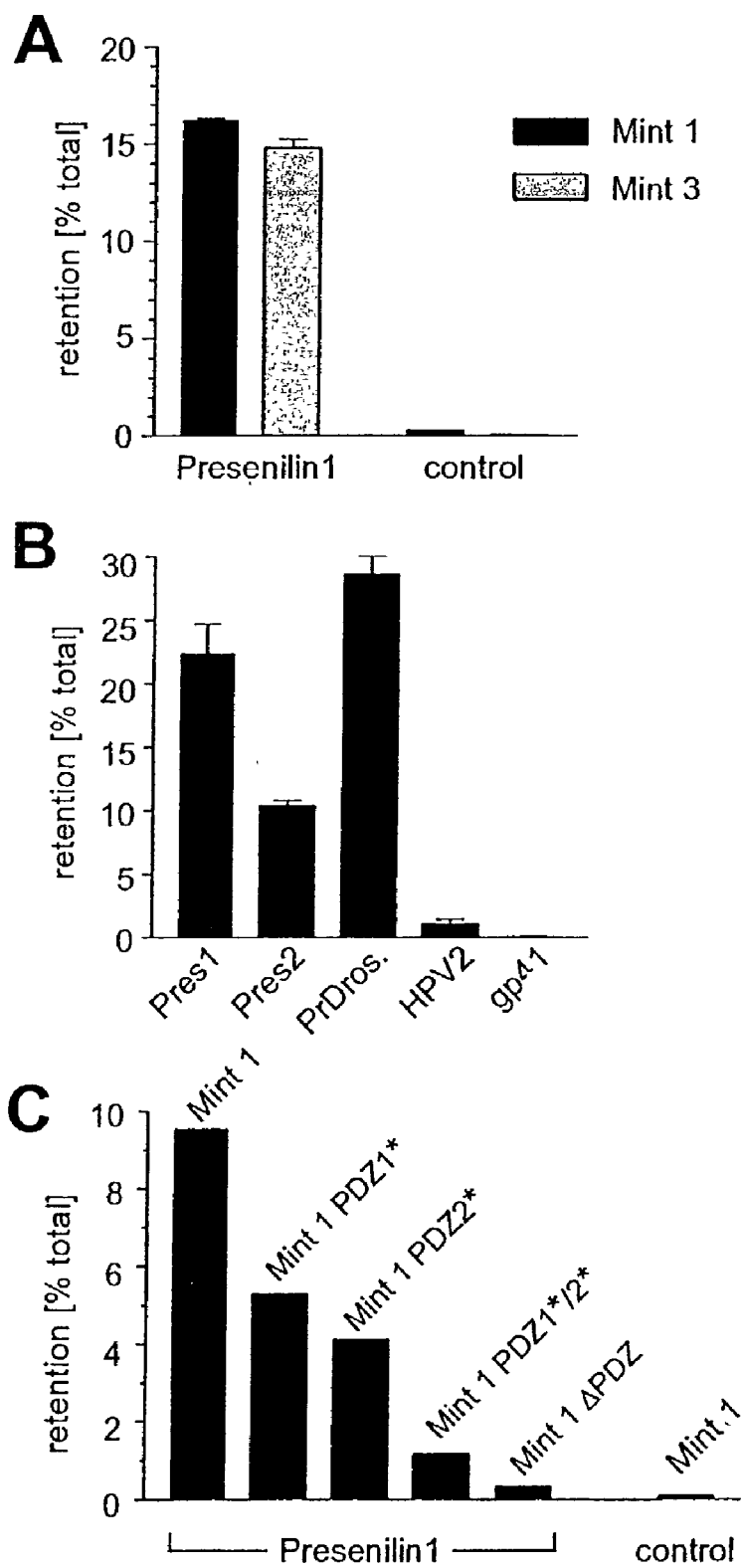
FIG. 3A–C shows the binding of both PDZ domains of Mints to the cytoplasmic C-terminal sequence of presenilins. A. Binding of Mints 1 and 3 to presenilin 1. B. Percent of Mints solubilized from a rat forebrain membrane preparation that bound to an affinity column containing a peptide corresponding to the C-terminus of presenilin 1 or a control peptide derived from gp41 (n=3). C. Binding of Mint 1 to the immobilized C-terminal sequences of human presenilins 1 and 2, Drosophila presenilin, and control peptides derived from HPV2 and gp41 (n=3). D. Binding of various Mint 1 mutants prepared from transfected COS cells to the immobilized cytoplasmic C-terminal sequence of presenilin 1. Mint 1 mutants containing inactivating point mutations in either the first (Mint 1 PDZ1*), the second (Mint 1 PDZ2*), or both PDZ domains (Mint 1 PDZ1/2*), or a truncation mutant of Mint 1 lacking the two PDZ domains (Mint 1 ΔPDZ) were analyzed by affinity chromatography on immobilized presenilin 1 or gp41 control peptides.

Binding of Mints to presenilins. The potential interaction of Mints with presenilins was examined using the same affinity chromatography approach employed for APP binding. Briefly, proteins solubilized from a rat forebrain membrane preparation ("Start"; lane 1 of FIG. 3A) were bound to an affinity column containing a peptide corresponding to the C-terminus of presenilin 1 ("Pres1"; lane 2 of FIG. 3A) or a control peptide derived from gp41 ("Control"; lane 3 of FIG. 3A). Bound proteins were analyzed by immunoblotting with antibodies to the indicated proteins, which included the negative control proteins GDI and synaptophysin (Syp). Note that the antibody to Velis used (Butz et al., 1998, Cell 94:773–782) recognizes all three Veli isoforms which migrate as two distinct bands. Immunoblotting showed that all three Mints bound to the cytoplasmic C-terminal sequence of presenilin 1 (FIG. 3A and data not shown), in agreement with previous observations (Lau et al., 2000, Mol Cell Neurosci 16:557–565). Binding was specific because Mints were not bound to control beads, and control proteins such as GDI and synaptophysin were not retained on the presenilin 1 column (data not shown). However, quantitations revealed that presenilin binding differed among Mints in (FIG. 3B, and data not shown). 14–16% of endogenous Mints 1 and 3 from brain were recovered on the presenilin column, but only 3% of Mint 2 was bound.

Mints bind to the cytoplasmic tail of APP via an interaction of the Mint PTB domain with the NPTY sequence in APP (Borg et al., 1996, Mol Cell Biol 16:6229–6241; McLoughlin and Miller, 1996, FEBS Lett 397:197–200; Zhang et al., 1997, EMBO J. 16: 6141–6150). Presenilin 1 does not include an NPxY sequence but feature a C-terminal sequence that resembles that of neurexins which bind to the PDZ domains of Mints (Biederer and Südhof, 2000, J Biol Chem. 275:39803–39806), suggesting that the binding of Mints to presenilin 1 may be mediated by one or both Mint PDZ domains.

To test if other PDZ domain proteins also bind to the C-terminal sequence of presenilin 1, the presenilin binding of PSD95, an abundant component of the postsynaptic density that contains three PDZ domains (Cho et al., 1992, Neuron 9: 929–942; Kistner et al., 1993, J Biol Chem 268: 4580–4583), and of Velis, a family of three proteins that contain a single PDZ domain (Butz et al., 1998, Cell 94:773–782), was examined. Both PDZ domain proteins were bound; whereas binding of PSD95 was weak, Velis were captured to the same extent as Mints 1 and 3 (FIGS. 3A and 3B).

The fact that multiple unrelated PDZ domain proteins bind to the C-terminal sequence of presenilin 1, but various Mints exhibit large differences in binding, raised concerns about the specificity of the interaction of Mints with presenilins, prompting a further examination of Mints binding specificity to presenilin.

The C-terminal presenilin 1 sequence is conserved in vertebrate presenilin 2 and in Drosophila presenilin. C-terminal peptides from all of these presenilins captured Mint 1, whereas control peptides did not, suggesting that all of these presenilins potentially interact with PDZ-domain proteins (FIG. 3C).

To identify which of the two PDZ domains in Mints binds to presenilins, we mutated the PDZ1 and PDZ2 domains of Mint 1 separately or together, or deleted them both. Presenilin binding assays with wild-type and mutant Mint proteins produced in transfected COS cells revealed that mutations in each of the two Mint 1 PDZ domains resulted in an approximately two-fold decrease in binding (FIG. 3D). Mutations in both PDZ domains or deletion of both PDZ domains almost completely abolished binding. Together these data suggest that each of the two Mint PDZ domains individually binds to presenilins in vitro.

Example 3

Localization of endogenous Mints in neurons. In vertebrates, Mints 1 and 2 are only detectable in brain, whereas Mint 3 is ubiquitously expressed (Okamoto and Südhof, 1997, J Biol Chem 272:31459–31464; Okamoto and Südhof, 1998, Eur J Cell Biol 77:161–165). To study the localization of Mints, rat brain sections were stained with antibodies to Mints 1 and 2. Mint 3 could not be investigated because the available antibodies were not suitable for immunocytochemistry.

Figure 4:
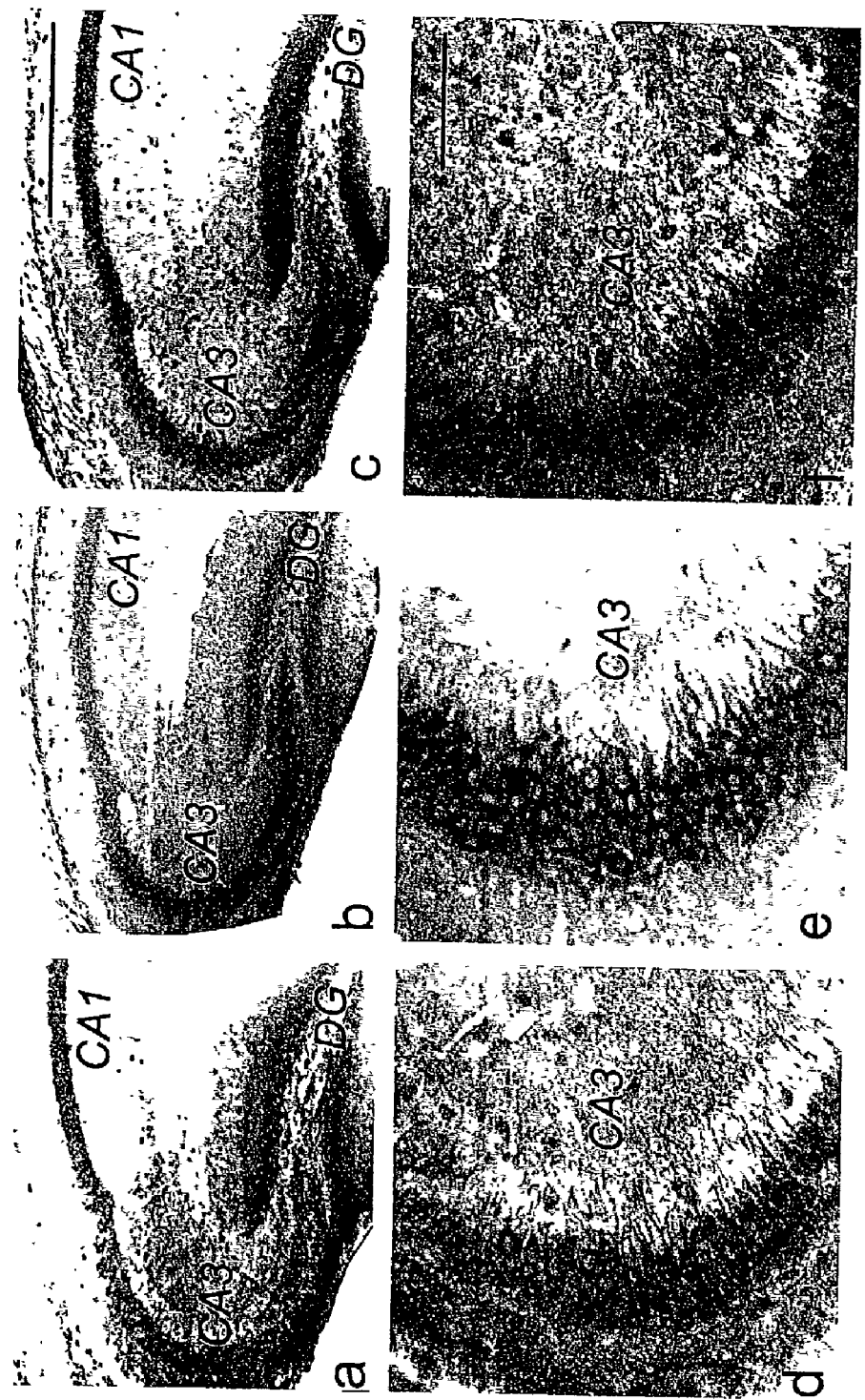
FIGS. 4A–4F show the immunoreactivity of Mint 1, Mint 2 and APP in mouse hippocampus. Vibratome sections (35 μm) from adult mouse hippocampus were stained for Mint 1 (A and D), Mint 2 (B and E), and APP (C and F) using the avidin-biotin peroxidase method.

Abundant labeling of the neuronal cell bodies, with less staining of the dendrites, was observed (FIGS. 4, A, B, D, and E; see also McLoughlin et al., 1999, Neurosci 11:1988–1994). APP exhibited a very similar distribution (FIGS. 4, C and F). Notably, nuclei were not labeled. Staining throughout the neuropil was detected that was weaker than the cell body staining, indicating that low levels of Mints may be present at synapses as suggested by Okamoto and colleagues. See Okamoto et al., 2000, Eur J Neurosci 12:3067–3072. FIGS. 4, D, E and F are enlarged images of CA3 regions from FIGS. 4, A, B and C. Antibodies against Mint 1 were polyclonal, and monoclonal against Mint 2. The polyclonal APP antibody used is directed against a C-terminal epitope in the cytoplasmic APP tail which is liberated upon γ-cleavage. Scale bars in FIG. 4C (for FIGS. 4, A–C)=0.5 mm; in FIG. 4F (for FIGS. 4, D–F)=0.1 mm.

Figure 5:
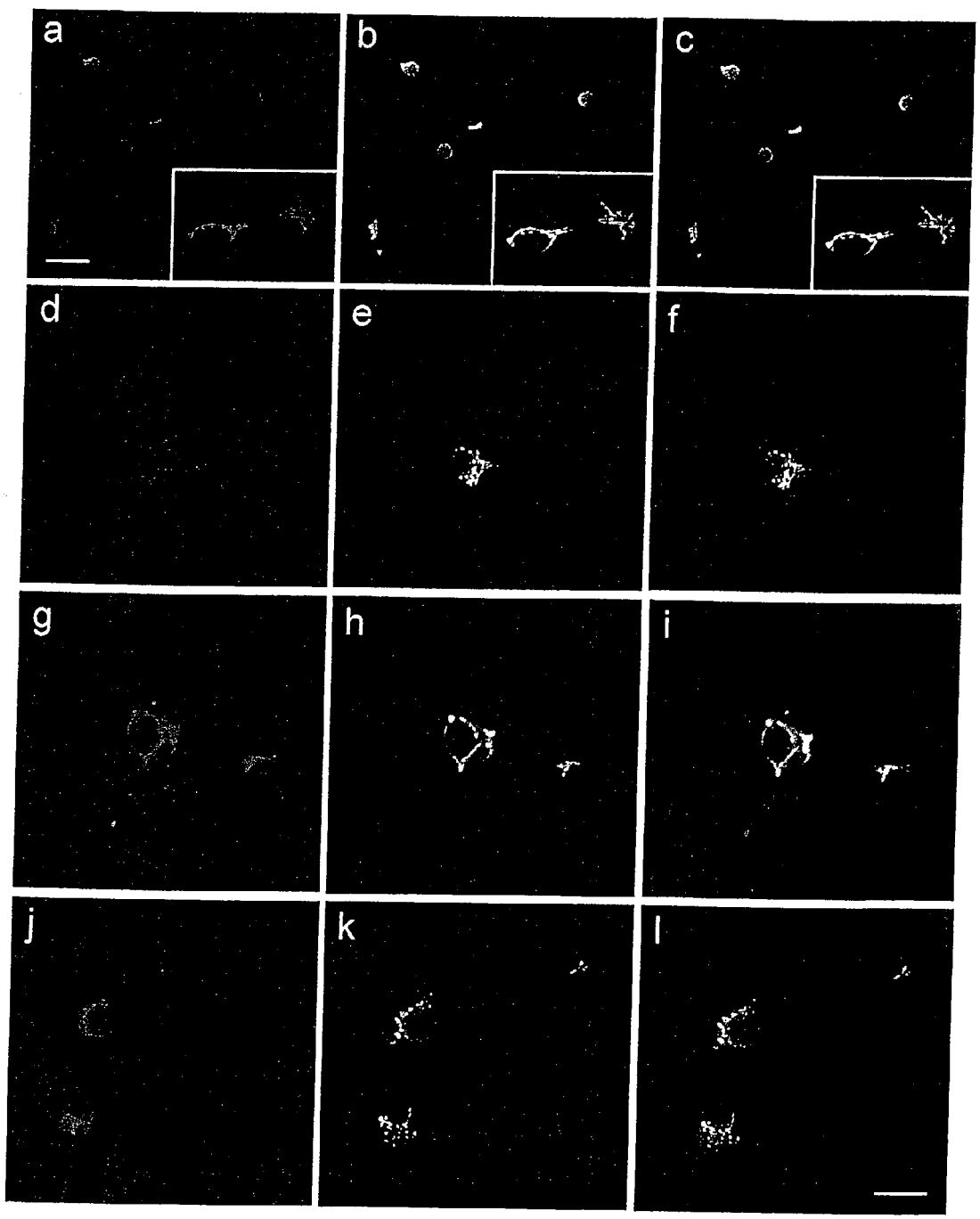
FIGS. 5A–5L show the immunofluorescence localization of Mints 1 and 2 in cultured hippocampal neurons. The left (red) and center (green) pictures show the separate fluorescence channels from double immunofluorescence labeling experiments, whereas the right pictures show the merged images. Neurons were labeled with the following antibodies: A–C, antibodies to Mint 1 (A) and Mint 2 (B). Note that the pictures show a low-magnification overview with a high-magnification inset. D–F, antibodies to synapsins (D) and Mint 2 (E). G–I, antibodies to APP (G) and Mint 1 (H). J–L, antibodies to APP (J) and Mint 2 (K). Scale bar in panel 1 (applies to the low-magnification views in A–C)=50 μm; scale bar in panel 1 (applies to the insets in A–C, and the full images in all other pictures)=20 μm.
Figure 6:
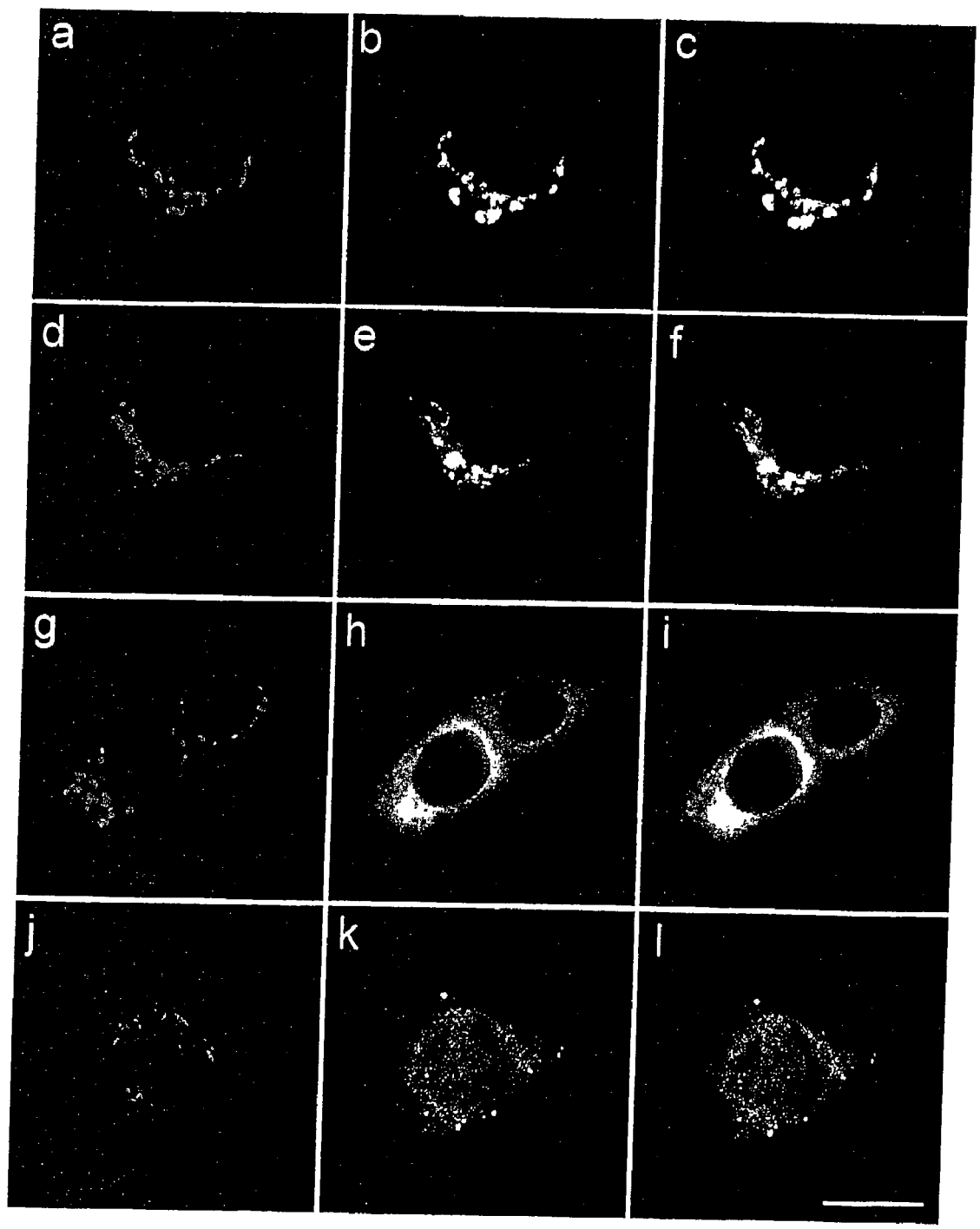
FIGS. 6A–6L show that Mints 1 and 2 are concentrated in the trans-Golgi complex. Subcellular distribution of Mints has been further investigated with a group of well-characterized markers to Golgi apparatus, endoplasmic reticulum and early endosome. Cultured hippocampal neurons were double-labeled with antibodies to the following proteins: A–C, Mint 2 (A), TGN38 (B), and merged images (C); D–F, Mint 1 (D), the Golgi 58K protein (E), and merged images (F); G–I, Mint 2 (G), calnexin (H), and merged images (I); J–L, Mint 2 (J), EEA1 (K), and merged images (L). Scale bar in L (applies to all images)=15 μm.

To examine the subcellular distribution of Mints, immunofluorescence staining of cultured hippocampal neurons was performed (FIGS. 5 and 6). Mints 1 and 2 were predominantly localized in a perinuclear compartment where they almost completely overlapped (FIGS. 5, A–C). Double labeling with antibodies to synapsins as a presynaptic marker failed to detect high levels of Mints in synapses (FIGS. 5, D–F, and data not shown). APP was largely co-localized with Mints (FIGS. 5, G–L). Compared to Mints, more APP appeared to be present in neurites, suggesting that at steady state, Mints are more concentrated in the perinuclear compartments than APP.

In the next set of experiments, cultured hippocampal neurons were double-labeled with antibodies to marker proteins to identify the perinuclear compartment containing Mints (FIG. 6). These studies demonstrated that Mints co-localize best with TGN38 (FIGS. 6, A–C, and data not shown), a marker of the trans-Golgi complex (Luzio et al., 1990, Biochem J 270:97–102). A similar localization, but not quite as precise, was observed with the 58K Golgi protein (FIGS. 6, D–F, and data not shown), a peripheral membrane protein that is enriched in, but also found outside of, the trans-Golgi complex (Bloom and Brashear, 1989, J Biol Chem 264:16083–16092).

By contrast, double labeling of neurons with antibodies to Mint 1 or 2 and the endoplasmic reticulum protein calnexin (Wada et al., 1991, J Biol Chem 266:19599–19610) failed to detect an overlap in localization (panels G–I). Similarly, the early endosomal protein EEA1 (Mu et al., 1995, J Biol Chem 270:13503–13511) exhibited a different staining pattern (panels J–L). Together these data support the conclusion that in mature neurons in situ (FIG. 4) and in culture (FIGS. 5 and 6), Mints 1 and 2 are co-localized in the trans-Golgi complex, a localization consistent with a role in APP trafficking (Borg et al., 1998a, J Biol Chem 273:14761–14766; Sastre et al., 1998, J Biol Chem 273:22351–22357) and in directing proteins out of the trans-Golgi apparatus towards defined plasma membrane domains (Rongo et al., 1998, Cell 94:751–759; Whitfield et al., 1999, Mol Biol Cell 10:2087–2100). Thus at steady state, Mints exhibit a localization that is similar to that of APP but notably distinct from that of either CASK or Munc18-1.

Example 4

A transactivation assay of APP cleavage. A function for the cytoplasmic tail of APP in activating transcription has recently been described, wherein this protein forms a protein complex with Fe65 (Cao and Südhof, 2001, Science 293: 115–120). The transcriptional activation observed in these assays could potentially be used to measure APP cleavage, but depends on Fe65 which binds to the same NPTY sequence of APP as Mints (which, however, do not activate transcription; Cao and Südhof, 2001, Science 293:115–120).

In order to test the potential function of Mints in APP cleavage and signaling, a variant of the assay was employed that allows monitoring APP cleavage independent of Fe65 binding. For this purpose, both Gal4 and VP16 were introduced into the cytoplasmic tail of $APP_{695}$ at the cytoplasmic boundary of the TMR. This assay differs from the original assay (Cao and Südhof, 2001, Science 293:115–120) in that the powerful viral transcriptional activator VP16 (Sadowski et al., 1988, Nature 335:563–564) is introduced together with the yeast DNA binding protein Gal4 into APP. Thus transactivation by APP-Gal4/VP16 is independent of the binding of cellular transcriptional activators, but can only occur after APP is cleaved by γ-secretase and the released cytoplasmic tail fragment moves into the nucleus.

DNA encoding the APP-Gal4/VP16 fusion protein was transfected into PC12, HEK293, COS, or HeLa cells, and transactivation of transcription from a co-transfected Gal4-dependent reporter plasmid encoding luciferase was measured. As a negative control, Gal4 was used alone without VP16 or APP (see Cao and Südhof, 2001, Science 293: 115–120), and as a positive control, Gal4/VP16 without APP was used. In all experiments, cells were co-transfected with a constitutive β-galactosidase expression vector in order to control for transfection efficiency and to rule out direct effects of transfected proteins on transcription. Furthermore, in all cases expression of transfected proteins was verified by immunoblotting.

Figure 7:
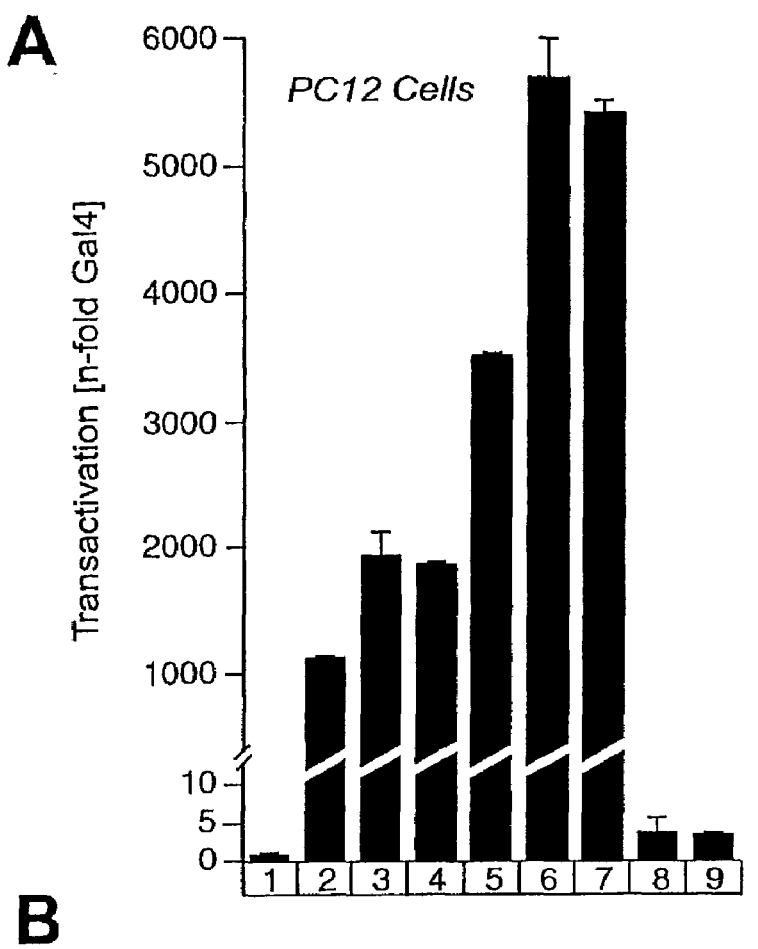
FIGS. 7A–7B show the use of APP-Gal4/VP16 fusion proteins to measure (γ-cleavage of APP. A. Relative luciferase activity in PC12 cells following transfection with plasmids containing the constructs indicated in B.
Figure 7:
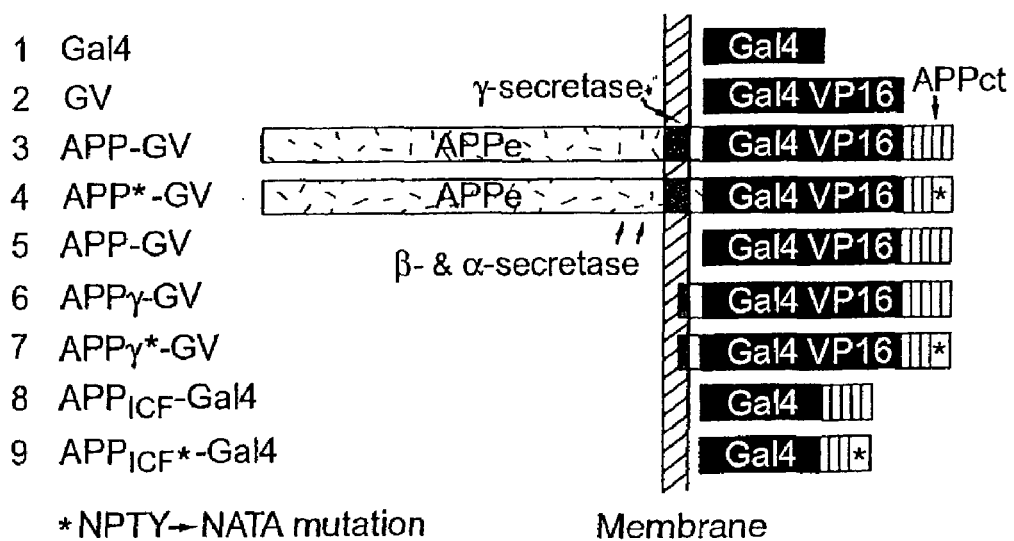

The bar diagram in FIG. 7A shows results from Gal4-transactivation assays in PC12 cells that were co-transfected with a Gal4-dependent luciferase reporter plasmid (to measure transactivation using luciferase expression), a β-galactosidase control plasmid (to normalize for transfection efficiency), and the test plasmids identified by numbers below the bars. The domain structures of the proteins encoded by the test plasmids are shown schematically in FIG. 7B ($APP_e$=extracellular sequences of APP; $APP_{ICF}$=cytoplasmic sequences of APP). Constructs marked with an asterisk (APP*-GV, $APP_{ICF}$*-GV, and $APP_{ICF}$*-Gal4) contain a point mutation in which the NPTY sequence in the cytoplasmic tail of APP is replaced by NATA. Transfected cells were harvested two days after transfection, luciferase and β-galactosidase activities were determined, and the luciferase activity was normalized for the β-galactosidase activity to control for transfection efficiency as described in the Materials and Methods. The β-galactosidase-normalized luciferase activity is expressed in relation to the activity of cells co-transfected with Gal4 alone. Data shown are from a representative experiment repeated multiple times in PC12 cells and in COS, HEK293, and HeLa cells with similar results. Abbreviations: GV, Gal4/VP16 module; $APP_{ICF}$, intracellular fragment of APP; $APP_\gamma$, γ-secretase cleavage product of APP.

In all cell types tested, full-length APP-Gal4/VP16 (APP-GV) transactivated Gal4-dependent transcription almost as strongly as Gal4/VP16 alone (~500–2,000 fold activation over Gal4 alone, depending on cell type), suggesting that cleavage of APP to release the intracellular fragment was not the major rate-limiting step (FIG. 7A, Constructs 1–3). A chimeric protein in which Gal4/VP16 was fused to the isolated cytoplasmic tail of APP ($APP_{ICF}$-GV) was an even more potent transactivator than Gal4/VP16 alone or full-length APP-Gal4/VP16 (~4,000 vs. ~500–2,000 fold activation; FIG. 7A, Construct 5). Addition of the 12 hydrophobic residues from the TMR that are present in the initial γ-cleavage product had no inhibitory effect on transactivation, but induced a moderate stimulation (FIG. 7A, Construct 6). In contrast, the cytoplasmic APP tail containing only Gal4 without VP16 ($APP_{ICF}$-Gal4) was inactive when Fe65 was not co-transfected (<5 fold activation; FIG. 7A Construct 7; Cao and Südhof, 2001, Science 293:115–120). Cleavage of APP does not appear to require binding of endogenous cellular proteins to the NPTY tail sequence (residues 684–687 of $APP_{695}$) since mutation of NPTY to NATA had no effect on transactivation. Specifically, no effect of this mutation was observed with either full-length APP or the cytoplasmic APP tail fused to Gal4/VP16 (FIG. 7A, Constructs 4 and 7).

Example 5

Figure 8:
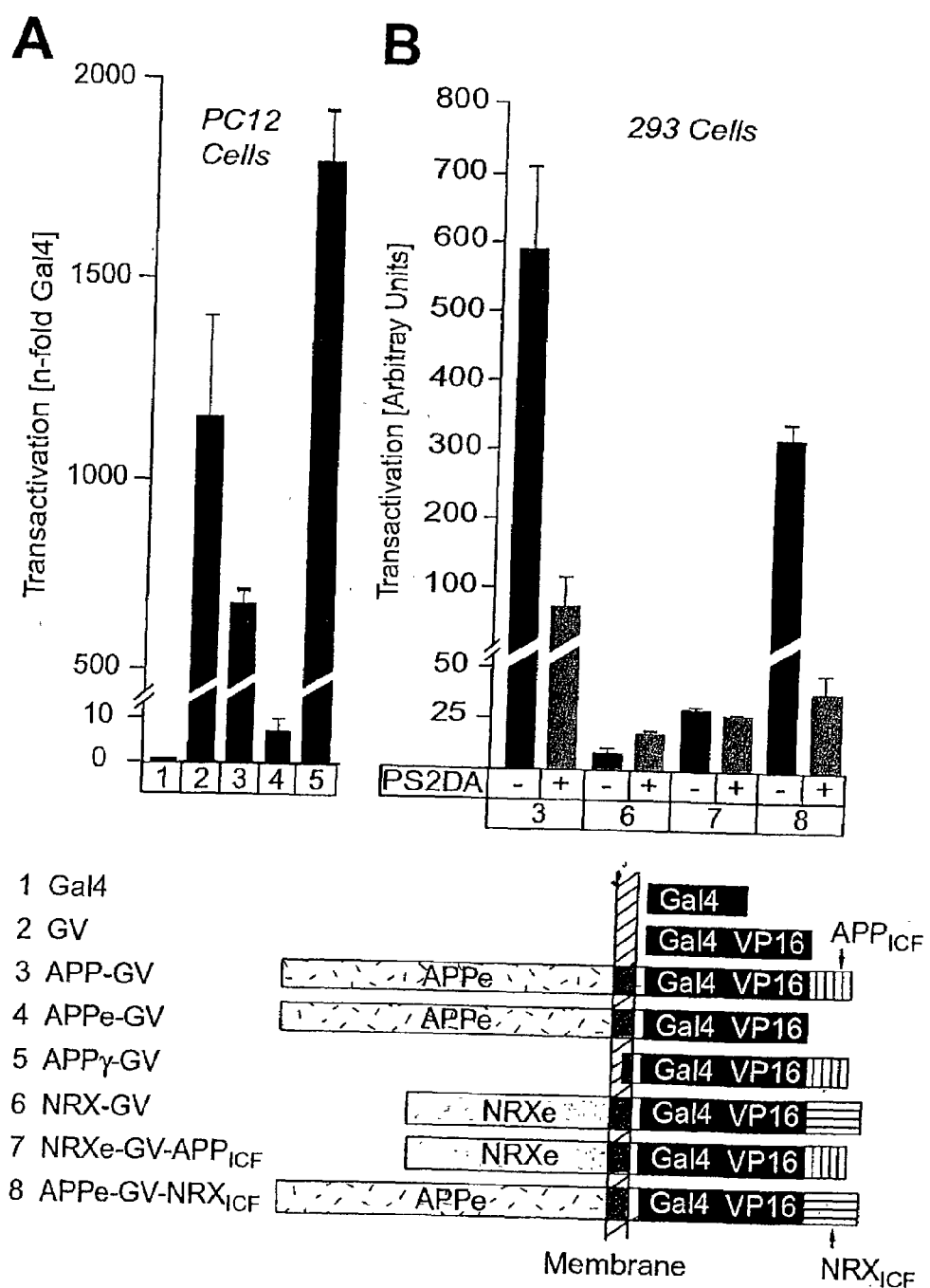
FIGS. 8A–8B show the sequence requirements of APP (γ-cleavage measured by Gal4/VP16-dependent transactivation. A. Requirements of extra- and intracellular APP sequences for transactivation. B. Test of the specific functions of extra- vs. intracellular APP sequences in (γ-cleavage, and of the effect of a dominant-negative mutant of presenilin 2 (PS2DA; Steiner et al., 1999, J Biol Chem 274:28669–28673).

APP sequences required for cleavage. The assay described above utilizes transfected cells that overexpress the respective test proteins, raising the concern that transactivation by APP-Gal4/VP16 may be caused by non-specific proteolysis of the APP-Gal4/VP16 fusion protein instead of specific α-/β- and γ-cleavage. To address this concern, assays were performed to examine determine if specific sequences of APP were required for transactivation by the embedded Gal4/VP16 module (FIG. 8).

The bar diagram in FIG. 8A shows results of Gal4/VP16-transactivation assays obtained with the constructs that, are schematically displayed and identified by numbers below the diagrams. APP-Gal4/VP16 proteins that contain all APP sequences (construct 3) or lack the intracellular (construct 4) or the extracellular and transmembrane sequences (construct 5) were analyzed as described in the previous study above. Gal4 (construct 1) and Gal4/VP16 (construct 2) were used as standardization controls to establish the background and maximal response, respectively. Transactivation was measured by constructs in which Gal4/VP16 is placed in all possible combinations into the context of the extra- and intracellular sequences of APP ($APP_e$ and $APP_{ICF}$=extracellular and cytoplasmic sequences of APP, respectively) or neurexin 1β ($NRX_e$ and $NRX_{ICF}$=extracellular and cytoplasmic sequences of neurexin, respectively). Gal4/VP16 constructs were transfected without (−) and with (+) the dominant negative presenilin 2 expression vector. All bar diagrams exhibit representative experiments in the cell types identified in A. Experiments were carried out with test plasmids co-transfected with a Gal4 luciferase reporter plasmid and a β-galactosidase control plasmid as described in the previous experiment. In A, transactivation as measured by β-galactosidase-normalized luciferase activity is expressed relative to the activity of Gal4 alone, whereas in B, transactivation as measured by luciferase activity is shown in arbitrary units only normalized to β-galactosidase activities.

In these studies, the cytoplasmic tail of APP was first removed to generate a "tailless" APP-Gal4/VP16 fusion protein in which the extracellular sequences and the TMR of APP were linked to intracellular Gal4/VP16 followed by a stop codon (APPe-GV). The tailless APP-Gal4/VP16 protein was almost completely inactive in transactivation assays compared to either Gal4/VP16 alone or to APP-Gal4/VP16 or to APPγ-GV which represents the initial γ-secretase cleavage product (FIG. 8A, Constructs 2–5). This suggests that Gal4/VP16 is not released from APP-Gal4/VP16 by non-specific degradation, and that the tail of APP is required either for recognition by the APP cleavage enzymes, or for trafficking of APP to the cleavage compartments.

To differentiate between these two possibilities, we inserted Gal4/VP16 into the cytoplasmic tail of neurexin 1β (NRx-GV). Neurexin 1β is expressed on the neuronal cell-surface similar to APP, but is not known to be processed by proteolytic cleavage (Ushkaryov et al., 1992, Science 257: 50–56). Neurexin 1β-Gal4/VP16 was nearly inactive in transactivation assays in contrast to APP-Gal4/VP16 (FIG. 8B, Construct 3 vs. Construct 6), suggesting that Gal4/VP16-mediated transactivation requires specific sequences in the APP molecule. To identify these sequences, chimeric Gal4/VP16-fusion proteins containing either extracellular APP- and intracellular neurexin 1β-sequences, or vice versa, were constructed. A fusion protein composed of the extracellular sequences and TMR of APP coupled to intracellular Gal4/VP16 and the cytoplasmic tail of neurexin 1 ($APP_e$-$GV$-$NRX_{ICF}$) strongly transactivated transcription (FIG. 8B, Construct 8). In contrast, the reverse fusion protein of the extracellular neurexin sequences and the neurexin TMR with the cytoplasmic APP sequences ($NRX_e$-$GV$-$APP_{ICF}$) was inactive (FIG. 8B, Construct 7). These experiments demonstrate that the extracellular sequences of APP are essential for proper cleavage, in agreement with results of Struhl and Adachi, 2000, Mol Cell 6:625–36.

Although the intracellular sequences of APP are also essential for its processing (see "tailless" mutant, FIG. 8A), they can be functionally replaced by the intracellular fragment of a plasma membrane protein like neurexin that exhibits no sequence similarity with APP, and in particular does not contain an NPxY sequence (Ushkaryov et al., 1992, Science 257:50–56). This may indicate a role of the APP tail in trafficking to a cleavage compartment at the plasma membrane, or derived from the plasma membrane.

Finally, to test if presenilins are involved in transactivation by APP-Gal4/VP16, a plasmid encoding a dominant negative mutant of presenilin 2 (Steiner et al., 1999, J Biol Chem 274:28669–28673) was co-transfected along with a plasmid encoding APP-Gal4/VP16 (FIG. 8B). Transactivation of Gal4-dependent transcription by full-length APP-Gal4/VP16 was inhibited by the presenilin 2 mutant, whereas the small amount of residual transactivation observed with neurexin 1β-Gal4/VP16 was insensitive to presenilin 2 (FIG. 8B, Construct 3 vs. Construct 6). As expected, mutant presenilin 2 also potently inhibited transactivation by the fusion protein of the extracellular domain of APP with intracellular neurexin sequences (FIG. 8B, Construct 8), but had no effect on the residual transactivation observed with the reverse fusion protein containing the extracellular domain of neurexin 1β coupled to the cytoplasmic tail of APP (FIG. 8B, Construct 7).

Example 6

Figure 9:
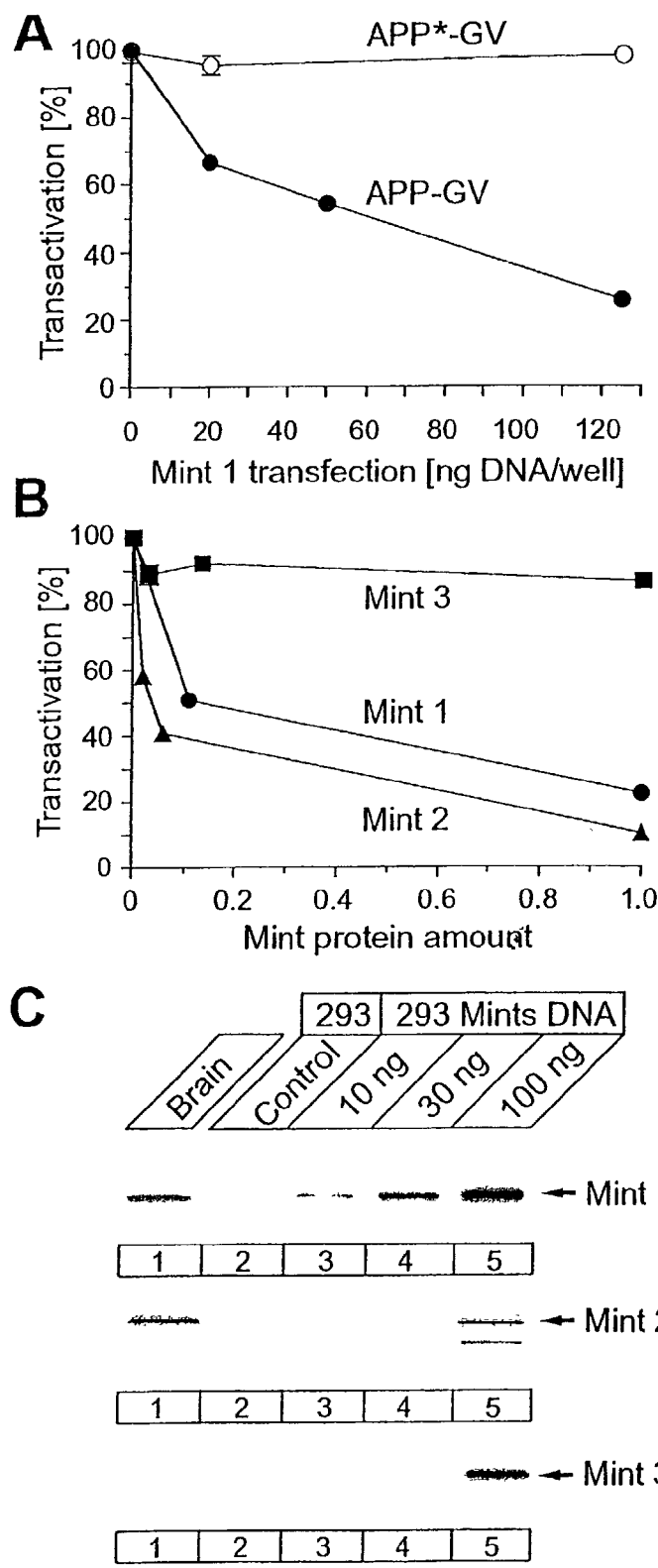
FIGS. 9A–9C show that Mints 1 and 2 but not Mint 3 inhibit transactivation by APP-Gal4/VP16 fusion proteins. A. Dose-dependent inhibition by Mint 1 of wild-type APP-Gal4/VP16 transactivation but not of APP-Gal4/VP16 carrying a point mutation in the cytoplasmic NPTY binding sequence for Mints (APP*-GV). B. Effects of Mints 1, 2, and 3 on APP-Gal4/VP16 dependent transactivation. C. Quantitated immunoblot analysis of the Mints expressed in the experiment shown in B.

Mint 1 inhibits transactivation mediated by APP-Gal4/VP16. The transactivation assay was next used to study the effects of Mints on APP. A constant amount of wild-type or mutant APP-Gal4/VP16 plasmid (100 ng DNA/well) was co-transfected with the indicated amounts of Mint 1 expression vector into HEK293 cells. Transactivation and Mints levels in the cells were quantified in the same samples as described in the Materials and Methods. Co-transfection of Mint 1 strongly inhibited transactivation mediated by APP-Gal4/VP16 (FIG. 9A). This inhibition was abolished by mutation of the NPTY sequence in the cytoplasmic tail of APP-Gal4/VP16, consistent with the notion that direct binding of Mint 1 to APP is required.

Comparison of the activity of the three Mint isoforms in the transactivation assay demonstrated that Mints 1 and 2 potently inhibited transactivation by APP-Gal4/VP16, whereas Mint 3 had no significant effect (FIG. 9B). In these studies, Mint amounts in transactivation assay samples were quantified on immunoblots and are expressed as a fraction of the amount observed with the maximal amount of DNA transfected to control for the non-linearity of the relation between transfected DNA and expressed protein. Immunoblotting confirmed that all three Mints were expressed at high levels in the co-transfected cells (FIG. 9C).

Since all three Mints bind to APP in vitro and in transfected cells (FIGS. 1 and 2), the selective inability of Mint 3 to inhibit transactivation was surprising. To gain insight into the mechanism by which Mint 1 inhibits APP-Gal4/VP16 mediated transactivation, and to understand why Mint 3 has no effect, a series of Mint mutants were examined. In these studies, HEK293 cells were co-transfected with a constant amount of APP-Gal4/VP16 expression vector and reporter plasmids, and increasing amounts of expression vectors expressing wild-type Mint 1 or mutants of Mint 1 carrying point mutations in the first or second PDZ domains (Mint 1 PDZ1* or PDZ2*, respectively) or lacking both C-terminal PDZ domains (Mint 1 ΔPDZ). Transactivation and Mint 1 amounts in the cells were then quantified in the same samples as described in the Materials and Methods. All transactivation levels in the experiments reported in FIGS. 10A and 10B are normalized for the amount of transactivation observed under control conditions.

These studies showed that an inactivating point mutation in the first PDZ domain of Mint 1 or deletion of both PDZ domains that were studied above in the presenilin-binding experiments (FIG. 3) dramatically increased the inhibition of transactivation by Mint 1 (FIG. 10A). In contrast, the second PDZ domain point mutation did not alter the inhibitory effect of Mint 1.

mutants exhibited different expression levels, the relative amounts of expressed protein were quantified using $^{125}$I-labeled secondary antibodies. These quantitations showed that the PDZ-domain deletion mutant was approximately 10 times more potent than wild-type Mint 1 (FIG. 10A). A Mint 3 mutant with a PDZ-domain deletion was also tested; this mutant was completely inactive in the assay similar to wild-type Mint 3 (FIG. 10B, C). Control transfections showed that the various Mint 1 proteins did not inhibit general transcription, but specifically impaired transactivation by APP-Gal4/VP16 (data not shown).

Figure 10:
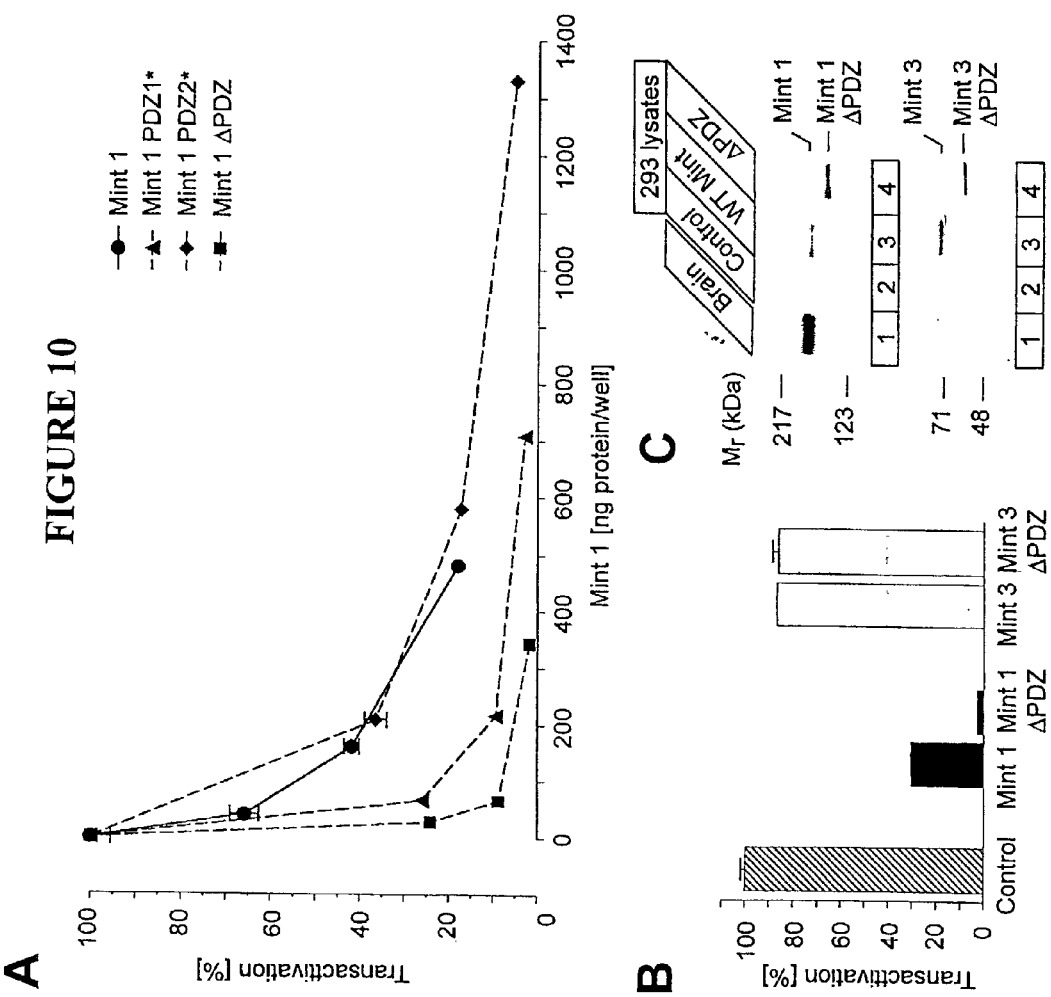
FIGS. 10A–10C show the structure-function analyses of Mint 1 indicating the role of PDZ domains in inhibiting APP-Gal4/VP16 dependent transactivation. A. Transactivation as a function of protein concentration. B. Transactivation observed in HEK293 cells co-transfected with APP-Gal4/VP16 and a control plasmid, or wild-type Mint 1, a Mint 1 mutant lacking the PDZ-domains, wild-type Mint 3, or a Mint 3 mutant lacking both PDZ domains. C. Immunoblot analysis of the Mint mutants analyzed in B to control expression of the constructs in the experiments shown.
Figure 11:
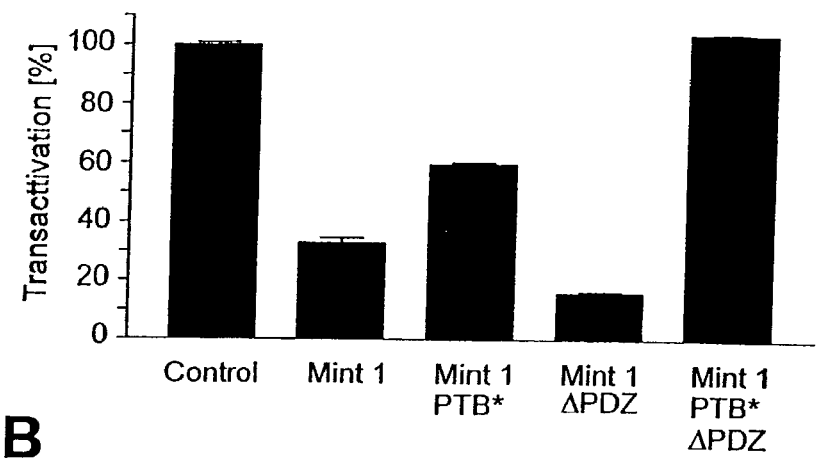
FIGS. 11A–11C show that the PTB and PDZ domains of Mint 1 cooperate in inhibiting transactivation by APP-Gal4/VP16. A. Effect of co-transfecting Mint 1 and various Mint 1 point-mutants in the PTB-domain and the first PDZ domain with APP-Gal4/VP16. B. Effect of deleting the N-terminal isoform-specific Mint 1 sequences on inhibition of transactivation. C. Quantitated immunoblot analysis of Mint expression in the experiment shown in B.
Figure 11:
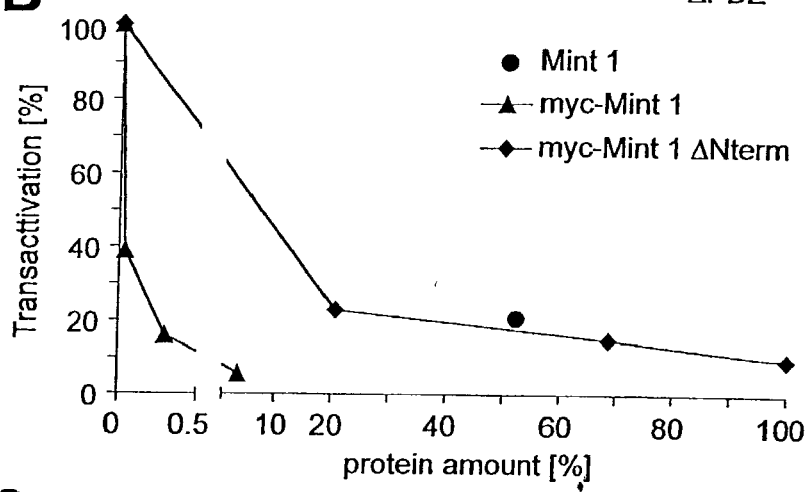
Figure 11:
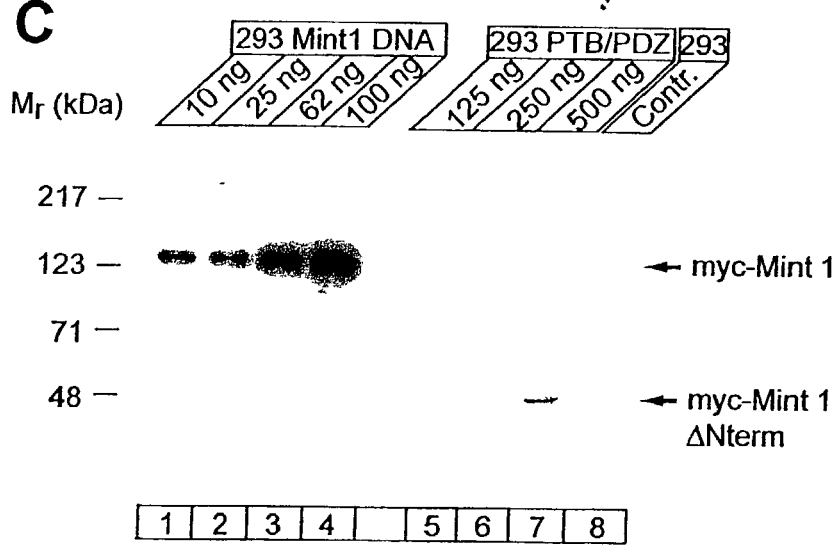

The results of FIG. 10 suggest that Mint 1 binding to APP may couple it to another protein which binds to the first PDZ domain, implying among others that the two PDZ domains of Mint 1 are not equivalent. To examine this further, the effect of mutating the PTB domain of Mint 1 on its inhibitory activity was examined. Based on the available structural information (Zhang et al., 1997, EMBO J. 16:6141–6150), a mutant Mint 1 PTB* was designed in which critical residues involved in binding to the NPTY sequence of APP were altered. Specifically, YQEF$_{(613-616)}$ was mutagenized to SQES$_{(613-616)}$. In this study, the same DNA amount of control vector or Mint 1 vector or the vectors encoding the indicated Mint 1 mutants was co-transfected into HEK293 cells with the APP-Gal4/VP16 and reporter plasmids, and transactivation was determined as described in the Materials and Methods. As shown in FIG. 11A, the PTB domain mutation decreased inhibition of transactivation, but did not abolish it, possibly because the mutant PTB domain retained residual binding activity for APP. Only the combination of the PTB domain mutation with the point mutation in the first PDZ domain of Mint 1 or with the deletion of both PDZ domains abolished its inhibitory effect on transactivation (FIG. 11A).

Conversely, after deletion of the isoform-specific N-terminal residues of Mint 1 (the sequences that are N-terminal to the PTB and PDZ domains and account for 451 of the 839 residues of Mint 1; Okamoto and Südhof, 1997, J Biol Chem 272:31459–31464), the specific inhibitory activity of Mint 1 was also increased significantly (FIG. 11B). In these studies, the same amounts of myc-tagged full-length Mint 1 or an N-terminally truncated Mint 1 mutant containing only the PTB- and PDZ-domains were co-transfected with APP-Gal4/VP16 and reporter constructs into HEK293 cells, and their specific inhibitory activity on transactivation was determined. To exclude an effect of the myc-epitope, the specific activity of wild-type and myc-tagged Mint1 was compared.

Expressed proteins were detected using antibodies against the myc epitope. The expression level of the N-terminal Mint 1 deletion mutant was low, suggesting that it may be partially cytotoxic (FIG. 11C).

Example 7

Effect of mints on transactivation by the intracellular fragment of APP. A possible explanation for the effects of Mints on transactivation by APP-Gal4/VP16, based on the binding of Mints to APP via their PTB domain and to presenilins via their PDZ domains (FIGS. 1–3) would be that the Mints 1 and 2 interfere with γ-cleavage of APP. However, the facts that Mint 3 also binds to APP and presenilins better than Mint 2 but does not inhibit transactivation, and that both Mint 1 PDZ domains bind to presenilin 1 in vitro but only the first PDZ-domain is involved in the inhibition of transactivation argue against this hypothesis. An alternative explanation for the transactivational inhibition is that Mints 1 and 2 act on the APP cytoplasmic tail after it has been released by γ-cleavage.

Figure 12:
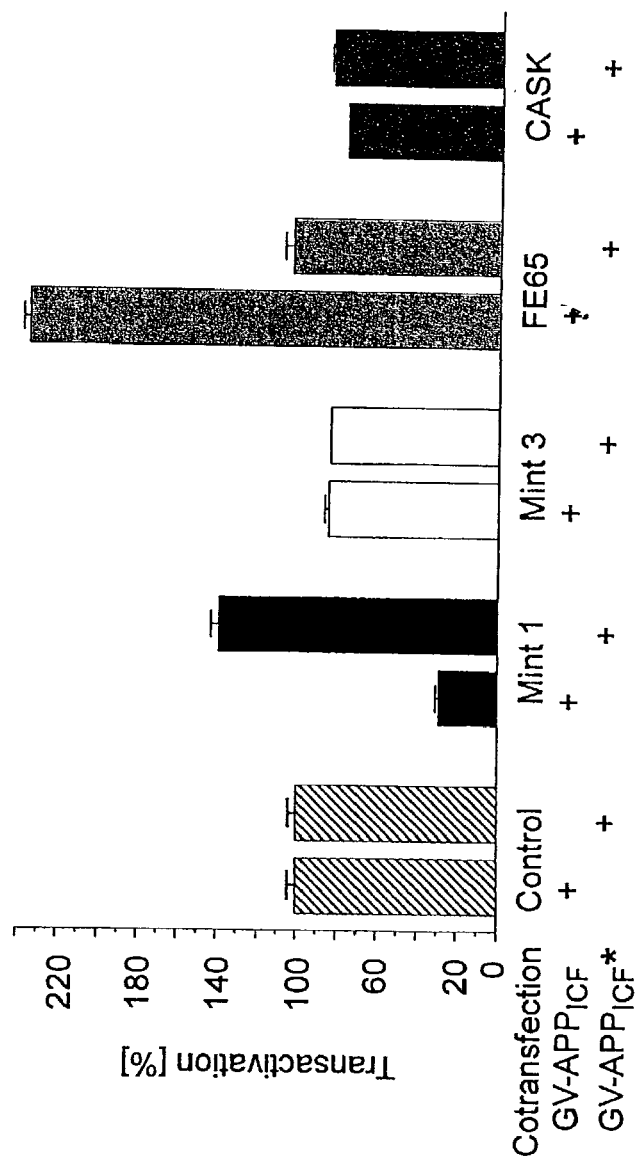

To differentiate between these explanations, we measured the effect of Mints on transactivation by the "precleaved" cytoplasmic tail of APP fused to Gal4/VP16 (APP$_{ICF}$-GV). To distinguish specific, i.e. binding-dependent, effects from non-specific effects, a mutant cytoplasmic tail of APP that was unable to bind to Mints (APP$_{ICF*}$-GV) was also examined in the same experiments. In addition, Mints were compared to Fe65 as another APP-binding protein, and to CASK as an unrelated control (FIG. 12). In these studies, constant amounts of plasmids encoding APP$_{ICF}$-GV or the NPTY$_{(684-687)}$ to NATA$_{(684-687)}$ mutant APP$_{ICF*}$-GV were co-transfected into HEK293 cells together with reporter plasmids and expression vectors for the indicated proteins.

Mint 1 expression significantly inhibited transactivation mediated by the cytoplasmic tail of APP fused to Gal4/VP16; this inhibition was only observed when the APP tail contained a normal Mint binding sequence (FIG. 12). A similar inhibition was detected with Mint 2 (data not shown). Mint 3, by contrast, had no significant effect, in agreement with the results obtained with full-length APP-Gal4/VP16 (FIGS. 9B and 10B). Fe65 enhanced transactivation, again only when the NPTY sequence in the cytoplasmic tail was intact (FIG. 12), consistent with the overall function of Fe65 in stimulating transcription (Cao and Südhof, 2001, Science 293:115–120). CASK used as a negative control had no effect on transactivation. Identical effects of both Mints 1 and 3, their PDZ truncation mutants, and Fe65 were observed when transactivation was assayed by a construct that mimicked the initial γ-cleavage product of APP, i.e. that contained 12 hydrophobic residues from the TMR preceding the cytoplasmic tail of APP (data not shown). These results demonstrate that Mint 1 inhibits transactivation downstream of APP cleavage, and that this effect is highly specific for neuronal vs. ubiquitous Mints.

Example 8

Figure 14:
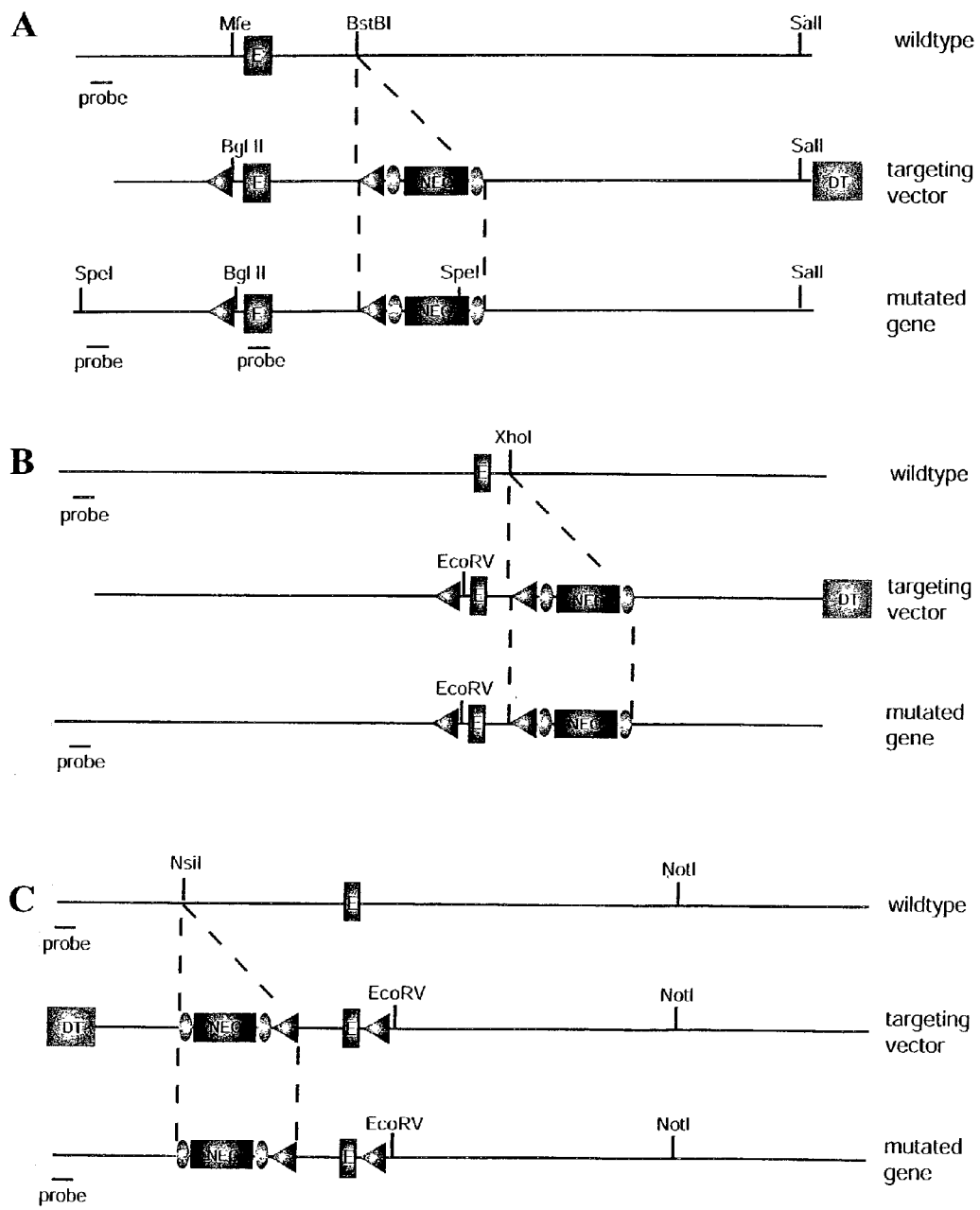
FIGS. 14A–14C depict the strategies used for the production of transgenic mice in which the function of the Mint 1 (A), Mint 2 (B) or Mint 3 (C) gene has been eliminated. In each case, schematic representations of the wild-type gene, the targeting vector and the mutant gene are provided.

Generation of Mint 1, Mint 2 and Mint 3 KO mice. The strategies used for the creation of the Mint 1, Mint 2 and Mint 3 KO mice are shown in FIG. 14, panels A–C, respectively. Briefly, genomic clones encoding exons of the Mint 1, 2 and 3 genes were mapped and inducible targeting vectors were constructed. In these inducible targeting vectors, an exon of the Mint gene was flanked by loxP sites, and a neomycin gene cassette was introduced which was flanked by flp sites for positive selection. A negative selection marker diphtheria toxin (DT) was placed at the end of the genomic sequences for negative selection. Embryonic stem (ES) cells were electroporated with Mint 1, 2 and 3 inducible targeting vectors and subjected to positive and negative selection. Double-resistant clones were screened by Southern analysis to verify proper targeting.

Figure 15:
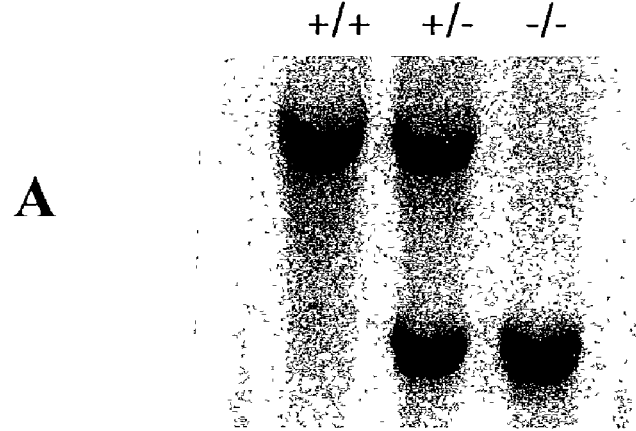
FIGS. 15A–15B show Southern blot analyses of Mint 1 knockouts. A. Genomic tail DNA from offspring of heterozygous interbreedings was digested with SpeI and hybridized with the outside probe shown in FIG. 14A. The upper band corresponds to wild-type allele and the lower to the mutant allele. B. Southern blot analysis of Mint 1 knockouts. Genomic tail DNA from offspring of heterozygous interbreedings was digested with SpeI and hybridized with a probe to the first exon shown in FIG. 14A.
Figure 15:
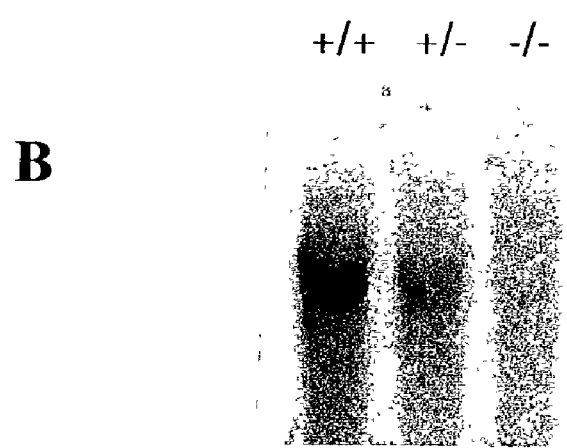

All three inducible targeting vectors could be successfully employed to generate recombinant ES cells. Injection of these cells into pseudopregnant female hosts led to the production of chimeric offspring carrying the mutant allele, which was subsequently shown to be transmitted through the germline. Crossing of the heterozygous animals led to the production of null mutant knockout mice. As shown for Mint 1 KO mice in FIG. 15, Southern blot analysis was employed to confirm the presence of the wild-type or mutant allele.

Mint 1 null mutant knockout mice are viable and fertile. Although incompletely characterized at present, they show no obvious abnormalities other than that they weight comparatively less than their age-matched, wild-type littermates. No changes in protein expression in Mint 1-associated proteins such as munc18, CASK, velis, neurexins and APP were observed. There were no abnormalities in excitatory synaptic transmission or plasticity, but an increase in the magnitude of paired-pulse depression was noted at inhibitory synapses in the Mint 1 null mutant knockout mice, as compared to wild-type littermates, suggest that these animals may exhibit some change in GABA release from inhibitory terminals. A second group has also recently reported the creation and characterization of a transgenic Mint-1 knockout mouse. See Mori et al., Neurosci Res. 2002;43:251–257.

Null mutant knockout mice for Mint 2 and Mint 3 are also viable and fertile. Phenotypic characterization of these animals is in progress.

The foregoing data provide a model for the interaction between proteins of family and the cytoplasmic tail of the APP wherein binding of Mint 1 or 2 to the cytoplasmic tail of APP inhibits the transcriptional activation otherwise mediated by this protein.

All references cited herein are incorporated herein in their entirety. of modulating transcriptional activation. Such compounds may be useful as candidate therapeutics for AD, or as models for the rational design of drugs useful for the treatment of AD.

The present invention further provides for transgenic knockout mice for Mint 1, Mint 2 and Mint 3. These animals may be useful for elucidating the pathophysiology of AD and for developing improved treatments for this disease.

In other embodiments, the present invention is directed to vectors, transfected cells and kits useful for modulating transcriptional activation or for the identification of compounds that can modulate APP-mediated transactivation.

BRIEF DESCRIPTION OF THE DRAWINGS

FIGS. 1A–B shows the similarly tight binding of Mints 1, 2, and 3 to the cytoplasmic tail of APP. A. Immunoblot analysis of Mint binding to the immobilized cytoplasmic tail of APP. B. Quantitation of the amount of Mints bound to the immobilized cytoplasmic tail of APP as percent of Mints in the starting brain extract.

FIGS. 2A–C shows that co-transfection of Mints 1, 2, or 3 increases the steady-state levels of APP. A. Immunoblot analysis of HEK293 cells co-transfected with expression plasmids encoding $APP_{695}$, Mints 1–3, and Fe65 as indicated. B. Quantitation of the levels of $APP_{695}$ in transfected HEK293 cells shown in A. C. Immunoprecipitation assay of Mint binding to APP.

FIG. 3A–C shows the binding of both PDZ domains of Mints to the cytoplasmic C-terminal sequence of presenilins. A. Binding of Mints 1 and 3 to presenilin 1. B. Percent of Mints solubilized from a rat forebrain membrane preparation that bound to an affinity column containing a peptide corresponding to the C-terminus of

We claim:

1. A method of identifying compounds that modulate transcriptional activation in a target cell comprising:
   (a) contacting a target cell with a test compound, wherein the target cell comprises
      (i) a first nucleic acid encoding an amyloid-β precursor protein (APP) fusion protein comprising a modified cytoplasmic tail of the APP, wherein the cytoplasmic tail is modified to include a heterologous DNA-binding domain of a transcription factor, and a transcriptional activator of the same or a different transcription factor, and
      (ii) a second nucleic acid encoding a reporter gene whose transcription is regulated by the DNA-binding domain of a transcription factor contained in the APP fusion protein (iii) a third nucleic acid encoding a Mint 1 protein (SEQ ID NO:9)

(b) measuring the levels of reporter gene transcription that occurs in the presence and absence of the test compound; and (c) comparing the levels of reporter gene transcription measured in step (b) wherein increased or decreased levels of reporter gene transcription in the presence of the test compound indicate that the compound modulates transcriptional activation.

2. The method of claim 1 wherein the DNA-binding domain is Gal4 or LexA.

3. The method of claim 1 wherein the transcriptional activation domain is VP16.

4. The method of claim 1 wherein the reporter gene transcription levels are measured by measuring expression of the reporter gene.

5. The method of claim 1 wherein the cell is a eukaryotic cell.

6. The method of claim 5 wherein the cell is a mammalian cell.

7. The method of claim 6 wherein the cell is a human cell.

* * * * *